US012720250B2

(12) United States Patent
Ayzenberg et al.

(10) Patent No.: US 12,720,250 B2
(45) Date of Patent: Aug. 25, 2026

(54) METHOD, DEVICE, AND SYSTEM OF AN EARPHONE HAVING INCREASED COMFORT THROUGH EXTERNAL-FACING CHARGING CONNECTIONS, ENHANCED CONTROLS THROUGH DIRECTION AND/OR MOTION EVALUATION, AND/OR ACCURATE PHYSIOLOGICAL FEATURE EXTRACTION THROUGH AUDIO-MOTION SENSOR CORRELATION

(71) Applicant: Stealth Labs Inc., Brookline, MA (US)

(72) Inventors: Yadid Ayzenberg, Brookline, MA (US); Amir Lazarovich, Apex, NC (US); Hardik B. Patel, Wilmington, NC (US); Daniel Wilken Pesavento, Wilmington, NC (US)

(73) Assignee: Stealth Labs Inc.

( * ) Notice: Subject to any disclaimer, the term of this patent is extended or adjusted under 35 U.S.C. 154(b) by 167 days.

(21) Appl. No.: 18/529,201

(22) Filed: Dec. 5, 2023

(65) Prior Publication Data

US 2025/0080896 A1 Mar. 6, 2025

Related U.S. Application Data

(60) Provisional application No. 63/536,026, filed on Aug. 31, 2023.

(51) Int. Cl.
*H04R 1/10* (2026.01)
*A61B 5/11* (2006.01)
(Continued)

(52) U.S. Cl.
CPC .......... *H04R 1/1041* (2013.01); *A61B 5/1126* (2013.01); *G06F 3/0346* (2013.01);
(Continued)

(58) Field of Classification Search
CPC .. H04R 1/1041; H04R 1/1016; H04R 1/1025; H04R 1/105; H04R 1/1075;
(Continued)

(56) References Cited

U.S. PATENT DOCUMENTS 9,799,188 B2 10/2017 Lee et al.
9,906,636 B2 2/2018 Lee et al.
(Continued)

FOREIGN PATENT DOCUMENTS

CN 102065350 B 5/2011
CN 105097000 A 11/2015
(Continued)

OTHER PUBLICATIONS

Gülcan Bahcecioglu Turan et al., The effects of eye masks and earplugs on sleep quality, anxiety, fear, and vital signs in patients in an intensive careunit: A randomised controlled study. https://onlinelibrary.wiley.com/doi/epdf/10.1111/jsr.14044.
(Continued)

*Primary Examiner* — Ammar T Hamid
(74) *Attorney, Agent, or Firm* — Peter Jensen-Haxel

(57) ABSTRACT

Disclosed are a method, a device, and/or a system of an earphone having increased comfort through external-facing charging connections, enhanced controls through direction and/or motion evaluation, and/or accurate physiological feature extraction through audio-motion sensor correlation. In one embodiment, an earphone includes a housing, a speaker configured to audibly coupled to an ear canal, a battery, a wireless antenna, and a charging connector. The inside face of the housing faces inward toward a concha of the ear, and the outside face faces outward when the earphone is seated in the ear such that at least an exposed region is unobstructed to a finger of the user. The charging connector of the earphone is electrically coupled to the battery
(Continued)

and positioned on the outside face of the housing to prevent contact with the ear, reduce corrosion of the charging connector of the earphone, reduce dirt buildup, and/or improve comfort.

20 Claims, 21 Drawing Sheets

(51) Int. Cl.
*G06F 3/0346* (2013.01)
*G06F 3/041* (2006.01)
*G06F 3/16* (2006.01)
*H01Q 1/27* (2006.01)
*H04R 1/1025* (2026.01)
*H04R 5/00* (2006.01)

(52) U.S. Cl.
CPC .......... *G06F 3/04186* (2019.05); *G06F 3/165* (2013.01); *H01Q 1/273* (2013.01); *H04R 1/1016* (2013.01); *H04R 1/1025* (2013.01); *H04R 1/105* (2013.01); *H04R 1/1075* (2013.01); *A61B 2562/0219* (2013.01); *H04R 2420/07* (2013.01)

(58) Field of Classification Search
CPC ............. H04R 2420/07; G06F 3/04186; G06F 3/0346; G06F 3/165; A61B 5/1126; A61B 2562/0219; H01Q 1/273
USPC ........................................................ 381/74, 1
See application file for complete search history.

(56) References Cited

U.S. PATENT DOCUMENTS

| | | | |
|---|---|---|---|
| 11,197,974 B2 | 12/2021 | Kremer et al. | |
| 11,420,011 B2 | 8/2022 | Keshavan et al. | |
| 11,617,854 B2 | 4/2023 | Freed et al. | |
| 12,058,488 B2 | 8/2024 | Chen et al. | |
| 2011/0034756 A1 | 2/2011 | Hacking et al. | |
| 2019/0231197 A1 | 8/2019 | Kirszenblat et al. | |
| 2023/0269512 A1* | 8/2023 | Wang .................. | H04R 1/1016 381/74 |
| 2023/0380793 A1 | 11/2023 | Ahmed et al. | |

FOREIGN PATENT DOCUMENTS

| | | |
|---|---|---|
| CN | 105225679 B | 1/2016 |
| CN | 106227340 A | 12/2016 |
| CN | 108810749 B | 11/2018 |
| CN | 109413537 A | 3/2019 |
| CN | 109561219 A | 4/2019 |
| CN | 109936999 B | 6/2019 |
| CN | 110928203 B | 3/2020 |
| CN | 211128146 U | 7/2020 |
| CN | 112087685 A | 12/2020 |
| CN | 113521485 B | 10/2021 |
| CN | 113891209 A | 1/2022 |
| CN | 114302276 A | 4/2022 |
| CN | 115361625 A | 11/2022 |
| CN | 116939420 A | 10/2023 |
| CN | 117939345 A | 4/2024 |
| CN | 117998244 A | 5/2024 |
| CN | 118509782 B | 8/2024 |
| EP | 2974648 A1 | 1/2016 |
| EP | 4101377 A1 | 12/2022 |
| KR | 100571811 B1 | 4/2006 |
| WO | 2011047216 A2 | 4/2011 |
| WO | 2014057921 A1 | 4/2014 |
| WO | 2014057979 A1 | 4/2014 |
| WO | 2017004874 A1 | 1/2017 |

OTHER PUBLICATIONS

Motoki Yoshihi et al., Estimating Sleep Stages using a Head Acceleration Sensor. https://pmc.ncbi.nlm.nih.gov/articles/PMC7867075/#notes1.

* cited by examiner

Ear Tip 104
Retainer 108
SOND
Charging Connector 204
Magnet 208A
Ground Connector 206
Magnet 208B
Earbud 100
(Front View 650A)

Magnet 208B
Magnet 208A
Ground
Connector 206
Retainer 108
Ear Tip 104
Earbud 100
(Top View 650B)

Retainer 108
Ear Tip 104
Charging
Connector 204
Magnet 298A
Earbud 100
(Side View 650C)

Directional Locking Process Flow 1650

*Fig. 18* Anatomical Recoil Control Recognition Process Flow 1850

Vibration Control Recognition Process Flow 1950

Physiological Feature Identification Process Flow 2250

METHOD, DEVICE, AND SYSTEM OF AN EARPHONE HAVING INCREASED COMFORT THROUGH EXTERNAL-FACING CHARGING CONNECTIONS, ENHANCED CONTROLS THROUGH DIRECTION AND/OR MOTION EVALUATION, AND/OR ACCURATE PHYSIOLOGICAL FEATURE EXTRACTION THROUGH AUDIO-MOTION SENSOR CORRELATION

CLAIM FOR PRIORITY

This patent application claims priority from, and hereby incorporates by reference: U.S. provisional patent application No. 63/536,026, entitled 'INCREASED COMFORT, ATTRACTIVENESS, RELIABILITY AND/OR DURABILITY OF AN EARPHONE SUCH AS AN EARBUD THROUGH EXTERNAL CHARGING CONNECTIONS', filed Aug. 31, 2023.

FIELD OF TECHNOLOGY

This disclosure relates generally to data processing devices and, more particularly, to a method, a device, and/or a system of an earphone having increased comfort through external-facing charging connections, enhanced controls through direction and/or motion evaluation, and/or accurate physiological feature extraction through audio-motion sensor correlation.

BACKGROUND

Earphones that provide sound directly to an ear canal of a user, including earbuds that are held in place by the shape of the ear, may have become prevalent personal devices. The attractiveness, comfort, durability, reliability, ease of control interactions, and other features of earphones are increasingly valued in both business and consumer markets.

One valued attribute of earphones may include a small form-factor that can increase comfort. This may be especially useful for earbuds that are intended to be positioned within and/or held by the ear so that the earbuds easily and ergonomically fit. Certain specialized uses, for example earphones that aid in sleep, may implicate comfort considerations, for example ensuring a user sleeping on their side (sometimes known as a "side sleeper") does not experience increased pressure on sensitive parts of ear from the earphone and/or earbud. Sometimes the number of intended features and components, or their existing configuration on the outside of the earphone, can create tension with defining a compact and/or comfortable form factor. It is therefore advantageous to find new, comfortable form factors for earphones, and especially earbuds.

Another aspect of value in earphones is reliability and/or durability. Certain external and internal component configurations can lead to higher durability. For example, certain electrical components, when coming in contact with the skin (e.g., can fill with dirt, corrode, and/or otherwise fail). Certain specialized uses, for example earphones that aid in sleep, may amplify these needs because the earphones may experience prolonged periods of reduced air flow and/or build up increased sweat. It is therefore advantageous to find new, reliable and durable form factors and component configurations for earphones.

Yet another aspect of value in earphones is an easy-to-use, responsive, and intuitive interface. It may be valuable to allow an earphone to be controlled directly without need of another device, such as a smartphone. Certain specialized uses, for example earphones that aid in sleep, may especially benefit because a user may not need to interact with the smartphone, which may be known to disrupt sleep. However, directly controlling the earphone can be a challenge due to the limited space of the form factor in which to provide touch inputs or other control interactions. Additionally, it also may be valuable to ensure that control signals do not generate false positives, as these can be annoying or make the user feel as if the user is not in control. For earphones that can be used for sleeping, false positives may wake the user (e.g., changing a sound track accidentally, turning off noise canceling, etc.). It is therefore advantageous to find new and improved ways to allow for direct control of earphones and/or reduce false positives in control input, which may be especially useful in earbuds and/or earbuds indented to aid in sleeping.

Yet another valuable aspect may be an earphone and/or earbud with an ability to gather physiological data that can be used to determine physiologically indicators (e.g., a heart beat, a breath), and therefore physiological features (e.g., heart rate, respiration rate). Certain specialized uses, for example earphones that aid in sleep, may especially benefit because such physiological indicators and/or physiological features may be able to be utilized to determine a sleep state (e.g., an awake state, a sleep state, a rapid-eye movement (REM) sleep state, etc.). However, it can be a challenge to accurately determine physiological indicators, especially utilizing small devices such as earphones and/or earbuds. Therefore, it is advantageous to find new and improved ways to more reliably, consistently, and/or accurately determine physiological indicators.

SUMMARY

Disclosed are a method, a device, and/or a system of an earphone having increased comfort through external-facing charging connections, enhanced controls through direction and/or motion evaluation, and/or accurate physiological feature extraction through audio-motion sensor correlation.

In one embodiment, an earphone includes a housing, an inside face of the housing, an outside face of the housing, a speaker audibly coupled to an ear canal of the ear, a battery, a wireless network interface controller, a wireless antenna, and a charging connector. The inside face of the housing faces toward a concha of an ear of a user when the earphone is seated in the ear. The outside face of the housing faces outward when the earphone is seated in the ear such that at least an exposed region is unobstructed to a finger of the user. The charging connector of the earphone is electrically coupled to the battery and positioned on the outside face of the housing to prevent contact with the ear of the user when the earphone is seated in the ear of the user to reduce corrosion of the charging connector of the earphone, reduce dirt buildup, and/or improve comfort.

The earphone may include a controller that includes a processor, a memory, and a surface area of the controller. The earphone may also include a touch sensor set in the outside face of the housing configured to detect the finger of the user and produce a control signal for generation of a control input. The touch sensor may be positioned in an exposed region of the outside face such that the touch sensor is accessible to the finger of the user without being blocked by a tragus and/or an anti-tragus. The earphone may also include a first magnet of the earphone positioned on the outside face and configured to magnetically couple the outside face of the housing to a first magnet of a charging interface of a charging device to align the charging connector of the earphone with a charging connector of the charging interface of the charging device.

The earphone may include a boot surrounding the housing and including a first opening for a nozzle of the earphone directing sound into the ear canal of the ear and a second opening exposing the outside face of the earphone. The boot may further include an inside surface of the boot that faces inward toward the concha and contacts at least a portion of the concha to reduce dirt buildup and/or improve comfort.

The earphone may include an antenna electrically coupled to a network interface controller for transmitting and/or receiving an audio signal and/or data. The antenna may include a portion of the antenna following a portion of a periphery of the outside face. The first magnet of the earphone and/or the charging interface of the earphone may be located on the outside face opposed to the portion of the periphery to reduce an RF interference with the first magnet of the earphone and/or the charging connector of the earphone. The portion of the periphery may be located within the exposed region and opposite, across the outside face, an intertragic notch when the earphone is seated in the ear to reduce the RF interference with the ear and/or the finger.

The earphone may include a plate of the housing that includes an exterior surface of the plate and an interior surface of the plate. The exterior surface of the plate may include the outside face of the housing. The antenna may be conductively traced on the interior surface of the plate along the portion of the periphery to conserve the surface area of the controller and/or improve RF signal of the antenna. The plate may be injection molded and a conductive trace may be engraved on the interior surface of the plate through laser direct structuring (LDS). The portion of the antenna may be a majority of a linear distance of the antenna and/or a collection area of the antenna. The earphone may also include a microphone that is audibly coupled to a microphone port that may be set in a central zone of the outside face of the earphone usable to detect and/or record an environmental sound.

The earphone may include a directional locking engine stored on the memory. The directional locking engine may include computer readable instructions that when executed: (i) receive the control signal from a touch sensor of a first earphone generated by activation of the touch sensor, (ii) receive from an accelerometer of the earphone (physically fixed relative to the outside face) a first acceleration data that may include a positive acceleration indicating a direction of gravity, (iii) determine a direction of the touch sensor relative to the direction of gravity; and/or (iv) determine whether to generate the control input from the control signal based on criteria that may include the direction of the touch sensor relative to the direction of gravity, to reduce a probability of a false positive of the control signal while the user is engaged in a resting position.

The earphone may include a physiological feature detection engine stored on the memory that may include computer readable instructions, that, when executed (i) receive from an accelerometer of the earphone an accelerometer signal over a time period that may include one or more acceleration events; (ii) store the accelerometer signal as an acceleration data for the time period in a computer readable memory; (iii) receive an audio signal over the time period from a microphone that may include two or more audio events; (iv) store the audio signal as an audio data in the computer readable memory; (v) overlay the acceleration data and the audio data for the time period; (vi) determine a correlation between two or more acceleration events and the two or more audio events over the time period; and (vii) extract two or more physiological indicators matching the correlation of the two or more acceleration events and the two or more audio events over the time period, to reliably determine a physiological indicator for determining physiological features.

The earphone may include a retainer configured to assist in retention of the earphone in the ear of the user. The retainer may include a member extending outward from the housing and forming an arc fitting curling upward within a fold of an anti-helix of the ear when the earphone is seated in the ear. The touchable surface of the touch sensor may be at least partially bounded by the anti-helix of the ear, the tragus of the ear, and the anti-tragus of the ear.

The earphone may also include a second magnet of the earphone configured to magnetically couple the outside face of the housing to a second magnet of the charging interface of the charging device, the first magnet of the earphone and the second magnet of the earphone rotationally constraining the earphone to align a charging pin of the earphone with a charging pin of the charging interface of the charging device. The charging connector of the earphone may be the charging pin of the earphone and the charging connector of the charging interface of the charging device may be the charging pin of the charging interface of the charging device.

The earphone may include a vibrational control engine stored in the memory that may include computer readable instructions that when executed receive a first acceleration data that may include a vibration signal of the earphone and compare the first acceleration data to a first acceleration signature that describe vibration of the earphone when the finger of the user moves across the touch sensor and/or the outside face of the earphone. The vibrational control engine may also include computer readable instructions that when executed determine whether to generate the control input based on criteria that may include a match between the first acceleration data and the first acceleration signature to reduce a probability of the false positive of the control signal while the user is engaging in rest.

The earphone may include an anatomical control engine stored in the memory that may include computer readable instructions that when executed receive a second acceleration data that may include a recoil signal of the earphone, and compare the second acceleration data to a second acceleration signature that describes acceleration of the earphone when pressed by the finger of the user against an anatomical element of the ear and then released. The anatomical element of the ear may include the tragus, an intertragic notch, the anti-tragus, the anti-helix, a scapha, a cymba conchae, a cavum conchae, and/or an anterior crus of a helix. The anatomical control engine stored in the memory may also include computer readable instructions that when executed determine whether to generate the control input from the control signal based on criteria that may further include a match between the second acceleration data and the second acceleration signature to reduce a probability of the false positive of the control signal while the user is engaged in a resting position.

The touch sensor and the charging connector of the earphone, the first magnet of the earphone, and/or a microphone port may be coextensive on the outside face of the earphone to assist the user in positioning the finger to provide the control input through tactile feedback.

The concha of the user may be solely contacted by a material of the boot when the earphone is seated in the ear. The ear of the user may be solely contacted by the material of the boot and/or a material of the retainer when the earphone is seated in the ear.

In another embodiment, a method for identifying a control input of a user includes receiving a control signal from a touch sensor of a first earphone generated by activation of the touch sensor. The first earphone may include a housing having an outside face that faces outward when the first earphone is seated in an ear such that at least an exposed region is unobstructed to a finger of the user. The method receives from an accelerometer of the earphone physically fixed relative to the outside face a first acceleration data that may include a positive acceleration indicating a direction of gravity, determines a direction of the touch sensor relative to the direction of gravity; and determines whether to generate the control input from the control signal based on criteria that may include the direction of the touch sensor relative to the direction of gravity, to reduce a probability of a false positive of the control signal while the user is engaged in a resting position.

The method may determine that an axis extending perpendicularly through a surface of the touch sensor includes a directional component at least partially pointing toward the direction of gravity. The method may determine that an axis extending perpendicularly from a plane parallel to the exterior surface is less than or equal to a 45-degree angle from the direction of gravity. The method may also determine that the axis extending perpendicularly from a plane parallel to the exterior surface is less than or equal to a 45-degree angle from the direction of gravity.

The method may receive a second acceleration data that may include a recoil signal of the first earphone, and then compare the second acceleration data to a first acceleration signature that describes acceleration of the earphone when pressed by the finger of the user against an anatomical element of the ear and then released. The anatomical element of the ear may include a tragus, an intertragic notch, an anti-tragus, an anti-helix, a cymba conchae, a cavum conchae, and/or an antihelical fold of a helix. It may then be determined whether to generate the control input from the control signal based on criteria further including a match between the second acceleration data and the first acceleration signature to reduce the probability of the false positive of the control signal while the user is engaged in the resting position.

The method may receive a third acceleration data that may include a vibration signal of the first earphone, and may then compare the third acceleration data to a second acceleration signature that describes vibration of the earphone when the finger of the user moves across the touch sensor and/or the outside face of the earphone. The method may determine whether to generate the control input from the control signal based on criteria that may further include a match between the third acceleration data and the second acceleration signature to reduce the probability of the false positive of the control signal while the user is engaging in rest.

The method may determine the match between the second acceleration data and the first acceleration signature, determine the match between the third acceleration data and the second acceleration signature, and generate the control input from the control signal. The control input may include a play instruction, a pause instruction, a skip track instruction, a volume instruction, a masking mode instruction, a sleep check instruction, a transparency mode instruction, and/or a locking instruction. The touch sensor may include a resistive sensor, a capacitive sensor, a pressure sensor, a surface acoustical wave sensor, and/or an infrared sensor.

The method may determine a first earphone of a pair of earphones is facing downward, disable a microphone of the first earphone and/or a touch sensor of the first earphone, determine a second earphone of the pair of earphones is facing upward, and/or enable a microphone of the second earphone and/or a touch sensor of the second earphone.

In yet another embodiment, a device for detecting physiological features of a user includes a processor, a memory, an acceleration agent, an audio agent, an audio-motion overlay routine, an overlay correlation routine, and a physiological indicator extraction routine. The acceleration agent may include computer readable instructions that when executed receive from an accelerometer of an earphone and/or an inertial measurement unit of an earphone an accelerometer signal over a time period that may include one or more acceleration events, and then may store the accelerometer signal as an acceleration data for the time period in a computer readable memory. The audio agent includes computer readable instructions that when executed receive an audio signal over the time period from a microphone that may include two or more audio events, and store the audio signal as an audio data in the computer readable memory. The audio-motion overlay routine may include computer readable instructions that when executed overlay the acceleration data and the audio data for the time period.

The overlay correlation routine includes computer readable instructions that when executed determine a correlation between two or more acceleration events and the two or more audio events over the time period. The physiological indicator extraction routine that may include computer readable instructions that when executed extract two or more physiological indicators matching the correlation of the two or more acceleration events and the two or more audio events over the time period, to reliably determine a physiological indicator for determination of a physiological feature.

The acceleration data may include a description of the inhaling and exhaling of the user. The audio signal may include audio of a sound of the user inhaling and exhaling. The physiological indicator may include a respiration event. The physiological feature includes a respiration rate. The earphone may include the microphone and the microphone may be an external-facing microphone. The acceleration data may also, or alternatively, include a description of the beating of a heart of the user. The physiological indicator may include a heartbeat. The physiological feature may include a heart rate. The earphone may include the microphone and the microphone may be an internal-facing microphone.

The device may further include computer readable instructions that when executed determine an amplitude of one or more frequency bins within the audio data over the time period, sum the amplitudes of each of the one or more frequency bins, apply a peak detection algorithm to determine one or more peaks over the time period, and/or match one or more peaks to two or more acceleration events.

The device may include a physiological feature determination routine that may include computer readable instructions that when executed determine the respiration rate of the user based on the one or more acceleration events over the time period. The device may also include a cognitive state determination module that may include computer readable instructions that when executed determine a cognitive state of the user based on the respiration rate. The cognitive state may include an awake state, a pre-sleep state, a sleep state, a REM state, and/or a NREM state.

The device may include a gyroscope agent and/or an audio-motion overlay routine. The gyroscope agent may include computer readable instructions that when executed receive from a gyroscope of the earphone a gyroscope signal over the time period that may include one or more axis rotation events, and store the gyroscope signal as a gyroscope data for the time period in the computer readable memory. The audio-motion overlay routine may include computer readable instructions that when executed overlay the gyroscope data with the acceleration data and/or the audio data for the time period. The overlay correlation routine may include computer readable instructions that when executed determine over the time period the correlation between two or more axis rotation events and any one of (i) the two or more acceleration events and (ii) the two or more audio events.

BRIEF DESCRIPTION OF THE DRAWINGS

The embodiments of this disclosure are illustrated by way of example and not limitation in the figures of the accompanying drawings, in which like references indicate similar elements and in which.

Other features of the present embodiments will be apparent from the accompanying drawings and from the detailed description that follows.

DETAILED DESCRIPTION

Disclosed are a method, a device, and/or system of an earphone having increased comfort through external-facing charging connections, enhanced controls through direction and/or motion evaluation, and/or accurate physiological feature extraction through audio-motion sensor correlation. Also disclosed are a method, a device, and/or a system of increased comfort, attractiveness, and/or reliability of an earphone such as an earbud through an external-facing charging interface. Also disclosed are a method, a device, and/or a system of enhanced earphone control through directional detection and/or motion signature detection. Still further disclosed are a method, a device, and/or a system of accurate physiological feature extraction through audio data correlated with motion data collected with an earphone sensor.

Although the present embodiments have been described with reference to specific example embodiments, it will be evident that various modifications and changes may be made to these embodiments without departing from the broader spirit and scope of the various embodiments.

Figure 3:
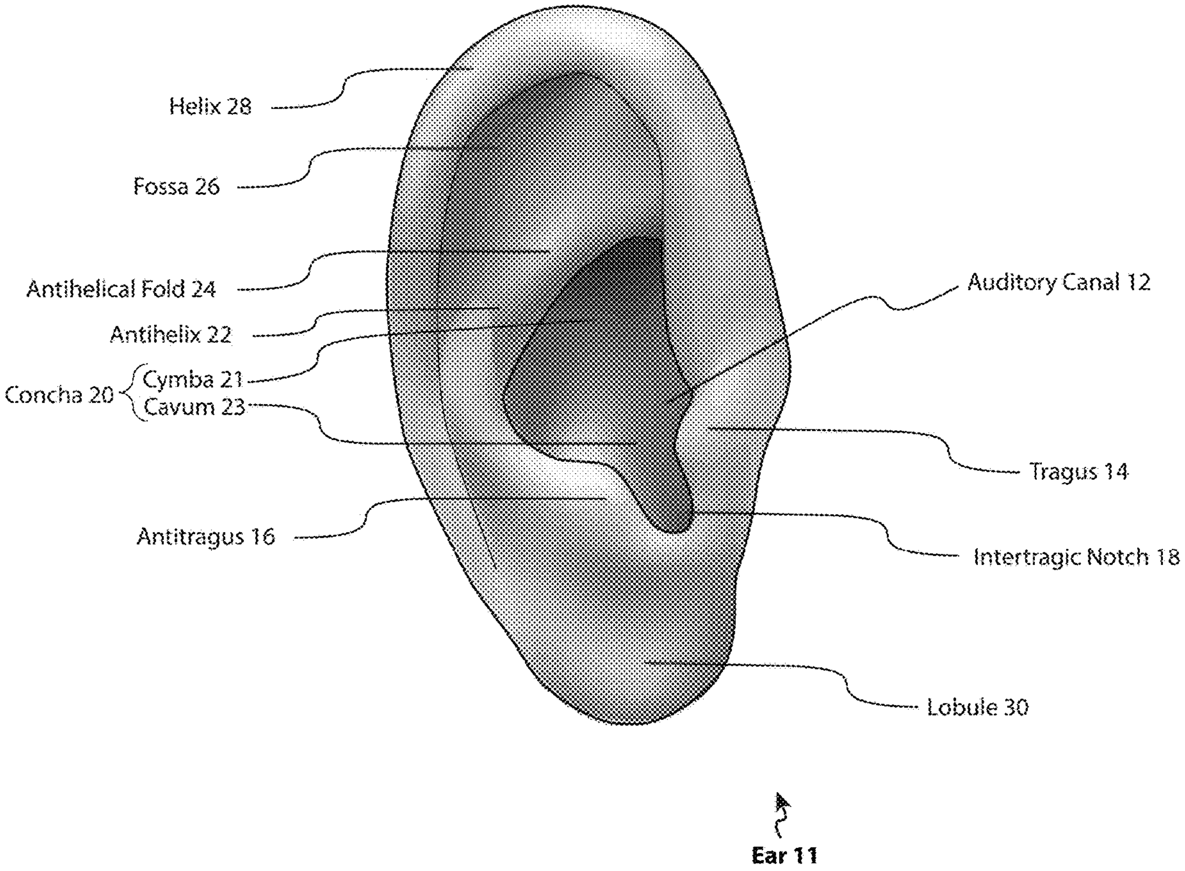
FIG. 3 illustrates anatomical elements of an ear, partially for ease of reference herein, according to one or more embodiments.

Earphones containing speakers that convey audio to the ear canal of the user may be most comfortable when they are small and lightweight. The ear canal is also known as, and will be referred to herein as the auditory canal 12, as shown in FIG. 3. Earphones include over-ear headphones, on-ear earphones, in-ear earphones, and/or clip-on earphones that may otherwise attach to the ear 11. However, one form of preferred earphone that is potentially the smallest and lightest may be an earbud, which may be mounted within and/or held in place by the ear canal itself, including through ergonomic, form-fitting design. Earphones, and particularly earbuds, may be a type of device where condensed design, especially of interior components, can have a significant effect on fit and comfort and therefore monetary value in the marketplace.

Earphones may be used for a variety of purposes, for example streaming music, acting as a two-way communication interface for a mobile device, amplifying sound within an environment for a user 10, and/or reducing sound within an environment for the user 10. One intended use and/or design of earphones that may be benefit from being wireless, small, and light may be earbuds intended for aiding in sleep, for example by producing masking sounds, active noise cancelation, and/or playing soothing audio tracks, etc. This use case for aiding sleep may especially benefit from wireless, small, and/or light design because users 10 may move considerably in their sleep and/or may prefer different sleeping positions. For example, some users sleep on their side, forcing pressure against the car and/or earphone, while other users may move around in their sleep such that an earphone that protrudes from the car may catch and may be dismounted.

The smallest and lightest type earphones may be those that are wireless, for example that include their own wireless communication capabilities and are powered through a battery. Many earphones utilizing a battery may include an internal battery that can be recharged, which may lower cost to the user (e.g., no need to purchase single-use batteries) and therefore represent a competitive advantage in the marketplace, reduce mechanical complexity and weight (e.g., no need to include an opening compartment), may allow for use of custom batteries matching the power and other needs of the earphone, and/or other advantages known and/or that will be evident to those skilled in the art. However, inclusion of an internal battery may require that the earphones will need to be periodically charged. Although induction charging is possible, such components may take up additional precious space, especially in an earbud form factor. Induction charging may also be relatively slow and/or introduce components that interfere with other critical parts, such as wireless communications. Therefore, earphones may include external charging connections of a conductive material, generally metal. This charging connection also may be referred to as electrical leads and/or charging pins, which allow for charging of the internal battery.

Because earphones, and especially earbuds, are small and sometimes ergonomic, for example having smooth curvature, it can be challenging to design a charging interface that provides power to the earphones. At the same time, some earphone designs seek to benefit from a power interface that also includes its own battery. The battery of the power interface can store power then transfer the power to the battery of the earphones. The charging device can be instantiated as a charging case can also help protect the earphones being that some earphones, and especially earbuds, may be small and relatively delicate. Similarly, the charging case may help keep earphones or earbuds in a single location such that they do not get lost or misplaced.

A common strategy, especially for an earphone case and/or charging station, may be to define an inverse shape matching a portion of the earphone and/or earbud, forming a mating surface. This may allow for the earphone and/or earbud to be friction-fit and/or retained through the closeness of the shape and the inverse shape. In many cases, the portion of the earphones that may be selected for the inverse shape mating surface may be an internal-facing portion, that is, the portion of the earphones that faces internally toward the ear and/or ear canal when actively worn and/or mounted within the ear. This internally-facing design may naturally separate magnets and/or electrical leads from RF equipment on the circuit board, and may leave other "real estate" on the exterior open, for example that could be used for gestural input sensors.

However, the charging connections may be uncomfortable when contacting the skin and/or may corrode over time due contact with sweat and other moisture in and around the ear. As a result, earphones may degrade over time, losing the ability to charge and/or form an electrical connection to the charging interface. Charging connections may be uncomfortable, especially if pressure is applied against the charging connections during sleeping and/or other activities (e.g., wearing hats or caps that extend over the ears). Charging connectors may also include small gaps or transitions between materials (e.g., plastic and metal) which can collect dirt, dead skin, and/or earwax, lowering comfort and/or attractiveness of the earphone. In addition, because of the small form factor of earphones and/or earbuds, charging connections may require wiring to a circuit board on the exterior of the earphones for wireless connection purposes.

Such electrical connections could be subject to disconnection, lowering lifespan and/or reliability of the earphones. Therefore, there is a continuing need for improved charging connections for wireless, battery-driven earphones, such as earbuds.

One of the present objectives is to define an earphone and/or an earbud (e.g., the earbud 100) with an externally facing charging interface and/or externally facing charging connections. Another of the present objectives is to overcome one or more challenges that may occur when defining externally facing charging connections, including where the earbuds 100 include other features requiring space on the externally facing side, for example a microphone, wireless antenna, and/or touch sensors.

Figure 4:
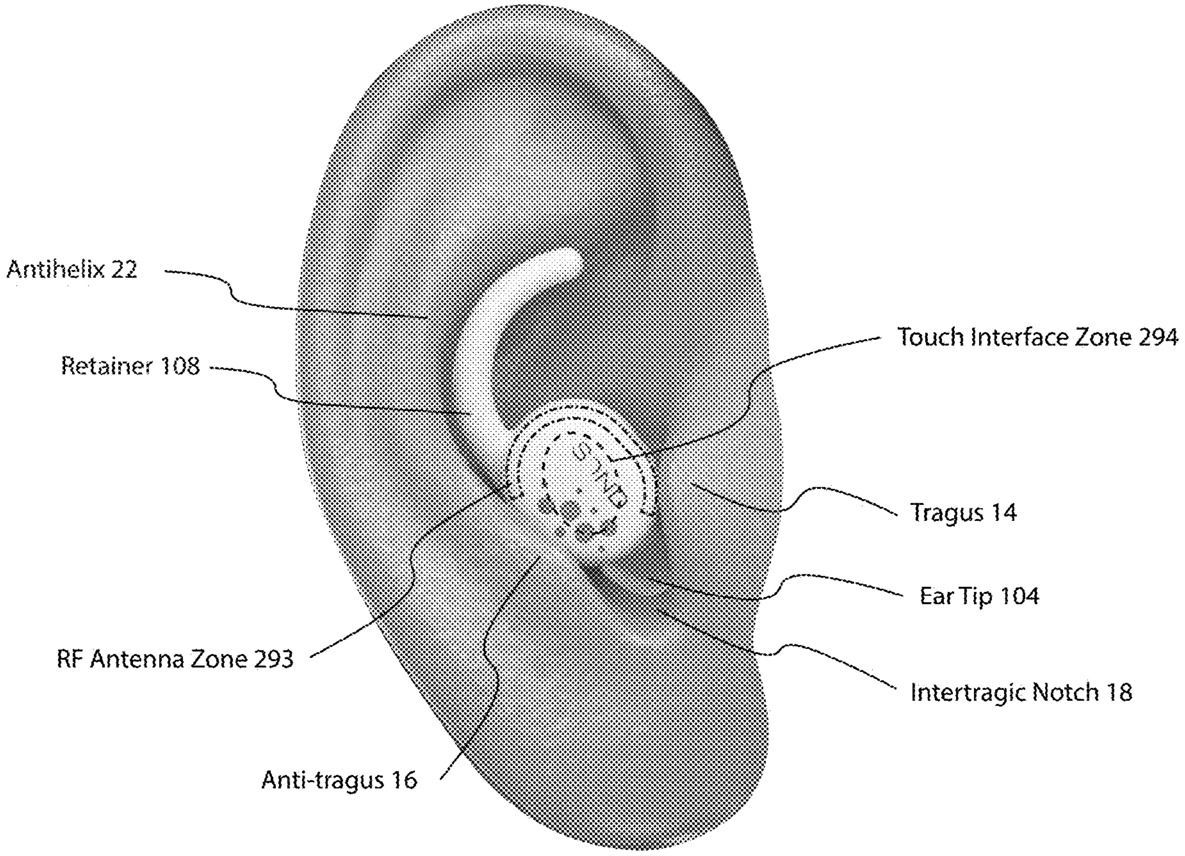
FIG. 4 illustrates the earphone of FIG. 1 mounted in the ear of a user, including illustration of advantageous exposure of the touch interface zone and the RF antenna zone of FIG. 2.
Figure 15:
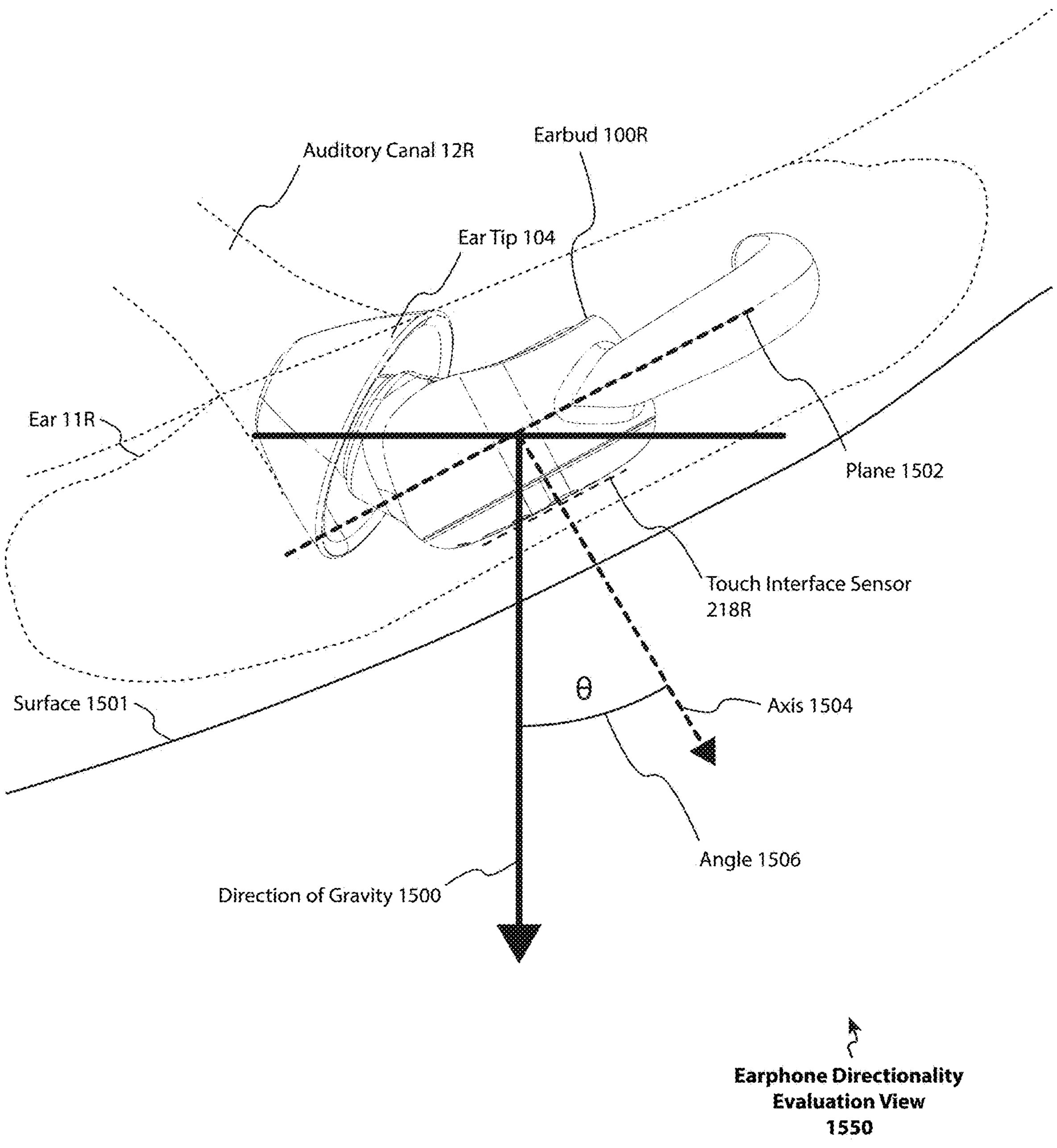
FIG. 15 illustrates an earphone directionality evaluation view usable to evaluate control signals to lock input and/or prevent false positives, especially as may be useful to prevent false positives while utilizing the earphones for sleeping, according to one or more embodiments.

In one or more embodiment, an earphone, and specifically embodied as an earbud 100 (and as may include the earbud unit 200), is defined with an external-facing charging interface 101, for example that includes an exterior-facing charging connector 204 and optionally a ground connector 206. At least one of the charging connectors 204 (e.g., also referred to as charging leads and/or charging pins) in the external-facing charging connection faces away from the ear 11 of the user 10, for example as shown in FIG. 4 and FIG. 15. The ground connector 206 may also face away. For example, the one or more charging leads may be exposed to outside air when the earbud 100 is mounted and/or positioned in the ear 11 of the user 10, which may help the charging leads to stay dry and dirt-free.

In one or more embodiments, an advantage of the exterior facing charging interface 101 of the earbud 100 is placing the charging pins (e.g., the charging connector 204 and the ground connector 206) and magnets 208 distal from areas of the earbuds 100 that could still touch skin and sweat. This may be especially useful for users 10 having ears 11 with a pronounced tragus 14 and/or antitragus 16 features of the ear 11. In one or more embodiments, an advantage of the exterior facing charging interface 101 is enabling better airflow and evaporation of moisture around the metal charging components, reducing corrosion and therefore increasing reliability. In one or more embodiments, an advantage of the exterior facing charging interface 101 is that shorter connections and/or reduced wiring is required to couple to the circuit board (e.g., the controller 220), which may reduce the need for additional space inside the earbud 100 and/or increase reliability being that fewer connections can fail, especially because, in general, earphones may be frequently dropped or otherwise subject to other physical shock. In one or more embodiments, an advantage of the exterior facing charging interface 101 is that a boot 400 and/or covering of the earbud 100 may have a "window" relocated to an exterior facing portion of the boot 400 (e.g., as will be shown and described in conjunction with FIG. 5B). This may allow a material of the book, which may be relatively soft and comfortable, to remain in contact with the entire ear on the interior-facing (e.g., the concha 20) side while still having enough material for structural integrity of the boot 400, maintaining a shape of the boot 400, and/or ensuring the boot 400 firmly embraces the earbud 100. Removing the interior-facing window (e.g., the opening 406 of FIG. 4A) may therefore increase comfort and also reduce area for collection of wax. In addition, the boot 400 having an exterior-facing window (e.g., the opening 404) may allow for more attractive and/or visually distinct design opportunities (including for industrial design and/or logos that can enhance sales), being that design components can be visible when the earphones are worn. This may also allow for an aesthetically pleasing integration of the charging connectors (e.g., the charging connector 204 and the ground connector 206) with the industrial design as visible from the outside. This may turn a design challenge of hiding electrical components into a design opportunity. For example, there may exist the opportunity to blend the charging connectors and magnets into the industrial design of the earbuds 100 by making it a design feature and part of the design language of the brand (e.g., as shown in FIG. 6A). In one or more embodiments, an advantage of the exterior facing charging interface 101 is that it may be relatively easy to place surface magnets (e.g., the magnets 208) in a way that would achieve proper retention of the earbuds 100 in the charging interface 501 of the charging device 500 (such as a charging station and/or charging case), while still being visually pleasing. In one or more embodiments, an advantage of the exterior facing charging interface 101 is maintaining the integrity of a soft and sleek approach to the earphones' fascia (e.g., allowing for a continuous material of the boot 400, and/or smooth plastic of the earbud 100). As a result, there may be no disruption of otherwise smooth ergonomic surfaces intended for touching skin.

Figure 1:
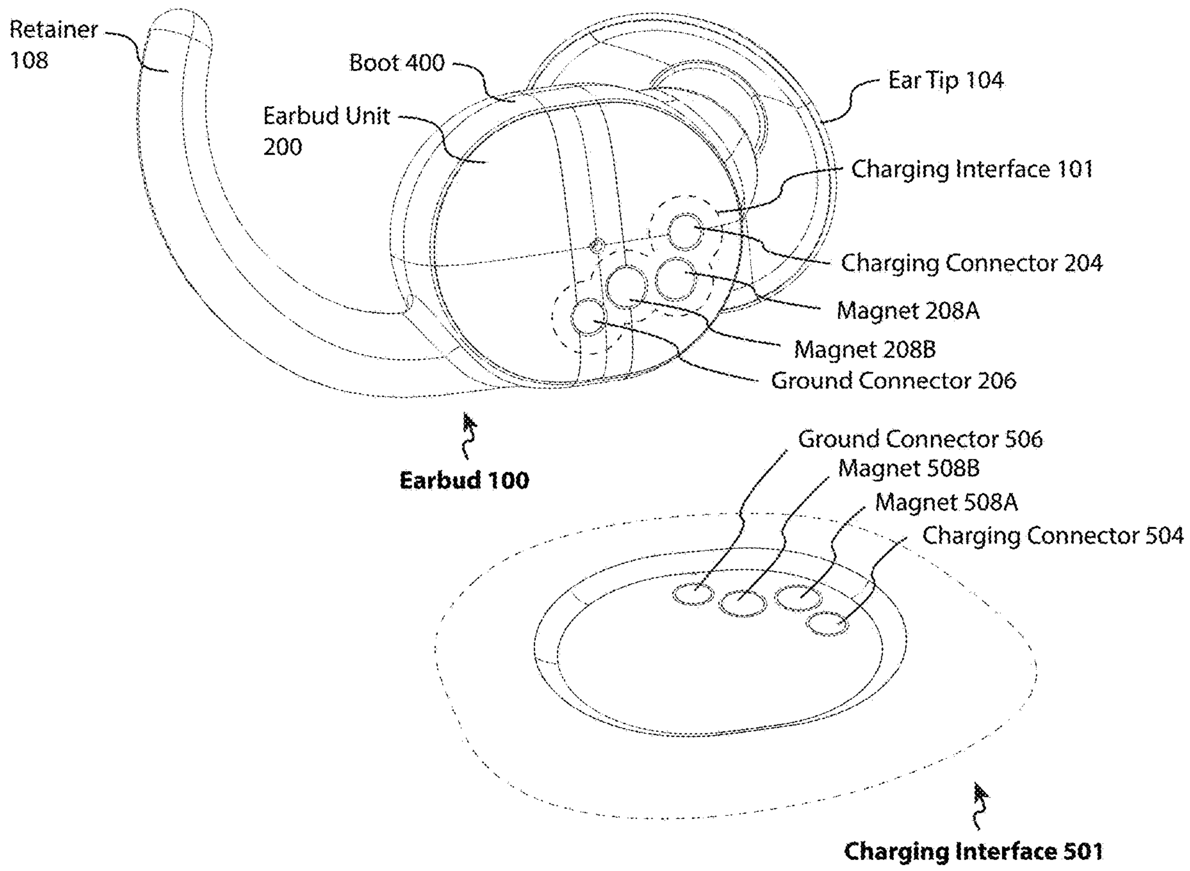
FIG. 1 illustrates an earphone, and specifically an earbud, comprising an external-facing charging interface of the earbud for increased comfort, reliability, and/or durability, the external facing charging interface of the earbud configured to electrically couple to a charging interface of a charger, according to one or more embodiments.

FIG. 1 illustrates an earphone, and specifically an earbud 100, with exterior facing charging connections (e.g., the charging connector 204 and the ground connector 206) and/or magnets (e.g., the magnet 208A and the magnet 208B), according to one or more embodiments. The earbud 100 illustrated in FIG. 1 is a right-side earbud (e.g., for fitting in a right-hand ear 11 of a user 10). The earbud 100 may include an earbud 200 that may hold electronics (e.g., as shown and described in conjunction with FIG. 10 and FIG. 13), a boot 400 a retainer 108, and/or an ear tip 104. Although a boot 400, the retainer 108, and ear tip 104 are shown, and each may be separable according to the embodiment of FIG. 2, FIG. 5B, FIG. 6A, and FIG. 10. Generally, it will be recognized that the earbud 100 may be manufactured as a single piece, that the retainer 108 and the earbud unit 200 may be manufacturing as a single piece, that the ear tip 104 may be removable and/or modular, and/or that the earbud unit 200 and the ear tip 104 may be manufactured as a single piece where the retainer 108 is removable and/or modular.

The earbud 100 may include exterior facing charging connections (e.g., the charging connector 204 and/or the ground connector 206) and/or exterior facing retention magnets (e.g., the magnet 208A and the magnet 208B). In the present example, a charging connector 204 and a charging connector 204B may face outward when the earbud 100 is worn by the user 10. The charging connector 204 and the ground connector 206 may be spaced appropriately to prevent unintended electrical coupling when not charging. For example, the charging connector 204 and the ground connector 206 may be spaced about 3 mm to 1 cm apart on the exterior face of the earbud 16 (e.g., on the exterior plate 205 of FIG. 11). The charging connector 204 may be a positive electrical polarity and the ground connector 206 may be a neutral ground.

Although a single instance of the magnet 208 may be utilized, in one or more embodiments two instances of the magnet 208 may be used to promote and/or require a specific rotational orientation of the earbud 100 within a charging interface 501, thus aligning the charging connector 204 with the charging connector 504 of the charging interface 501 and the ground connector 206 with the ground connector 506 of the charging interface 501. This may further decrease reliance on the complex and/or ergonomic shape of the earbud 100 to hold the earbud 100 in place within the charging interface 501. It may also decrease the reliance on other retention strategies, for example charging connectors or pins that stick out significantly from the earbud 100 into recesses of the charging interface 501, or vice versa.

FIG. 1 further illustrates a charging interface 501 of a charging device 500, such as a wall charger, a charging "dock" that may have a primary purpose of charging the earbud 100, a charging cable that may include the charging interface 501 at one end, and/or a charging case that may protect and/or charge the earbuds 100. As illustrated in FIG. 1, the charging interface 501 may include an inverse shape of the exterior surface and/or charging interface 101. The charging interface 501 may be the mirror image of the charging interface 101. Because the charging interface 101 of the earbuds 100 is externally facing, the complex geometry of the ear tip 104 and/or the retainer 108 may not necessarily interact with the surface in which the charging interface 501 is set, creating a simpler shape which may aid in the manufacturing of the charging device 500. The charging device 500, specifically implemented as a charging case 550, is further shown and described in the embodiments of FIG. 7 through FIG. 9.

The earbud of 100 of FIG. 1 may additionally include one or more sensors and/or functionalities for control input improvement and/or physiological feature determination, as will be further shown and described in conjunction with the embodiment of FIG. 12 through FIG. 22.

Figure 2:
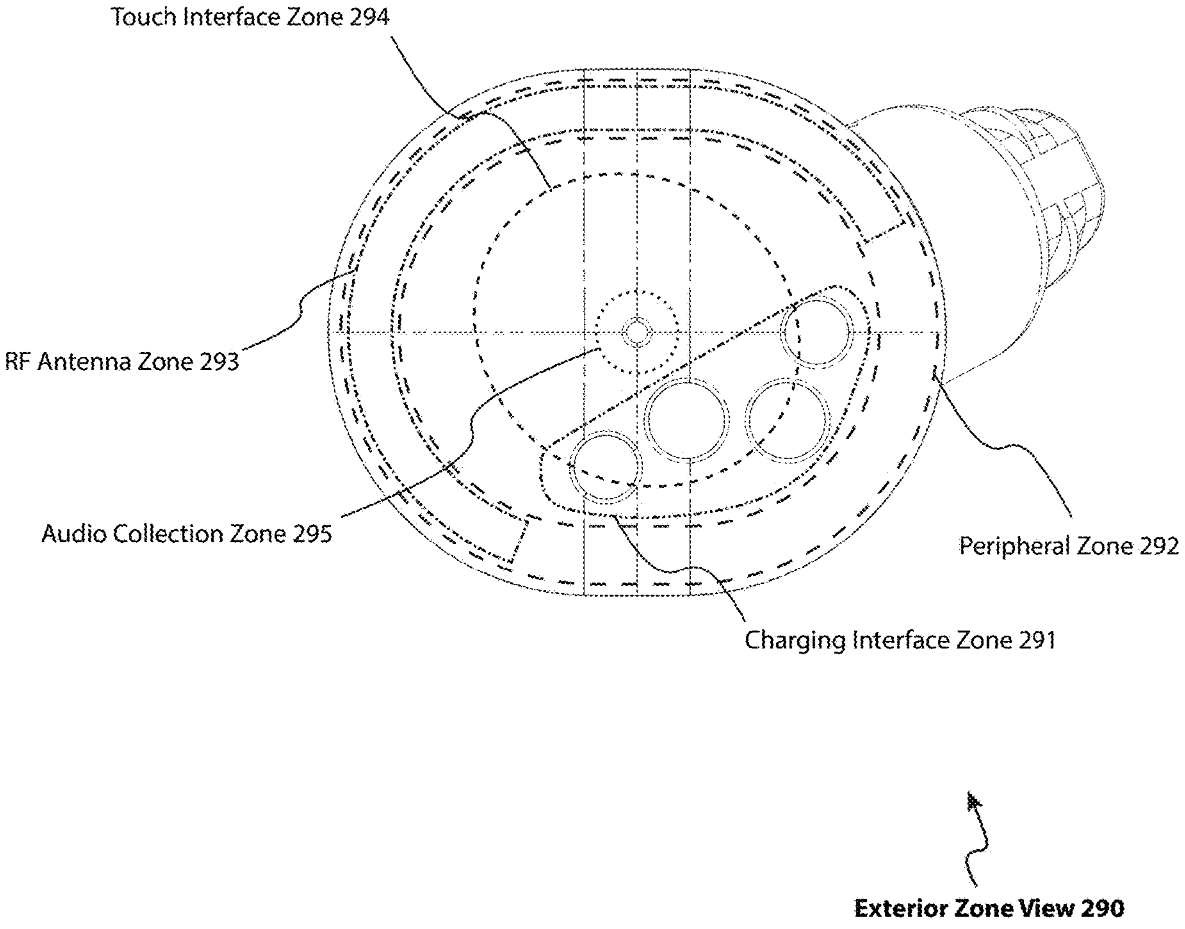
FIG. 2 illustrates an earbud usable as a central component of the earphone of FIG. 1, and the earbud including an exterior zone view showing several zones, one or more of the zones and the allocation thereof optimizing and/or enhancing functionality while maintaining a reduced form factor, the zones including a peripheral zone, a charging interface zone, a touch interface zone, an audio collection zone, and a radio frequency (RF) collection zone, according to one or more embodiments.
Figure 11:
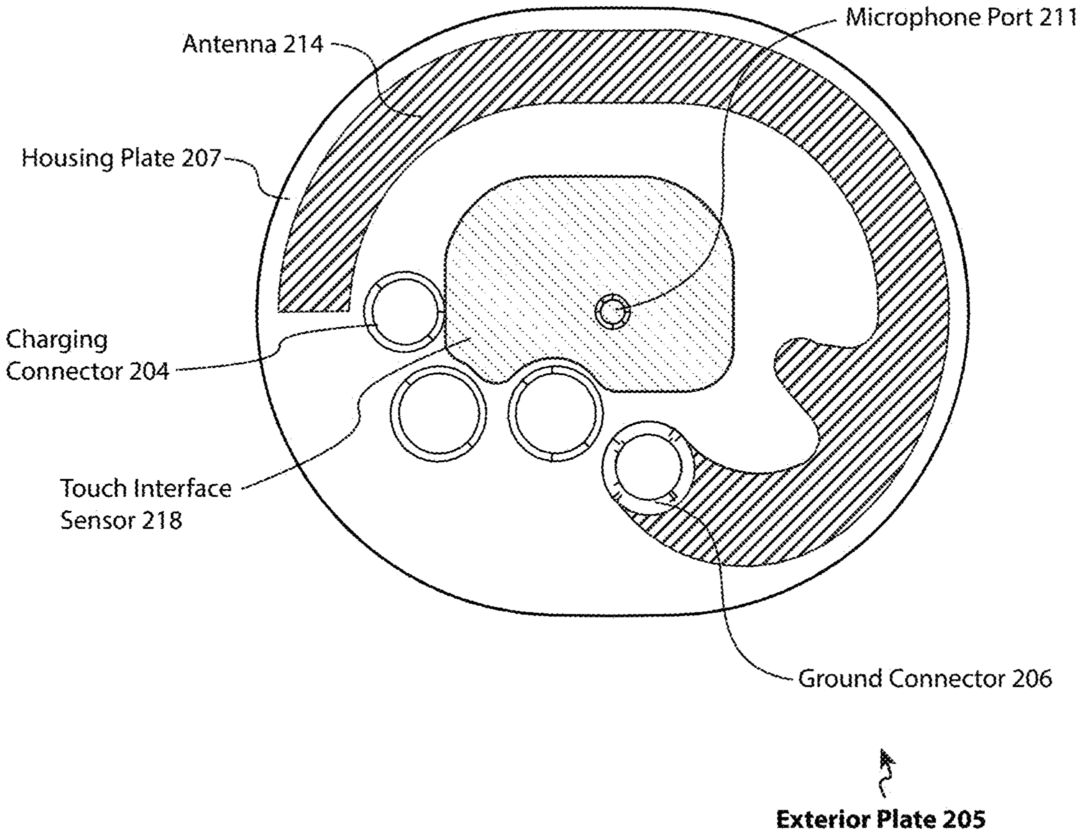
FIG. 11 illustrates a portion of the exterior-facing surface of the earbuds usable to implement the external charging connections and/or one or more of the zones of FIG. 2, and including the location of an electrical trace that may implement the antenna and an electrical trace that may implement touch sensors, the electrical traces depositable on the surface and/or the underside of the surface, according to one or more embodiments.

FIG. 2 illustrates an exterior zone view 290 showing several zones of the exterior of the earbud 100 (and specifically the earbud unit 200 acting as the central component), including a peripheral zone 292, a charging interface zone 291, a touch interface zone 294, an audio collection zone 295, and a radio frequency (RF) collection zone 293, according to one or more embodiments. In one or more embodiments, one challenge in defining earphones and/or the earbuds 100 with an externally facing charging connector 204, ground connector 206, and/or magnets 208 may be coordinating with multiple other components, features, and/or capabilities which otherwise would not need to "share" space on a single surface. As illustrated in FIG. 11, it may be advantageous to carefully coordinate the layout of components to maximize functionality, performance, and/or user experience. For example, an RF antenna (e.g., the antenna 214) usable for wireless communications may experience RF interference, packet loss, and/or other detriment by proximity to the magnets 208 and/or charging connector 204. At the same time, a microphone 212 may be easily blocked by portions of the ear 11 of the user 10 if not centrally located. It may be advantageous for the touch interface to stay out of the peripheral zone 292 where skin of the ear 11 may block access to the finger of the user 10 or result in inadvertent control signals, according to one or more embodiments. In one or more embodiments, there also may be an advantage in orienting and/or positioning the touch interface zone 294 with a direction of a finger of the user 10, e.g., when the user 10 raises the finger to their ear. This orientation may feel more natural to the user 10 and may also increase the amount of contact between the pad of the index finger (or other finger providing a touch gesture intended to generate a control input 242) and the sensing surface (e.g., the touch interface sensor 218). Finally, it also may be an advantage in comfort to try to keep the charging connector 204 and/or magnets 208 away from the peripheral zone 292 where it may come in contact with the ear 11, especially if pressure is applied against the ear 11 during sleeping.

In one or more embodiments, and as shown and described through many of the present embodiments, various zones may be defined to enable two or more of the features to co-exist efficiently and successfully on an exterior facing portion of the earbud 100.

In one or more embodiments, the peripheral zone 292 may be primarily avoided for external interfaces (e.g., the charging interface 101) and/or components, especially because certain users 10 may have a tragus 14 and/or anti-tragus 16 covering all or a portion of the peripheral zone 292. However, the tragus 14 and/or anti-tragus 16 may be sufficiently thin to still permit penetration and/or skirting by RF radiation and/or wireless signals, and therefore may be a candidate for the RF antenna zone 293, as further described below.

The audio collection zone 295 may be centrally located to increase the probability of a clear area for a microphone (e.g., the microphone 212) to collect audio (e.g., the audio signal 231 recordable as the audio data 232) and potentially improve acoustical properties of the microphone 212. Centrality of location may also minimize the feeling of the depression to a finger of the user 10, minimize the probability of skin, earwax, or dirt clogging the microphone port 211, and/or also act as a central tactile guide to help the user 10 know where to place their finger for a successful gesture control movement to result in a control input 241. Similarly, the microphone port 211 and/or other surface features and zones may also act as a tactile guide for providing control input 241 from anatomical element compression and/or recoil as shown and described in conjunction with FIG. 17 through FIG. 19.

The charging interface zone 291 may include the area of the charging connector 204, the ground connector 206, the magnet 208A, and/or the magnet 208B. In one or more embodiments, it should be noted that by allowing the magnet 208A and the magnet 208B to be exposed rather than covered by the housing 206, smaller magnets may be used, therefore saving space within the earbud 100 and reducing potential RF interference. In one or more embodiments, placing the charging interface zone 291 in a lower right hand corner of the exterior face of the right-side earphone 100 (or the lower left hand corner of the exterior face of the left-side earphone, as shown in FIG. 3), but outside of the peripheral zone 292 may represent an advantage. Specifically, the charging connector 204, may result in the ground connector 206 and the magnets 208 may be removed from and/or out of contact of: (i) the antenna 214, and (ii) the skin (e.g., providing more comfort, reducing dirt building or corrosion, and/or providing an aesthetic design opportunity). Such placement may also allow substantial space to remain for the finger of the user 10 to provide touch inputs.

The touch interface zone 294 may be defined for touch inputs by the user 10, and may, for example, comprise one or more touch interface sensors 218 for detection of a human finger. The touch input may result in generation of a control signal 240, and potentially into a control input 241 that initiates one or more control actions by the controller 220. In one or more embodiments, it may be advantageous to prevent overlap of the touch interface zone 294 with the RF antenna zone 293, to reduce temporary RF interference when providing the touch inputs.

The RF antenna zone 293 may be located along an edge opposite to the charging interface zone 291. For example, in one or more embodiments, and as shown in the embodiment of FIG. 2, the RF antenna zone 293 may be located along the top, left-top, and left side of the exterior portion of the right-hand earbud 100R (or the top, left-right, and right side of the exterior facing portion of the left-hand earbud 100L).

As a result of the placement of each zone it may be possible to place exterior facing charging connectors 204 and/or magnets 208 while supporting a number of other features, including touch gestures, wireless communications, and audio collection capability. As a result of the zone layout of FIG. 2, there may be an increased comfort for the user 10, minimization of dirt buildup in recesses, reduced RF antenna interference, ease of touch-sensor access to the fingers of the user 10, and/or unobstructed audio collection that may result in a clearer audio signal.

Figure 10:
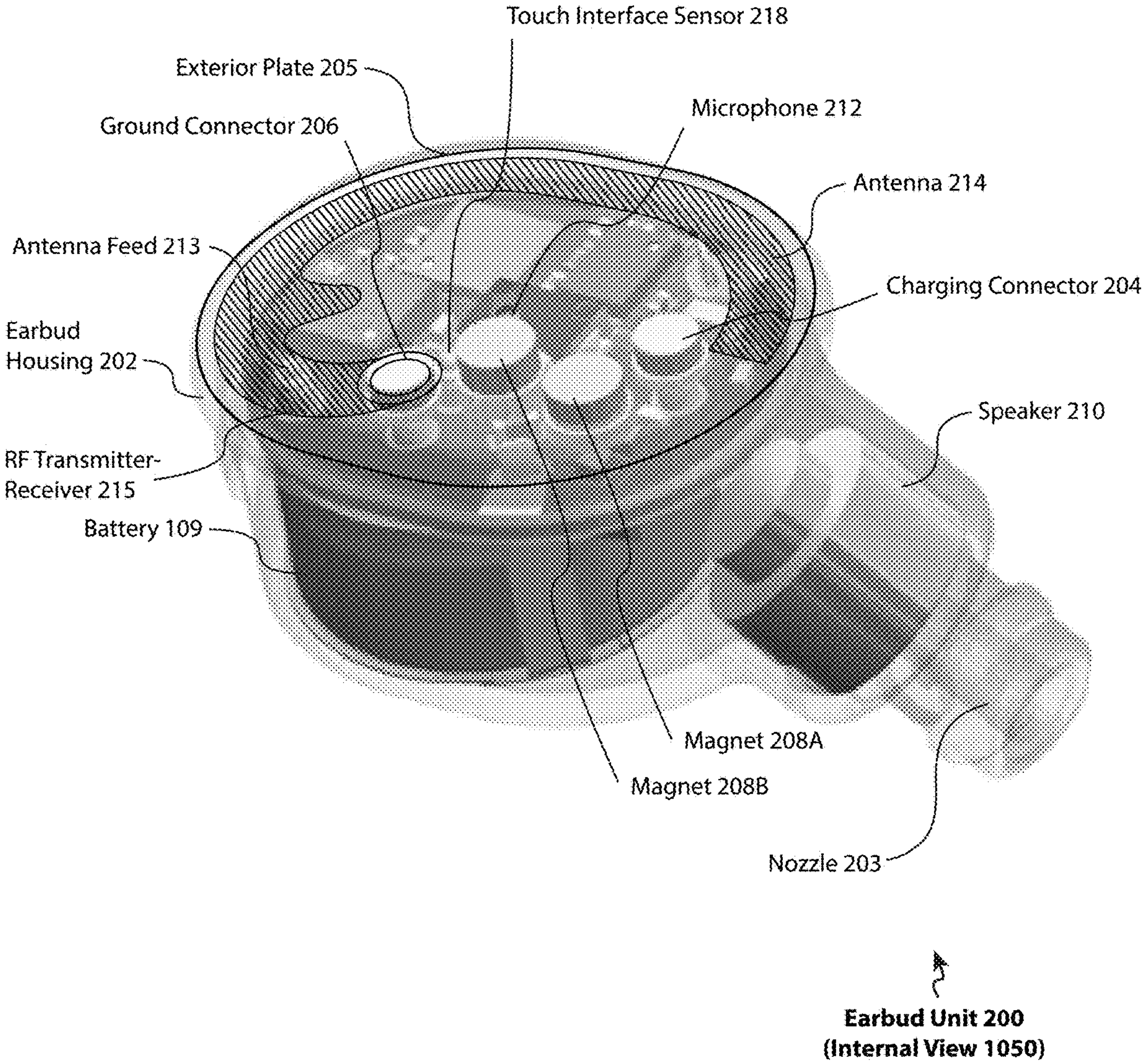
FIG. 10 illustrates an example of the earbud with exterior charging connections and/or magnets, including a housing of the earbud shown in transparency and revealing the circuit board, battery, magnets, microphone, touch interface sensor, and charging connections, according to one or more embodiments.

Implementation of one of more zones of FIG. 2 is further illustrated in the embodiment of FIG. 4, showing fit of the earbud 10 within the ear 11 of the user, FIG. 10 illustrating organization of electrical components within the earbud unit 200, and FIG. 11 illustrating the exterior plate 205.

FIG. 3 illustrates an ear 11 of a user 10, and specifically a right-hand ear 11 which may be referred to as an ear 11R. The ear 11 includes several anatomical elements, including an auditory canal 12 (which may also be referred to as an ear canal), a tragus 14, an antitragus 16, an intertragic notch 18, a concha 20 (including a cymba 21, also referred to as a cumba concha, and a cavum 23, also referred to as a cavum concha), an antihelix 22, an antihelical fold 24, a fossa 26, a helix 28, and a lobule 30. Parts of the ear 11 will be referred to throughout the present embodiments. Unless specifically noted or evident from the context of usage, recitation of an element of the ear 11 may refer to either the left ear 11 (e.g., an ear 11L) or a right ear 11 (e.g., the ear 11R).

FIG. 4 illustrates the earbud 100 mounted in the ear 11 of a user 10. Specifically, the earbud 100 (a right-hand instance, e.g., an earbud 100R) is illustrated seated between the tragus 14 and the antitragus 16, with the retainer 108 curling upward, e.g., substantially vertically and/or along a vertical plane, inside the fold of skin forming the antihelix 22 of the ear 11. The RF antenna zone 293 is illustrated as centrally located and mostly unblocked by the tragus 14 and antitragus 16, improving RF performance. The charging interface zone 291 is illustrated as located away from the skin of the user 10. The touch interface zone 294 is accessible to a finger of the user 10, including a finger reaching ergonomically and/or naturally though the intertragic notch 18 of the ear 11 between the tragus 14 and anti-tragus 16.

Although the earbud 100 is shown including a retainer 108, the retainer 108 may take various shapes, and need not form a crescent or arc shape as shown in several of the embodiments. Other retention mechanisms and/or instances of the retainer 108 may utilize different parts of the ear 11 in order to securely seat the earbud 100. In one or more embodiments, the retainer 108 is optional. For example, the earbud unit 200 with an ear tip 104 installed thereon may be sufficient to seat the earbud 100 securely in the ear 11.

Figure 5A:
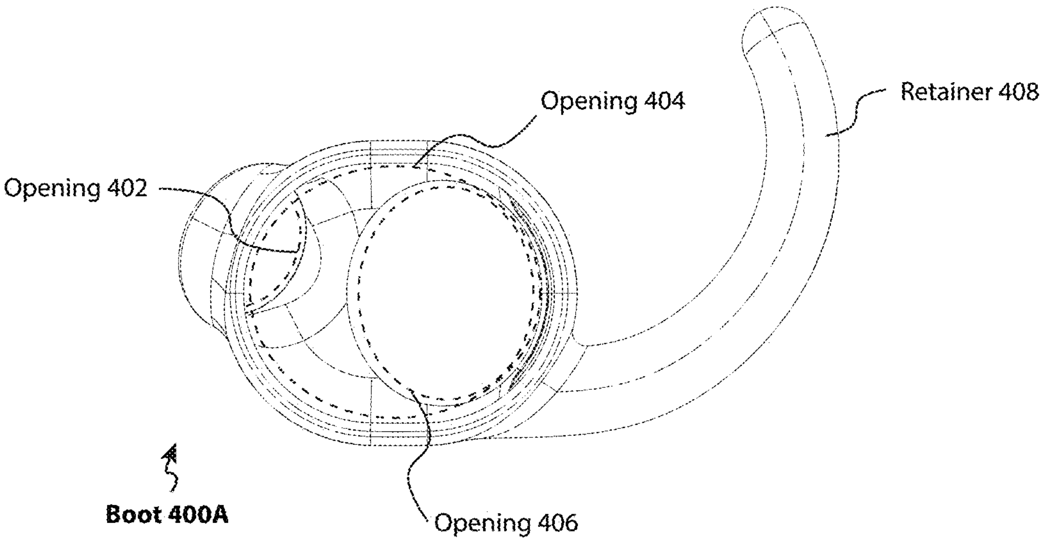
FIG. 5A illustrates a boot for an earbud, the boot including a window for exterior facing charging connections, according to one or more embodiments.

FIG. 5A illustrates a boot 400 for the earbud 100, and specifically a boot 400A, the boot 400A including a window (e.g., the opening 404) for exterior-facing charging connections, microphones 212, and/or touch interface sensors 218, according to one or more embodiments. FIG. 5A illustrates the boot 400A, for example that may be used to encapsulate the earbud 100 of FIG. 2 to form the assembled earbud 100 of FIG. 1 and/or FIG. 6A through FIG. 6C. The boot 400 including the boot 400A may be made of a relatively soft and flexible material (e.g., rubber, silicone rubber, etc.). The boot 400 may include the retainer 108. In the embodiment of FIG. 5A, the retainer 108 may be instantiated as the retainer 408, which may be directly coupled with the boot 400 and/or made from the same or a similar material.

The boot 400 such as the boot 400A may also include one or more instances of an opening. The opening 402 may receive a nozzle 203 of the earbud 100 which carries audio from the speaker 210 to the auditory canal 12 of the user 10. The opening 404 may allow for display of the exterior of the earbud 100, and exposure of the externally-facing charging interface 101 (e.g., the charging connector 204, the ground connector 206 and/or magnets 208) for aesthetic presentation and for electrical and/or magnetic coupling to the charging interface 501, according to one or more embodiments.

Figure 5B:
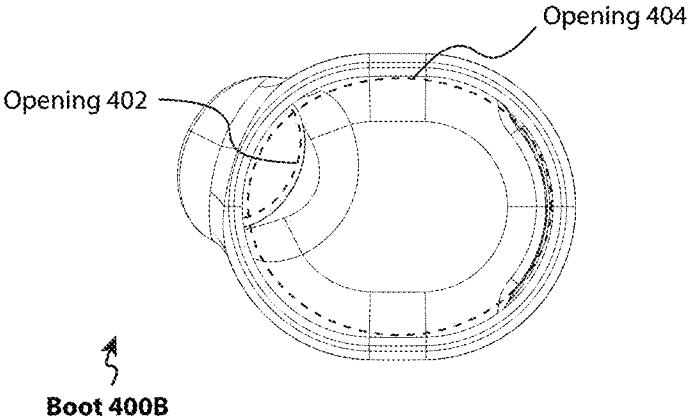
FIG. 5B illustrates another example of a boot for an earbud, the boot increasing comfort and/or reliability by excluding an interior-facing opening that may be otherwise needed for internal-facing charging connectors, according to one or more embodiments.
Figure 6A:
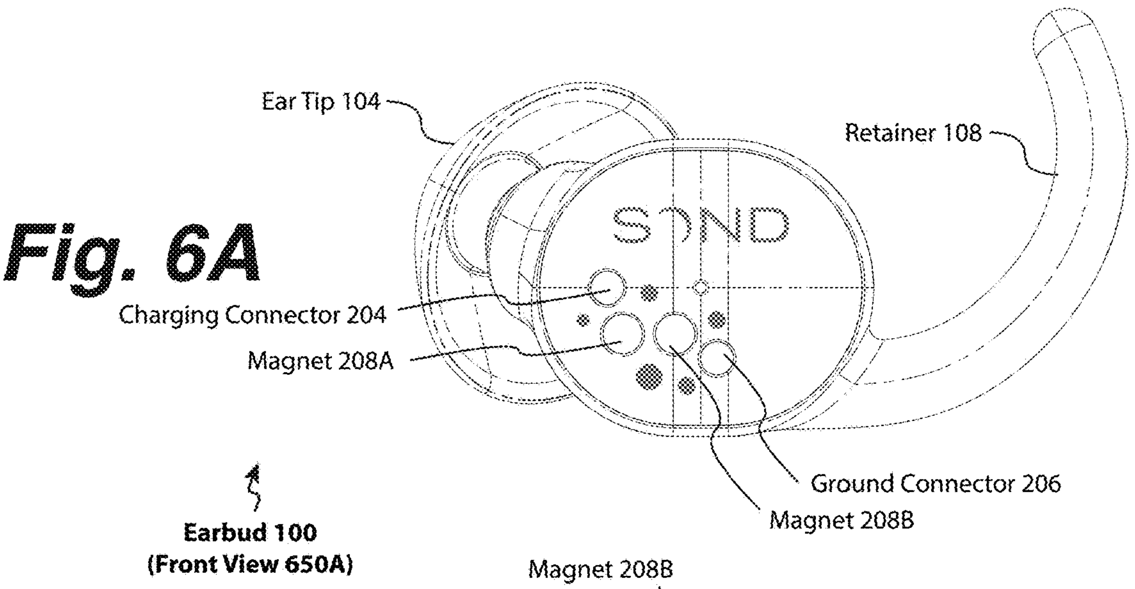
FIG. 6A illustrates the earbud of FIG. 2 installed in the boot of FIG. 5A from a front view, according to one or more embodiments.

The opening 406 is optional and shown for illustrative purposes as an example of an interior-facing window that can be dispensed with once an exterior-facing window is enabled, as further shown and described in conjunction with the embodiment of FIG. 5B.

Although not shown, it will be noted that the ear top 104 also may be integrated into the boot 400, for example integrated into the boot 400A and/or the boot 400B.

FIG. 5B illustrates that the opening 404 may be replaced with solid material of the boot 400 because there is no need to expose charging pins and/or magnets on the interior facing portion of the earbud 100. Dispensing with the opening 404 may additionally increase comfort of the user 10 to feel only a single material touching the skin of the user 10, and/or reduce crevasses that can collect dirt, skin, and/or earwax. FIG. 5B also illustrates an example of the earbud 100 without the retainer 108. For example, in one or more embodiments, the earbuds 100 may comprise an earbud unit 200, a boot 400B, and an ear tip 104, without the retainer 108.

Figure 6B:
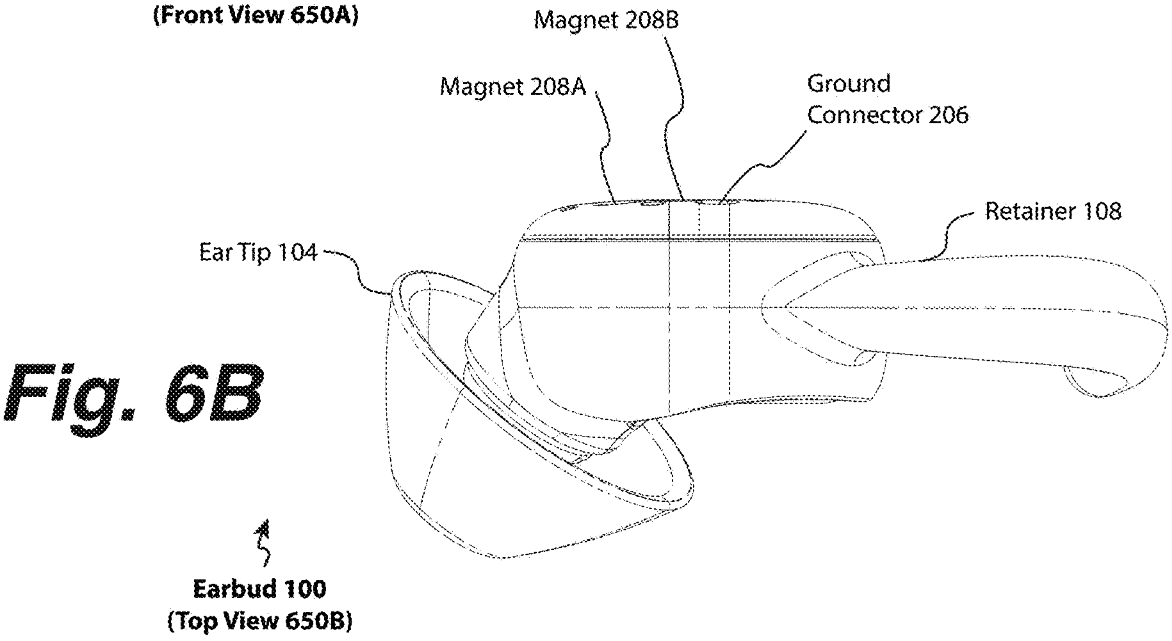
FIG. 6B illustrates the earbud of FIG. 1 from a top view, according to one or more embodiments.
Figure 6C:
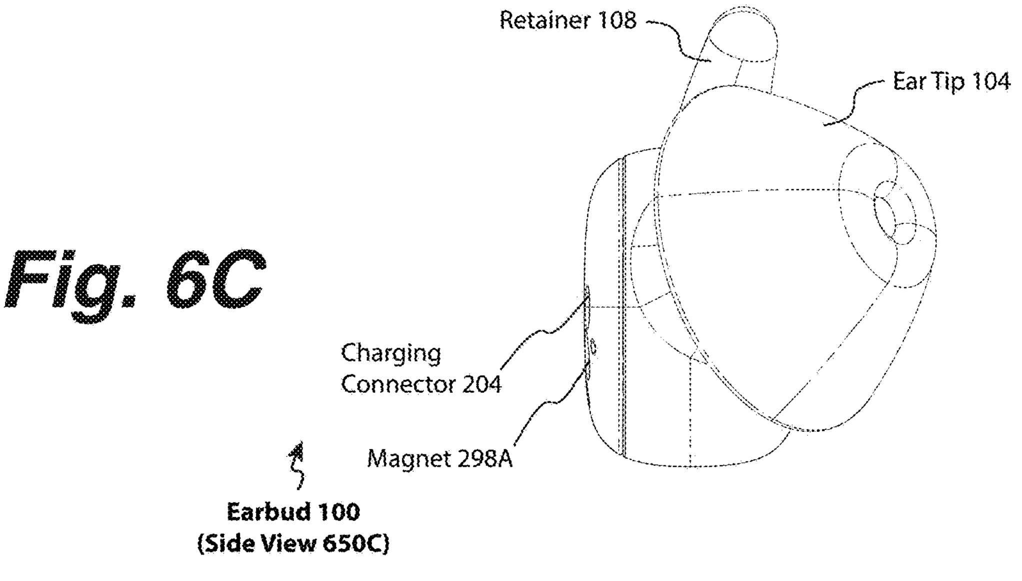
FIG. 6C illustrates the earbud of FIG. 1 from a side view, according to one or more embodiments.

FIG. 6A through FIG. 6C illustrates an assembled earbud 100 comprised of the earbud unit 200 of FIG. 2 installed in the boot 400A of FIG. 5A, and further including an ear tip 104 installed on the nozzle 203 of the earbud unit 200, according to one or more embodiments. The exterior surface of the earbud unit 200, including the charging interface 101 (unlabeled), the microphone port 211, the touch interface sensor 218, and/or the antenna 214, are clearly visible and/or exposed through the window 404 of the boot 400, according to one or more embodiments.

FIG. 6B illustrates the earbud 100 of FIG. 1 from a top view, according to one or more embodiments, and FIG. 6C illustrates the earbud 100 of FIG. 1 from a side view, according to one or more embodiments. FIG. 6B illustrates that, due to the exterior facing charging connectors 204 and/or magnets 208, minimal recesses are required and the charging connectors 204, the ground connector 206, and the magnets 208 may be placed in a relative flat plane which may minimize catching on hats, pillows, sheets, and/or other surfaces, especially if the earbuds 100 are being utilized to assist in sleeping.

Figure 7:
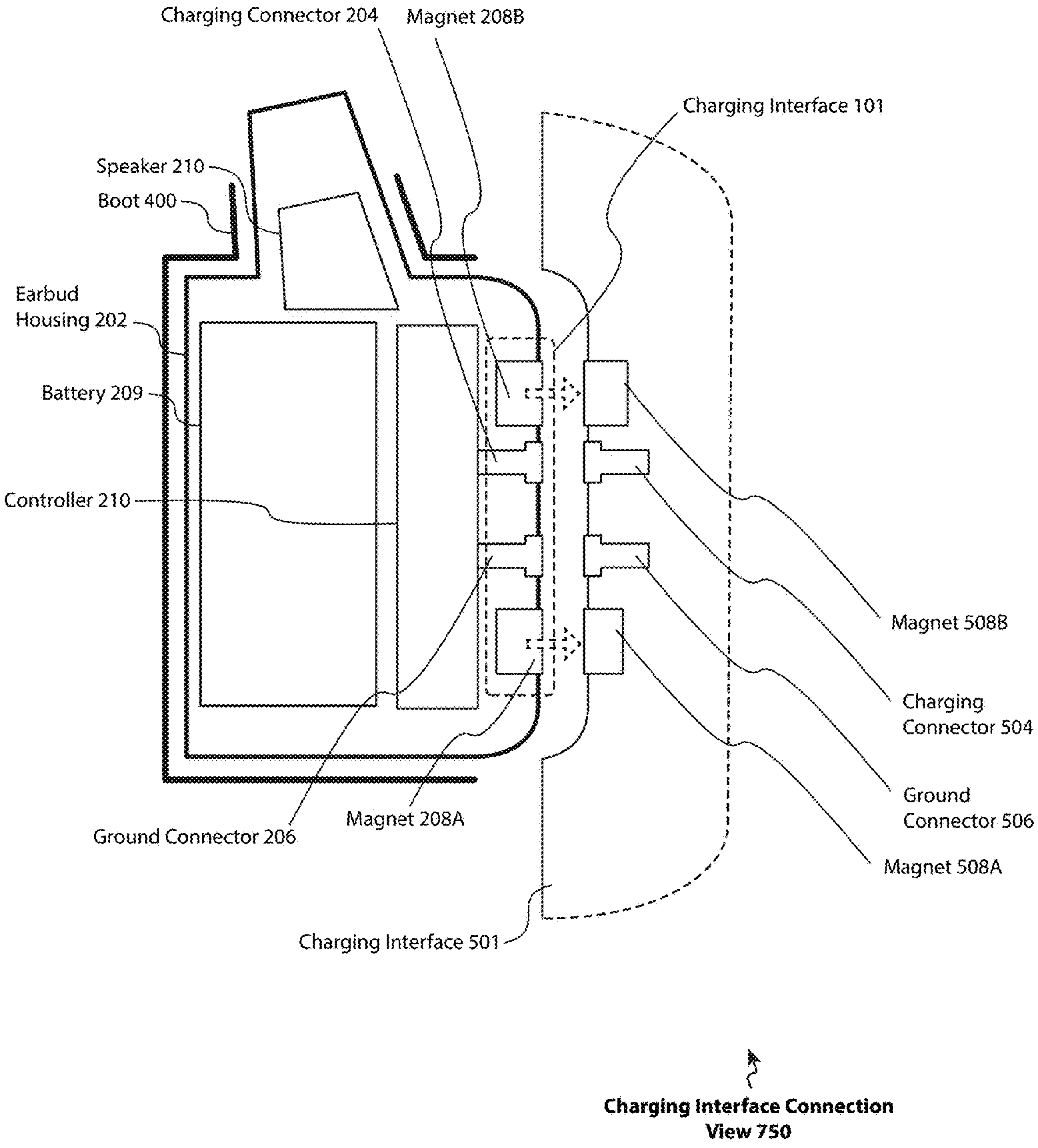
FIG. 7 illustrates an interfacing of an earphone with an exterior facing charging connection and/or magnets with a charging interface of a charging device such as a charging dock and/or a charging case for storing the earphones, according to one or more embodiments.

FIG. 7 illustrates an interfacing of an earphone (such as the earbud 100 of FIG. 1) with an exterior-facing charging interface 101 (e.g., the charging connection 204 and the ground connector 206) and/or magnets (e.g., the magnet 208A and the magnet 208B) with a charging interface 501 such as a charging dock and/or a storage case, according to one or more embodiments. The earbud 100 is shown in a cross-sectional view, including an earphone housing 202 (e.g., a rigid plastic housing) of the earbud unit 200, a boot 400 (e.g., a flexible or semi-flexible boot material), and some of the internal components of the earbud 100 including the battery 209, the speaker 210, and the controller 220. Although not shown, the controller 220 may include one or more circuit and/or logic boards comprising one or more processors, computing memories, charging controllers, audio controllers, and/or other electrical components. The controller 220 and/or its components may be manufactured as a printed circuit board (PCB), and is further shown and described in conjunction with the embodiments of FIG. 10 and FIG. 13). As shown in FIG. 7, the charging connector 204 and the ground connector 206 may be electrically coupled directly to the controller 220 with minimal or no wiring, that is, with a direct, rigid electrical connection onto a circuit board.

The charging interface 501 may be an interface for receiving the earbud 100 and providing the earbud 100 with power, for example to charge the battery 209. The charging interface 501 may be embodied as a charging dock (e.g., a bedside charging dock wired into a wall socket), at the end of a charging cord, and/or within a charging case with a battery that itself can be charged. The charging case 550 may include its own internal battery that can transfer power to the battery 209 when the earbuds 100 are contained therein (for example as shown and described in conjunction with FIG. 8 and FIG. 9).

As additionally shown and described in conjunction with the embodiment of FIG. 1, the charging interface 501 may include one or more magnets 508. For example, the magnet 508 may magnetically couple to the magnet 208A, and the magnet 508 may magnetically couple to the magnet 208B. Similarly, the charging connector 504 may electrically couple to the charging connector 204, and the ground connector 506 may electrically couple to the ground connector 206. In one or more embodiments, the magnets 208 and/or the magnets 508 may include rare earth element magnets, for example neodymium magnets. In one or more embodiments, the magnet 204 and the magnet 204B may be affixed to the earphone housing 102 in inverse polarities (e.g., a '+' side facing out for the magnet 204 and a '−' side facing out for the magnet 204B) to assist in enforcing the orientation. Alternatively, or in addition, and as shown in the embodiment of FIG. 1, the charging connector 204 and the ground connector 206 may be placed such that improper rotational orientation of the earbud 100 will not cause improper and/or unintended alignment of the charging connectors 204 (e.g., the improper electrical coupling of the charging connector 204 with the ground connector 506).

In one or more embodiments, one of the present advantages of an externally-facing charging interface 101 includes the potential for the earbud 10 to be charged while worn, which may be useful if a user 10 is in need of the earbuds 100 but finds they are out of power. A sufficiently lightweight and/or small charging interface 501 on the end of a cord may be utilized for this purpose.

The earbuds 100 may include a minimal and/or symmetric exterior shape of its exterior facing surface (not taking into consideration the charging interface 101 and surface ornamentation), and the charging interface 501 may have a corresponding inverse shape. The relatively simple shape, e.g., a circle or an oval with a beveled edge having C2 rotational symmetry, may decrease complexity, streamline the industrial design, reduce surfacing trapping dirt, and/or increase aesthetics of both the earbud 100 and the charging device 500.

Figure 8:
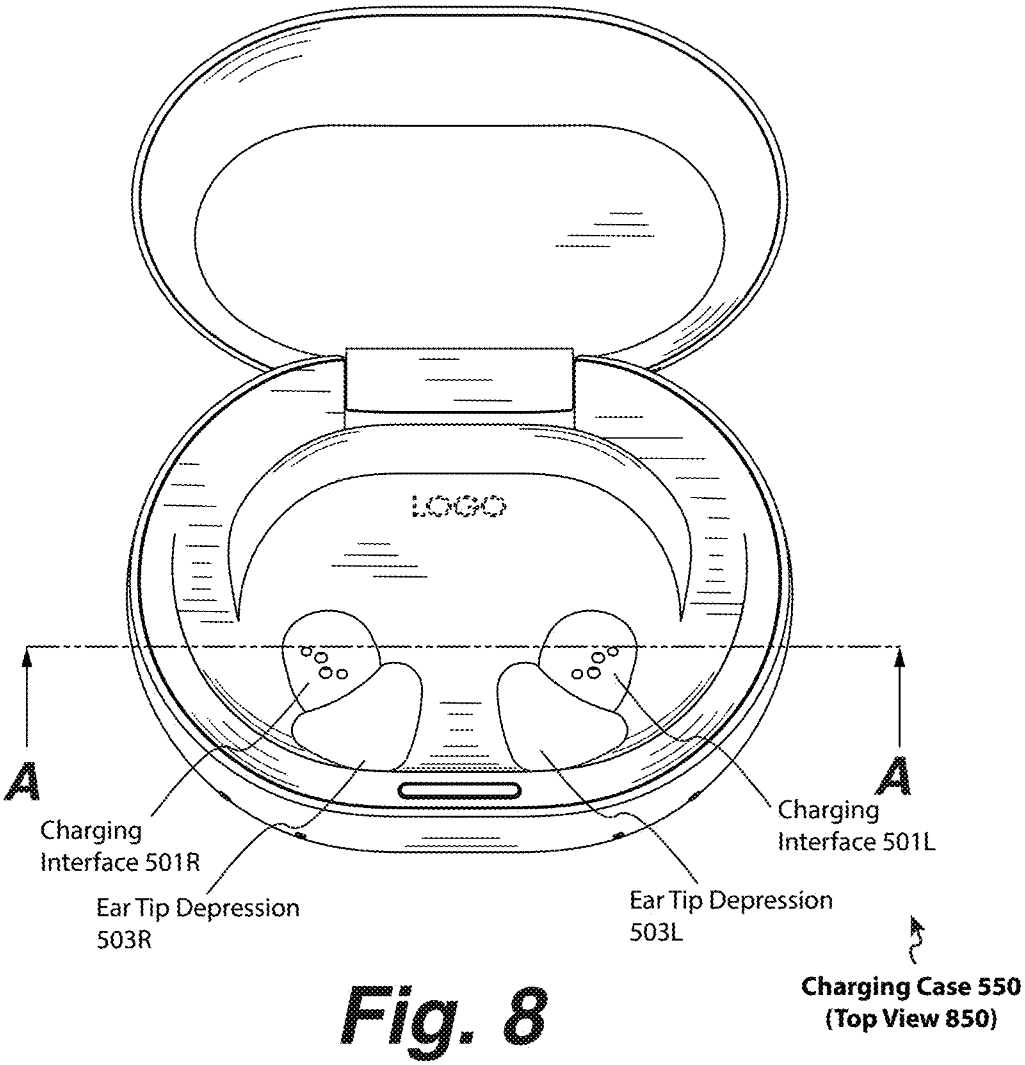
FIG. 8 illustrates a charging case which may receive the earbuds having the exterior facing charging connections, according to one or more embodiments.

FIG. 8 illustrates an example of a charging device 500, specifically embodied as a charging case 550 (e.g., including the charging interface 501) which may receive the earbuds 100 having the exterior-facing charging interface 101, according to one or more embodiments. The charging case 550 illustrates a charging interface 501L for a first earbud 100 (e.g., an earbud 100L fitting the left ear) and a second charging interface 501R for a second earbud 100R fitting the right ear 11R). Although not labeled, the four interfacing points (e.g., the charging connector 504, the ground connector 506, the magnet 508A, and the magnet 508B) are shown for each of the charging interface 501L and the charging interface 501R. For example, the charging connector 504 of the charging interface 501L may be referred to as the charging connector 504-L and the magnet 508A of the charging interface 501R may be referred to as the magnet 508A-R. The charging interface 501R and four illustrated connections and/or magnets match those of the charging interface 501 of FIG. 1 (FIG. 1 also illustrates a right-hand charging interface 501). Although optional, the charging case 550 may include an ear tip depression 503L and an ear tip depression 503R such that the ear tip 104 of each of the left and right earbuds 100 may remain installed when the earbuds 100 are docked for charging. FIG. 8 also illustrates a cross-section 'A' line, the resulting cross-sectional view of which is shown in FIG. 9.

Figure 9:
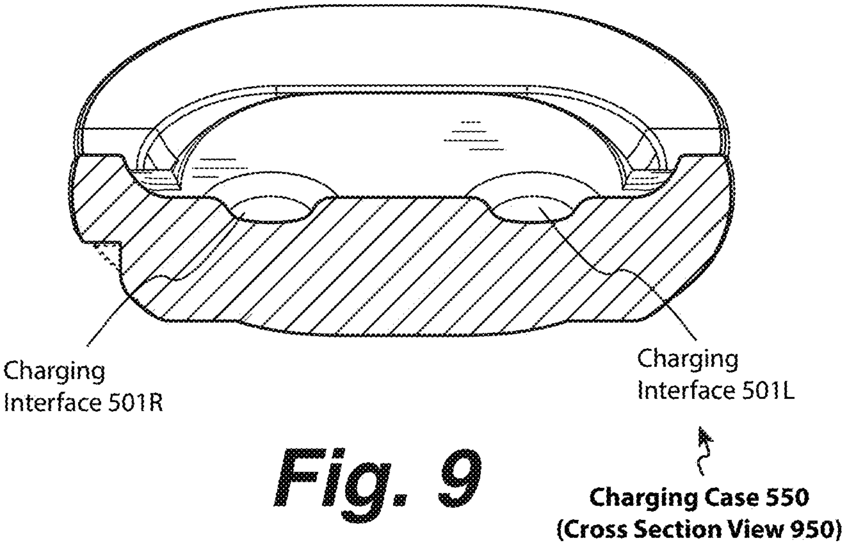
FIG. 9 illustrates the charging case of FIG. 8 in cross-section, showing the mating surface that is the inverse shape of the exterior of the earphone, according to one or more embodiments.

FIG. 9 illustrates the charging case 550 of FIG. 8 in cross-section along the cross-section 'A' line, showing the mating surface that is the inverse shape 31L of the exterior of the earbud 100, according to one or more embodiments. FIG. 9 demonstrates the streamlined shape of the mating surface, which may reduce dirt capture, increase aesthetic appeal, and may be easier to manufacture. The electronic and other components inside the charging case 550 are not illustrated, but may include a power supply, and each of the elements of the charging interface 501 shown and described in conjunction with FIG. 7, and/or other components. The charging device 500 such as the charging case 550 may include additional electronic, processing, and/or communications components, as further shown and described in conjunction with the embodiment of FIG. 14.

FIG. 10 illustrates an example of the earbud 100 with exterior charging interface 101, where an earbud housing 202 of the earbud 100 is shown in transparency to reveal the circuit board (e.g., implementing the controller 220), the battery 209, the magnets 208, the charging connector 204, the ground connector 206, and other components, according to one or more embodiments. FIG. 10 demonstrates, as will be recognized to those skilled in the art, the condensed space available within the earbuds 100, especially for designing earbuds 100 that may be comfortable and/or ergonomic. FIG. 10 further illustrates that the wireless antenna 214 may be positioned toward an exterior of the earbud 100, e.g., positioned under the earphone housing 102 along the exterior-facing surface, for example as shown in FIG. 11. As previously shown and described, this placement may improve wireless transmission and/or communications, for example communication with a network interface controller of a device 60 such as a smartphone (e.g., Bluetooth® connection) and/or charging case 550. The wireless antenna 214 is illustrated with a placement that may be removed from the magnets 208 and/or the charging connectors 204, which may reduce radio frequency (RF) interference and/or improve RF performance, as show and described in conjunction with the embodiments of FIG. 2 and FIG. 11. The antenna 214 may be connected to an RF transmitter-receiver 215 through an antenna feed 213, where the antenna feed 213 may provide a direct connection from the circuit board to the exterior plate 205, according to one or more embodiments. Also illustrated are the speaker 210 configured to supply sound to the nozzle 203, which may be audibly coupled to the auditory canal 12 of the user 10.

A portion of the exterior plate 205 is shown superimposed on the transparency of the earbud housing 202, including a path of the antenna 214, according to one or more embodiments. The exterior plate 205 is further shown and described in conjunction with the embodiment of FIG. 11.

FIG. 11 illustrates a portion of the exterior-facing surface, referred to as the exterior plate 205, of the earbuds 100 (and specifically, a left-side earbud 100L). The exterior plate 205 may be used to implement the external charging connections and/or other zones, for example as shown and described in conjunction with FIG. 2, according to one or more embodiments.

The exterior plate 205 may be implemented with a housing plate 207 that that may fasten onto the remaining portion of the earphone housing 102. Four large through-holes are evident, corresponding to the charging connector 204, the magnet 208A, the magnet 208B, and the ground connector 206, as shown in FIG. 2. Alternatively, or in addition, the through-holes may be replaced with two-way conductive contacts. The two shaded regions illustrated on the exterior plate 205 may illustrate possible placement of an electrical trace and/or conductive coating that may be used to implement the antenna 214 (e.g., the solid oblique shading) and/or the touch interface sensor 218 (e.g., the dotted oblique shading). The touch interface sensor 218 may attach directly to the controller 220 such as the circuit board shown and described in conjunction with FIG. 10. The touch interface sensor 218 may placed be in a central region of the housing plate 207 that is flat and/or uncurved. For example, the touch interface sensor 218 may be placed such that it does not overlap with the peripheral zone 292, but may be partially interspersed with the large through-holes and within the touch interface zone 294, as shown and described in conjunction with FIG. 2. The collection surface of the touch interface sensor 218 may be placed centrally such that the finger of the user 10 may move through the intertragic notch 18 and/or between the tragus 14 and anti-tragus 16 to touch the touch interface sensor 218. In one or more embodiments, placement is such that the exposed touch interface sensor 218 permits enough movement for the user 10 to swipe in two or more directions, for example up (relative to gravity if the user 10 is standing and wearing the earbuds 100), down, left, right, at oblique angles, etc. The collection surface of the touch interface sensor 218 may be optionally co-extensive with the microphone port 211, and may be placed in a central area such that the feeling of the microphone port 211 may provide a tactile guide to center the finger of the user 10 to create a baseline location by which to judge the property interaction with the interface (e.g., to provide effective gestures that result in recognized control input 242). The microphone port 211 may be a through-hole acoustically coupling the exterior environment to the microphone 212. The microphone port 11 may be beveled to prevent catching and/or discomfort when contacting the finger of the skin, and/or catching on pillows or other bedding when side-sleeping.

The ground connector 206 may be electrically coupled to the RF transmitter-receiver 215, for example as shown in FIG. 10. The antenna 214 may follow an outside edge of the housing plate 207, for example within the peripheral zone 292 of FIG. 2. In one or more embodiments, the limited space of the exterior surface of the earphone housing 102, and circuit board below may increase the difficulty in utilizing a chip-based antenna and/or coil-based antennas (especially when combined with one or more other of the present features). Therefore, in one or more embodiments, a conductive trace can be added directly to portions of the earphone housing 102. In one or more embodiments, the conductive trace may be added through laser direct structuring (LDS) directly to an injection-molded plastic of the housing plate 207. The antenna 214 implemented with the conductive trace may increase usable space of the circuit board, allow for a relatively large area for RF collection and/or transmission, even along the curved surface of the peripheral zone 292. The conductive trace antenna 214 may also add greater control in the exact placement of the antenna 214. The conductive trace may be added to an underside of the housing place 207, according to one or more embodiments.

In one or more embodiments, the placement of the RF antenna 214, and its shape, as shown and described throughout the present embodiments, avoids the location of the positive charging terminal (e.g., the charging connection 204) and also may incorporate the ground contact as an integral part of a Planar Inverted F Antenna (PIFA). In one or more embodiments, the PIFA design is optimized to occupy the outer perimeter of the earbud 100 face, serving as a main radiating element. Extensive testing was performed on prototypes to ensure RF performance.

Despite advantages described herein in placing the charging connectors 204 and/or magnets 208 on the exterior facing surface, it also potentially presents several engineering and/or design challenges, each of which may be overcome by one or more of the present embodiments or aspects thereof.

Aesthetic and Ergonomic Challenges: Achieving a curved and seamless look and feel with the charging connectors 204 on the outer-face and/or exterior-facing face of the earphone such as the earbud 100 may present a challenge. For example, traditional designs may benefit from the natural concealment provided by the earphone anatomy facing inward, allowing for a more straightforward aesthetic design. In one or more embodiments, for example as illustrated in FIG. 9, the charging connector 204, ground connector 206, and/or magnets 208 may be hidden within a visual design element.

Space Constraints: The compact nature of earphones, and especially earbuds 100, may limit the available space for components. By placing the charging connector 204 and/or the ground connector 206 on the outer face (e.g., exterior facing portion of the earphone housing 102 and/or the exterior plate 205), a challenge of ensuring the integrity of the antenna and RF performance may occur (e.g., performance of the RF transmitter-receiver 215). This positioning could potentially interfere with these critical components, necessitating innovative solutions to maintain optimal functionality. One solution can include placing the antenna 214 on the opposite side of the earphone housing 102 along the exterior surface of the exterior facing portion of the earphone housing 102. As another possible solution, the antenna 214 may be constructed utilizing a conductive trace deposited in the earphone housing 102, for example through LDS engraving, as shown and described in conjunction with the embodiment of FIG. 11.

Charging Case Alignment: what may be unconventional placement of the charging interface 101 on the exterior of earphones such as the earbuds 100 may add complexity to the interaction with the charging interface 501 of the charging device 500, such as the charging case 550. Ensuring that the charging connector 204 and the ground connector 206 are aligned correctly with the charging connector 504 and the ground connector 206, respectively, while also securely holding the earbuds 100 in place on the charging interface 501, may have encouraged reconfiguration of the placement of the magnets 208 and the magnets 508. In one possible solution, the magnets 208 may be placed proximate to the charging connector 204 and the ground connector 206 (e.g., within a few centimeters), to promote tightly tolerance alignment. In another solution that can be utilized, two magnets 208 may be used (the magnet 208A and the magnet 208B). In yet another solution that is usable, the magnets 208A and the magnet 208B may have inverse polarities facing toward the exterior to help enforce an orientation (e.g., rotational orientation within the inverse shape of the charging interface 501). Another solution can include placing the magnets 208 in an uncovered position within the earphone housing 102 to improve magnet attraction with the charging interface 501, for example protruding through the through-holes illustrated in FIG. 11. Another possible solution includes two or more magnets 208, and/or defining charging connectors 204 without rotational symmetry, to assist in enforcing the orientation and therefore help overcome this challenge.

Gesture Difficulties: The outer face of an earbud 100 may be used for gesture controls, for example where sensors can detect pressing and/or swiping of a finger to generate control inputs 242. The touch interface sensor 218 may include electrostatic potential sensor. The electronic potential sensor may be sensed utilizing an ST Microelectronics® chip. Charging connectors 204 and/or the ground connector 206 on the exterior face may create a challenge in placing and maintaining a touch interface that still allows for intuitive gestural controls due to the limited available space and other component placement constraints. In one possible solution, one or more touch interface sensors 218 and/or collection surfaces of the touch interface sensor 218 may be interspersed between and/or among the charging connector 204 and/or the ground connector 206 (e.g., partially within the charging interface zone 291). A solution may include centrally placing the touch interface zone 294 for receiving a finger of the user 10, and allowing enough space for swipes upward, downward, right, and left, without the finger intercepting, encountering, and/or being blocked by anatomical elements of the ear 11, such as the tragus 14 or anti-tragus 16. In one or more embodiments, a solution can include overlapping a microphone 212 audio collection point (e.g., the microphone port 211) with a collection surface for the touch interface sensor 218. In one or more embodiments, a solution can include overlapping the audio collection zone 295 within the charging interface zone 291, where optionally the microphone 212 may be turned off and/or audio collection thereof turned off when the finger of the user 10 is sensed, for example through the touch interface sensor 218. This may help prevent collection of a loud sound or noisy (e.g., within the audio signal 231) audio that may occur when the user 10 rubs their skin against and/or moves their finger over the microphone 212.

Figure 17:
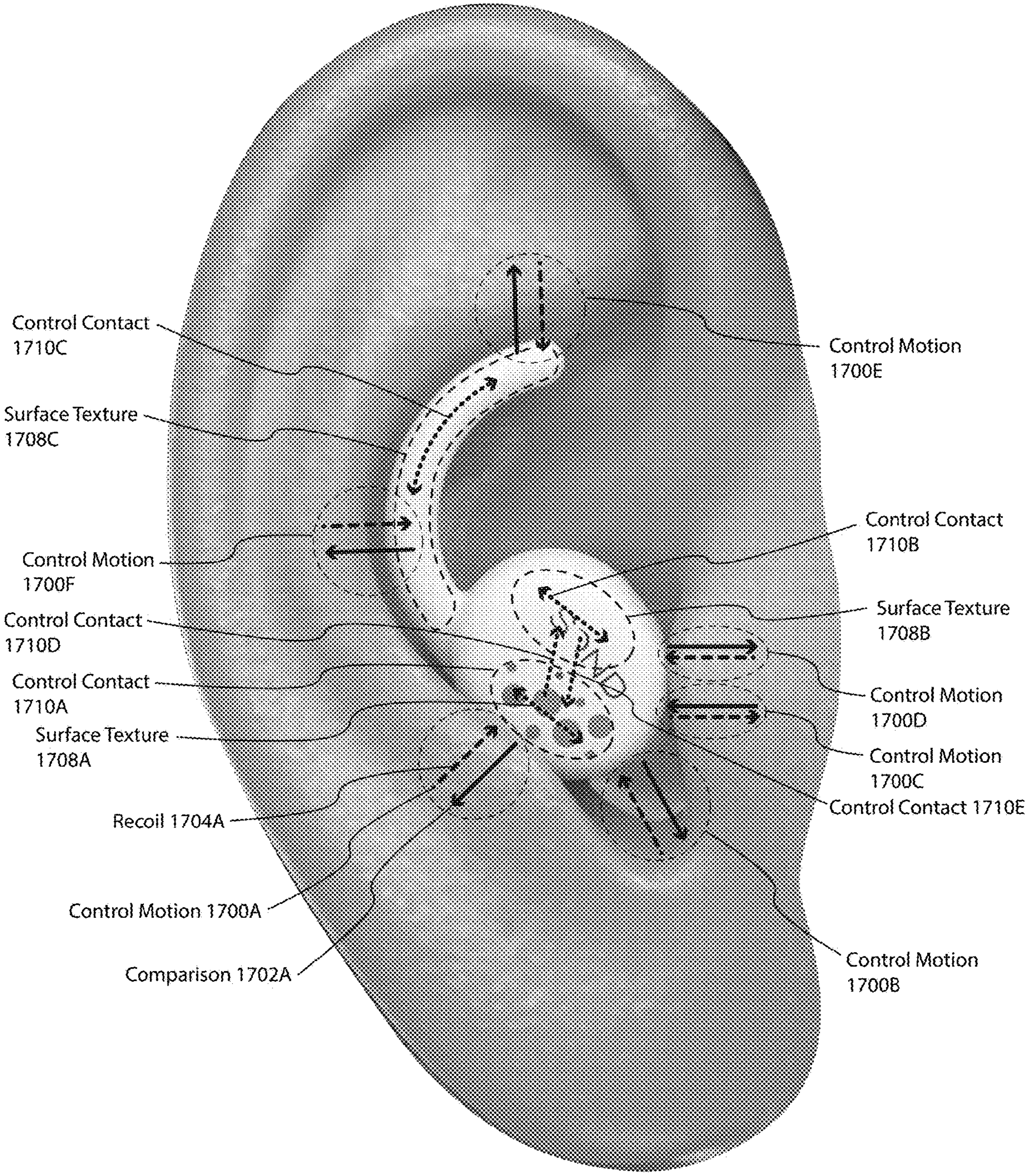
FIG. 17 illustrates an anatomical and vibrational control input view demonstrating, independently and collectively, control inputs provided through compression against and/or recoil from anatomical elements of the ear, and additionally control inputs provided through skin and/or touch interaction with various surfaces and/or surface textures of the earphone causing detectable control signals, according to one or more embodiments.
Figure 18:
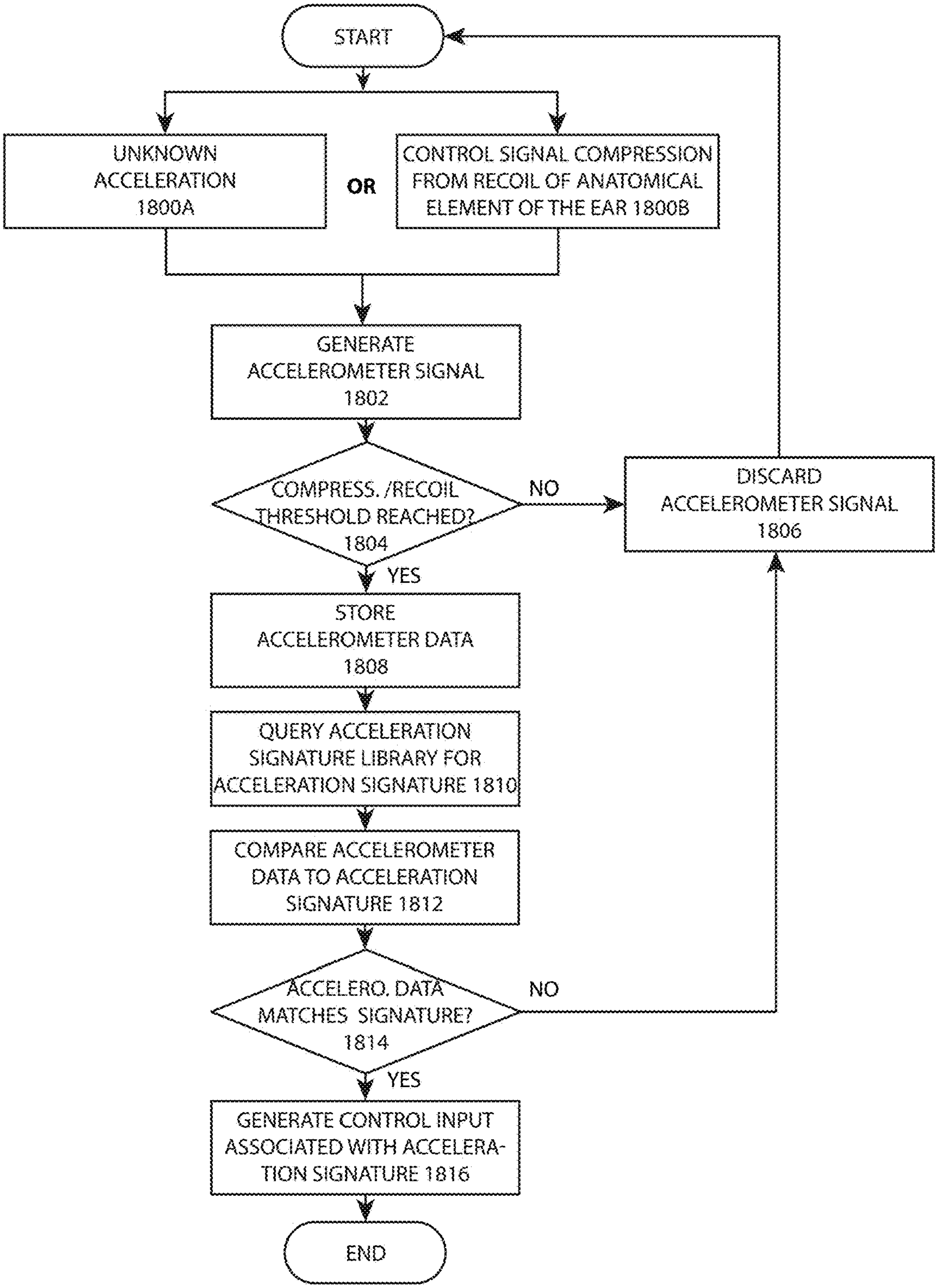
FIG. 18 illustrates an anatomical interaction control process flow for detection of control inputs from compression against and/or recoil from anatomical elements of the ear, according to one or more embodiments.
Figure 19:
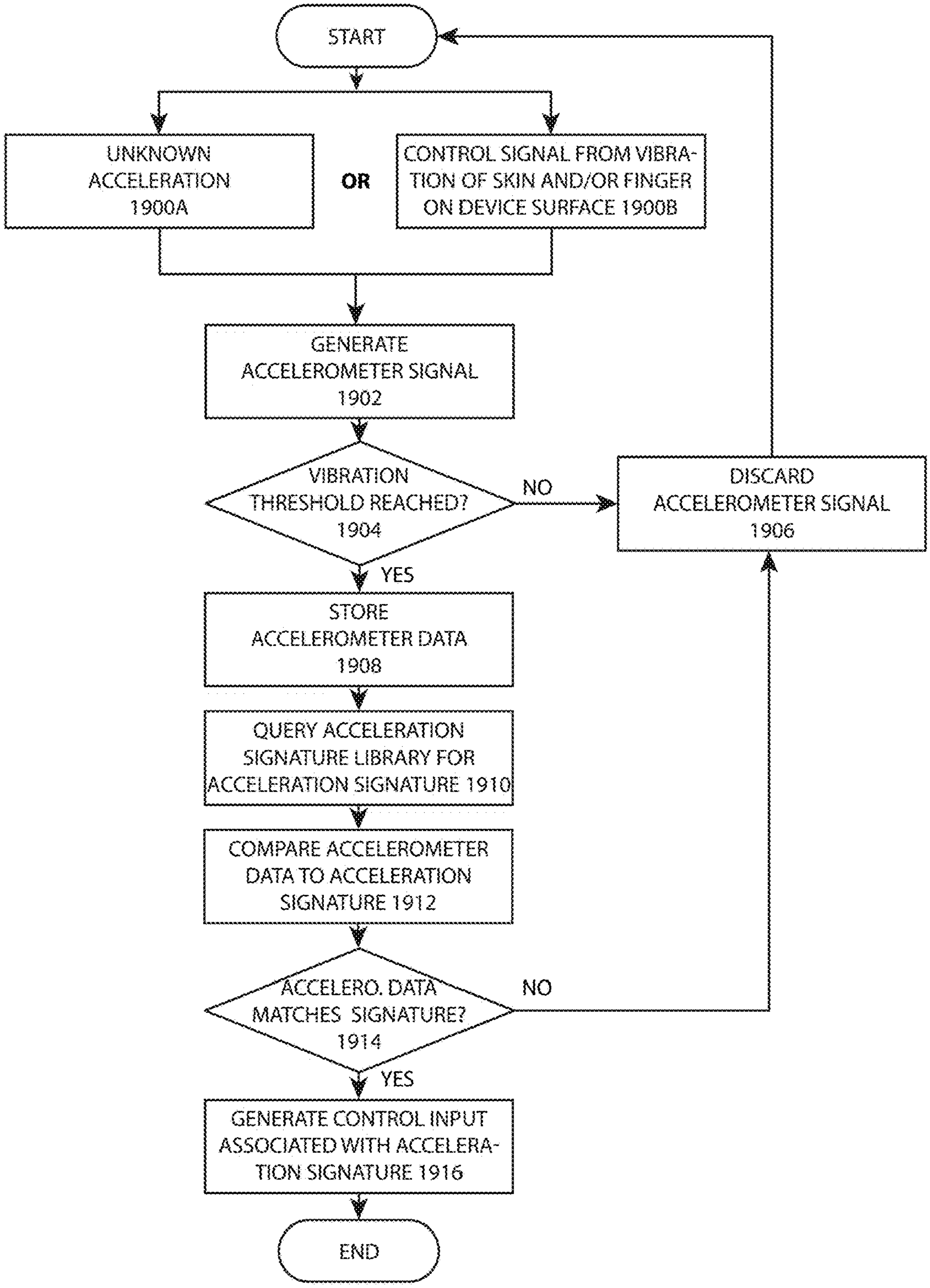
FIG. 19 illustrates a vibration control recognition process flow for detection of control inputs from skin and/or touch interaction with various surfaces and/or surface textures of the earphone, according to one or more embodiments.

Additional solutions to the challenge of having limited surface area for providing control inputs 240 are shown and described in conjunction with the embodiments of FIG. 17 through FIG. 19. These solutions may be utilized as an alternative to, and/or in addition to a touch interface sensor 218.

Although the present embodiments in FIG. 1 through FIG. 11 describe an exterior facing charging interface 101 and/or exterior facing charging connection for an earphone, it will be evident to one skilled in the art that other exterior-facing connections, such as an electrical ground connection and/or a wired data connection, also may be utilized.

FIG. 12 through FIG. 19 illustrate a device, system, and method for evaluating control inputs from a user 10 to reduce false positives, create an expanded UI/UX capability within limited available surface area of earphones, and/or provide new and potentially more accurate forms of generating control input 241. The control input 241, for example, may include a play instruction (e.g., to play a soundtrack or other audio data), a pause instruction, a skip track instruction, a volume instruction, a masking mode instruction (e.g., a sound masking mode), and a sleep check instruction (e.g., a query to ask a sleep tracking system how rested and/or how much the user 10 has slept), a transparency mode instruction (e.g., to allow sound through a sound masking and/or noise canceling system), and/or a locking instruction.

A false positive may be a control signal 250 generated by a sensor, but which was not intended by the user 10 to generate the control input resulting in one or more various control actions to be performed. As just one example, the user 10 may accidentally brush their wrist against the touch interface sensor 218 when attempting to manipulate their hair. In another example, the touch interface sensor 218 may accidentally generate signal input when a user 10 changes position in their sleep and rests their ear 11 (and earbud 100) on their shoulder or upper bicep.

An expanded "control space" is also potentially advantageous. For example, depending on the sensitivity of the touch interface sensor 218, it can be difficult to assign a wide variety of discrete controls to what may be limited detection capability. Highly sensitive touch sensors also may be expensive and therefore cost prohibitive within a competitive consumer marketplace. In one or more embodiments, a simple instance of the touch interface sensor 218 may be able to detect a touch, a touch for a period of time (e.g., a touch and hold), and/or a swipe. In one or more other embodiments, a more sophisticated instances of the touch interface sensor 218 may be able to direct a particular directionality of a swipe, a location of the press on the touch interface sensor, a "touch and roll" in which the pad of the finger is rolled from side-to-side or up-and-down, and/or a depression "pressure" as may be measured by an increased surface area of the skin contact area over time. However, these potential controls may also be difficult for a user 10 to execute on a small earphone, especially if the user has big fingers. Therefore, new and improved methods of generating control input are valuable and advantageous.

FIG. 12 through FIG. 14, and FIG. 20 through FIG. 22, illustrate a device, a system, and a method for accurately determining physiological indicators (e.g., a heartbeat, a respiration event such as a breath), and physiological features (e.g., a heartrate, a respiration rate) from data at least partially generated by a device physically coupled to the user 10 such as earphones like the earbud 100. Determination of physiological indicators and/or physiological features may be useful in a variety of contexts, for example health and fitness, medical monitoring of vital signs, personal health evaluation, and other purposes.

One use of physiological indicators and physiological features relates to evaluation of a cognitive state of the user 10. It may be possible to evaluate cognitive states (e.g., excitement, focus, boredom, lack of attention, etc.). However, in one or more embodiments, cognitive state may be useful for determining a difference between states of wakefulness, for example an awake state, pre-sleep or "drowsy" state, a sleep state, a rapid eye movement (REM) state, and/or a non-rapid eye movement (NREM) state.

For sleep applications, monitoring of sleep state through evaluation of cognitive state may be accomplished through a variety of sensors. However, it may be challenging to evaluate motion sensors because the normal functions of sleep (e.g., rolling over, snoring, sudden changes in breath, sleep talking) may interfere in accurately determining physiological features and therefore cognitive state. A consequence of inaccurately determining cognitive state may be unintended control input (e.g., automatically initiating a wake-up sound track for the user 10), improper data and/or statistics (e.g., incorrectly determining the user 10 slept more or less than intended), and other detriments. It is therefore advantageous to try to define an accurate, reliable, and/or consistent method for determining physiological indicators and/or physiological features that may act as the basis for determining cognitive state.

Figure 12:
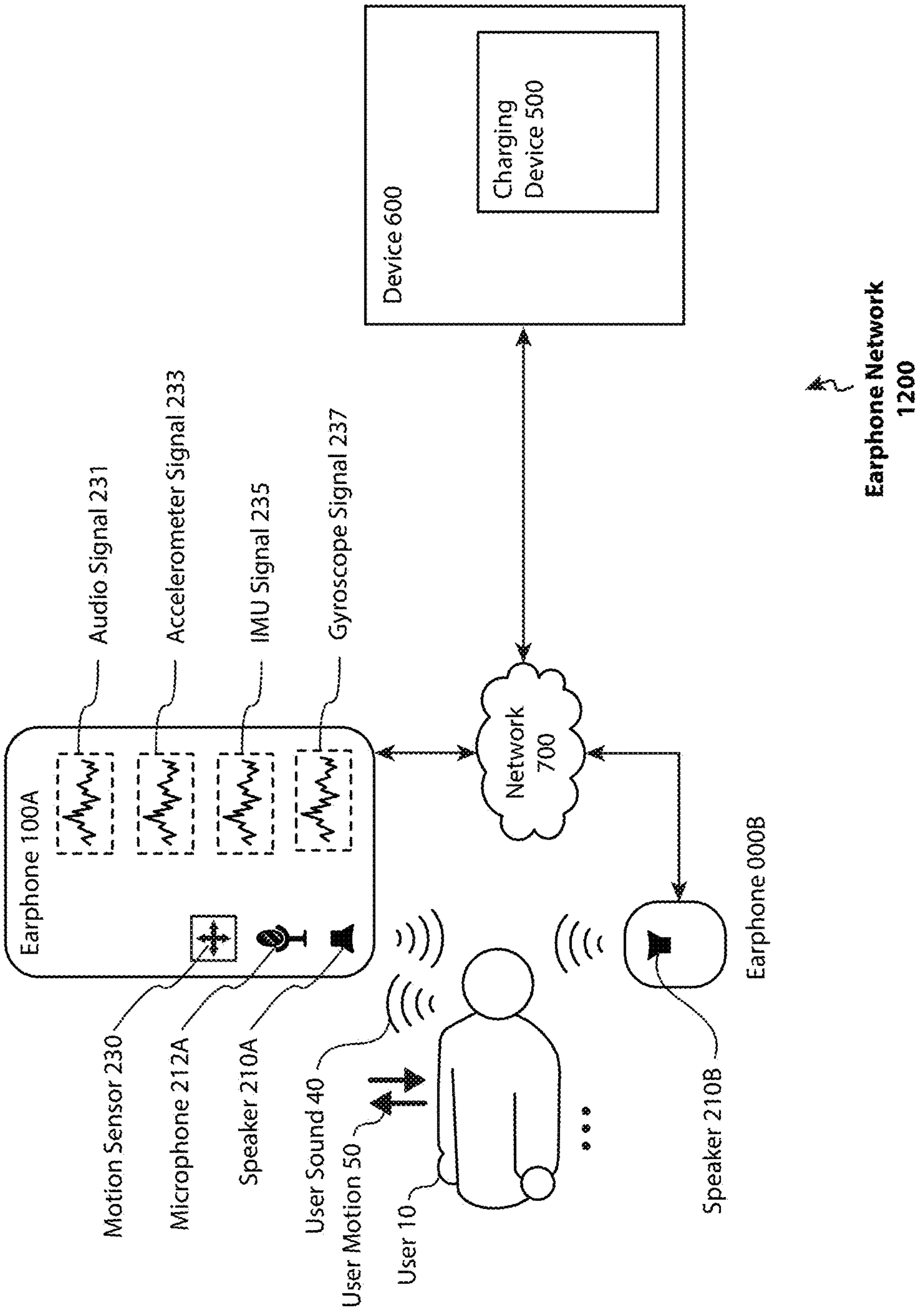
FIG. 12 illustrates a device network in which a pair of earphones may be coupled through a network (e.g., a communication network such as a Bluetooth® and/or WiFi® network) to each other and/or to one or more devices such as smartphones or connectable earbud cases, according to one or more embodiments.

FIG. 12 illustrates a device network 1200 in which a pair of earphones such as an earbud 100A and an earbud 100B may be coupled through a network 700 (e.g., a communication network such as a Bluetooth® and/or WiFi® network) to each other and/or to one or more devices 600. In one or more embodiments, the device 600 may be, for example, a smartphone, a tablet, or a connectable charging cases 550 for the earphones 100, according to one or more embodiments.

The user 10 may attempt to generate a control input 240 through directly interfacing with a touch interface of the earbuds 10. For example, the user 10 may reach up and touch the earbud 100 on the touch interface sensor 218, and/or through the device, system, and/or method further illustrated in FIG. 13 through FIG. 19.

A user 10 may utilize the earbud 100A and the earbud 100B to aid in sleep, for example providing audio from a speaker 210A and/or a speaker 210B, respectively. According to one or more embodiments the audio may provide masking sounds, generate white noise, and/or actively cancel noise within the external environments of the user 10. Each of the earbud 100A and the earbud 100B may include a network interface controller 216 for connection to each other and/or one or more devices 600 through a network 700. The network 700 may comprise one or more communication networks, for example local area network (LAN), a wireless network (e.g., Bluetooth®, WiFi®), a wide area network (WAN), and/or the Internet.

The device 600 may be a data processing device such as a smartphone (e.g., an iPhone®, an Android® device), a server computer, and/or a charging device 500 that may include data processing capability. For example, the device 600 may include the charging interface 501. The earbuds 100 and the possible hardware and software thereon are further shown and described in conjunction with the embodiment of FIG. 13, and the device 600 and the possible hardware and software thereon are further shown and described in conjunction with the embodiment of FIG. 14.

In the embodiment of FIG. 12, the user 10 is shown in a resting position, for example lying down. Other resting positions might include resting the head of the user against a wall or car window, sitting or reclining in a chair or couch, or laying a head down on a desk. The user 10 may produce a user sound 40 and/or a user motion 50. The user sound 40, for example, may include talking, breathing, snoring, rustling in bedding, and/or sound from other movement. The user sound 40 may be gathered on a microphone 212 as the audio signal 231 to be stored as the audio data 232, as shown and described in FIG. 13. For a sensitive enough microphone 212, and/or where the microphone 212 is directed towards the auditory canal 12, it may be additionally possible to hear the heartbeat of the user 10, for example as blood rushing through veins and/or arteries within the ear 11. The user motion 50 may result from breathing, movement of body parts (e.g., the lungs, chest, and/or related movements as shown and described in FIG. 20A and FIG. 20B), movement of the body caused by the heartbeat of the user 10, motion from speech or snoring, and/or motion from "macro movements" of the user 10 such as rolling over and/or changing position. The user motion 50 may be gathered by one or more motion sensors 230, for example an accelerometer 224, an inertial measurement unit 226 (e.g., "IMU"), and/or a gyroscope 228, as each are described in conjunction with the embodiment of FIG. 13, and/or other types of motions sensors.

Sound and/or motion signals collected by the earbud 100 may be processed on the earbud 100 and/or on the device 600. Similarly, control signals (e.g., a touch signal, a recoil signal, a vibration signal) may be evaluated, for example matched against motion signatures associated with control input 240. Evaluation and/or matching may occur on the earbud 100 and/or the device 600, according to one or more embodiments.

Figure 13:
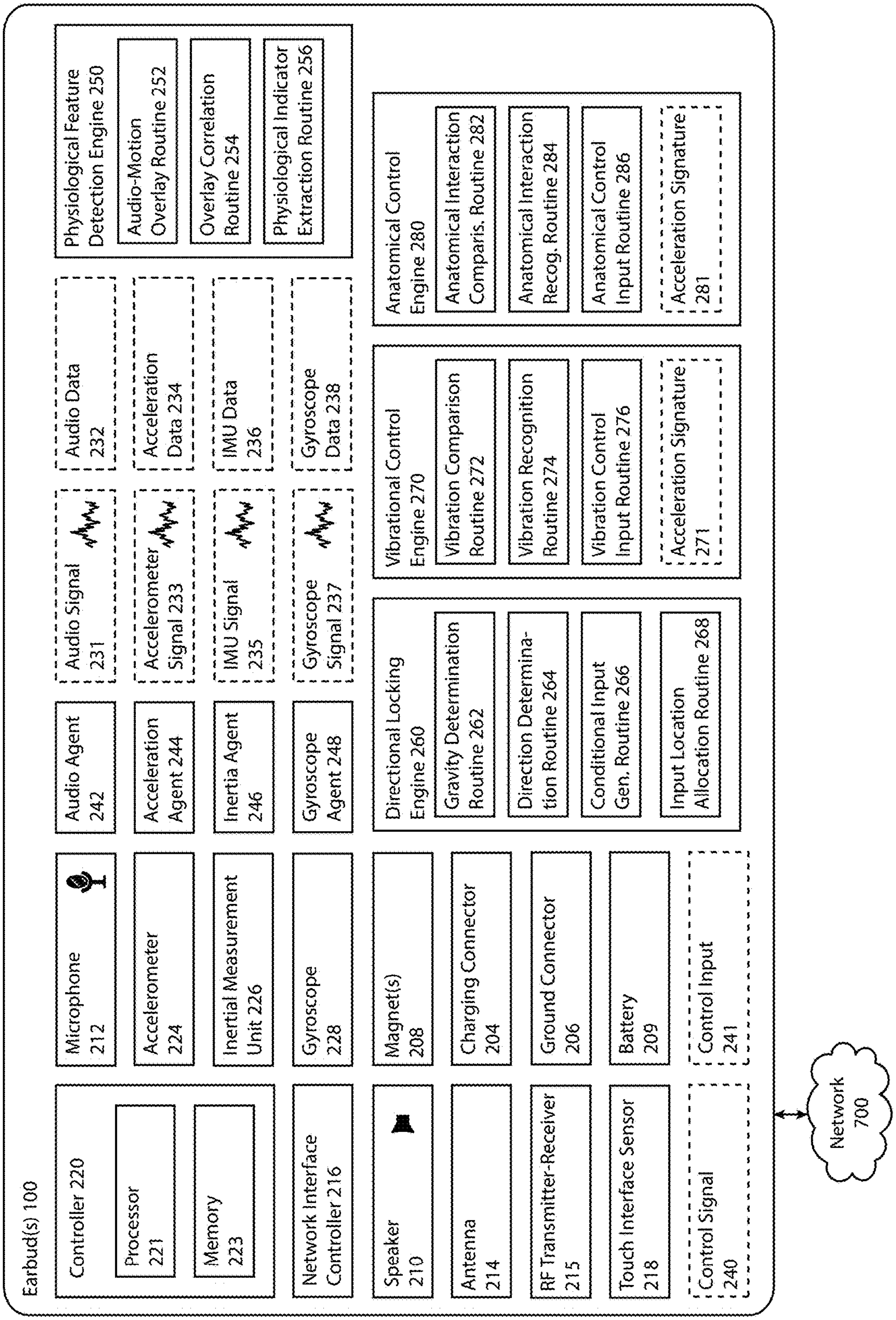
FIG. 13 illustrates one or more earphones and the hardware components, software components, and data, engines, and routines therein, usable to evaluate control inputs and/or accurately determine physiological features, according to one or more embodiments.

FIG. 13 illustrates one or more earphones 100 and the hardware components, software components, and/or data therein, including engines, routines, and/or modules used to evaluate control signals 240 and/or accurately determine physiological features, according to one or more embodiments. For ease of explanation, a single earbud 100 will be described in conjunction with the explanation of FIG. 13. However, it will be recognized that each of the hardware components, software components, and/or data therein (i) may be allocated to one of the earbuds 100, (ii) may be allocated between the earbud 100A and the earbud 100B, and/or (iii) may occur in both the earbud 100A and the earbud 100B (e.g., the controller 220A and the controller 220B, a gyroscope 228A and a gyroscope 228B, etc.), either for redundancy and/or to provide greater capability. In the last case, sensor data from both the earbud 100A and the earbud 100B may be assessed in one or more of the present embodiments. As just one example, acceleration data 233B and audio data 231A from the earbud 100A may be overlaid with acceleration data 233B and audio data 231B from the earbud 100B to assist in determining physiological indicators, as shown and described in conjunction with the embodiments of FIG. 20, FIG. 21, and FIG. 22.

The earbud 100 may include a controller 220 for controlling one or more hardware and/or software components of the earbuds 100. The controller 220 may include a processor 221 that may be a computer processor and a memory 223 that may be a computer readable memory. The controller 220 may include a microcontroller, for example a Qualcomm QCC30XX or a ST Micro BlueNRG-LP.

The earbud 100 may include a speaker 210, for example as may be coupled with the auditory canal 12 to provide audio to the user 10, as shown and described in conjunction with the embodiment of FIG. 10. The earphones 100 may include an antenna 214, for example an electrical trace as shown and described in conjunction with the embodiment of FIG. 11. The earbud 100 may also include an RF transmitter-receiver 215 configured for receiving wireless communication signals over one or more wireless protocols, for example Bluetooth®. In one or more embodiments, the RF transmitter-receiver may be a standalone transmitter-receiver, and/or may be included in the ST Micro® BlueNRG-LP, or another processing unit. The earbud 100 may further include a network interface controller 216 for processing one or more communications protocols sent and/or received on the RF transmitter-receiver 215.

The earbuds 100 may include a touch interface sensor 218, for example a resistive sensor, a capacitive sensor, a pressure sensor, a surface acoustical wave sensor, and/or an infrared sensor. In one or more embodiments, and as shown and described in conjunction with the embodiment of FIG.

11, the touch interface sensor 218 may include a surface resistive and/or capacitive sensor surface able to detect contact from skin and/or a finger of the user 10. Although not shown, additional touch interface sensors 218 and/or other contact or proximity such as IR sensors may be internally facing to the ear 11 of the user 10 and may be utilized to detect when the earbuds 10 are seated and/or properly positioned within the ear 11.

In one or more embodiments, and as shown and described in FIG. 1 through FIG. 11, the earbud 100 may include one or more magnets 208, one or more charging connectors 204, ground connectors 206, and/or one or more ground connectors 206. However, it will be recognized that the magnets 208, the charging connectors 204, and/or the battery 209 may be, in one or more embodiments, excluded from the earbuds 100. One or more of the present embodiments demonstrate considerations in expanding "control space" (e.g., number of control input 241 that can issued to the earbuds 100). One or more of the present embodiments also demonstrate considerations in optimizing the amount of physical interface space (e.g., space and layout of the exterior plate 205). While there are advantages in combining one or more of the present embodiments. However, it will be recognized that the magnets 208, the charging connectors 204, and/or the battery 209 are not necessary to one or more of the present embodiments, including, for example, the embodiments of FIG. 15 through FIG. 22.

The earbuds 100 may include a battery 209, for example a Varta® CPP 9440A3 battery. The earbuds 100 may also include one or more microphones 212, for example a PUI Audio® AMM2742.

The earbuds 100 may include one or more motion sensors 230. The motion sensors 230 may include an accelerometer 224, an inertial measurement unit 226, and/or a gyroscope 228. The accelerometer 224 may generate an accelerometer signal 233 that may be processed and/or stored as an acceleration data 234, for example on the processor 221 and the memory 223 and/or on the processor 602 and the memory 604 of the device 600. The accelerometer 224, for example, may include be based on an IMU within an ST Micro® LSM6DSL. The inertial measurement unit 226 may generate an IMU signal 235 that may be processed and/or stored as the acceleration data 236, for example on the processor 221 and the memory 223 and/or on the processor 602 and the memory 604 of the device 600. The inertial measurement unit 226, for example, may be included in the ST Micro® LSM6DSL. Similarly, the gyroscope 228 may generate the gyroscope signal 237 that may be processed and/or stored as the gyroscope data 238, for example on the processor 221 and the memory 223 and/or on the processor 602 and the memory 604 of the device 600. The gyroscope 228, for example, may be included in the ST Micro® LSM6DSL.

Various signals or data (e.g., the audio data 232, the acceleration data 234, the IMU data 236, and/or the gyroscope data 238) may be continuously, periodically, and/or randomly collected, including over comparable time intervals or epochs. In one or more embodiments, an agent may "listen for", may initially filter, and/or may preliminarily process signals and/or data from the microphone 212 and/or the motions sensors 230. For example, data without any recognizable periodicity and/or no recognizable waveforms may be discarded. An acceleration agent 244 may receive the acceleration signal 233, engage in any signal preprocessing steps, and store the acceleration data 234. Similarly, an inertia agent 244 may receive the IMU signal 235, engage in any signal pre-processing steps, and/or then store IMU data 236. The gyroscope signal 237 and gyroscope data 238 may be similarly collected or received by the gyroscope agent 248, including any optional data pre-processing. Each of the agents described herein may hold references to stored data until queried, and/or may deliver relevant data to one or more other procedures, engines, routines, sub-routines and/or modules, according to one or more embodiments.

In one or more embodiments, the earphones such as the earbuds 100 may include a directional locking engine 260. The directional locking engine 260 may be configured to determine whether to generate a control input 240 from a control signal 240 based on a directionality of the earphone such as the earbud 100. In one or more embodiments, the directional locking engine 260 may include computer readable instructions that when executed on a processor (e.g., the processor 221, the processor 602) receive a control signal 240 from a touch sensor (e.g., the touch interface sensor 218) of a first earphone (e.g., a first earbud 100A) generated by activation of the touch sensor (e.g., the user 10 intentionally touching the earbud 100A, the user 10 unintentionally touching the earbud 100A).

The directional locking engine 260 may include a gravity determination routine 264 configured to determine a direction of gravity. In one or more embodiments, the gravity determination routine 264 includes computer readable instructions that when executed receive from a motion sensor 230 (e.g., an accelerometer 224 of the earphone 100) a first acceleration data 234 comprising a positive acceleration indicating a direction of gravity. The accelerometer 224 may be physically fixed relative to the outside face (e.g., the exterior plate 205) of the earbud 100.

The directional locking engine 260 may further include a direction determination routine 264 configured to determine a direction and/or orientation of the earphones such as the earbuds 100. For example, orientation may be determined relative to an arbitrary location, such as the ear tip 104 and/or an axis extending through the outside face and/or exterior plate 205 (e.g., the plane 1502), as further shown and described in conjunction with the embodiment of FIG. 15. In one or more embodiments, directionality may be determined from one or more of the motion sensors 310, including for example the gyroscope 228 and/or the resulting gyroscope data 238 which may be periodically generated and/or queried by the directional locking engine 240. In one or more embodiments, the direction determination routine 264 includes computer readable instructions that when executed detects a direction of the touch sensor (e.g., the touch interface sensor 218) relative to the direction of gravity (e.g., the direction of gravity 1500 of FIG. 15). In one or more embodiments, the direction determination routine 264 may include computer readable instructions that when executed determine that an axis extending perpendicularly from a plane parallel to the exterior surface (e.g., which may also extend perpendicularly from the touch interface sensor 218) includes a directional component at least partially pointing toward the direction of gravity. For example, in a three-dimensional coordinate plane which may be established, where a z-axis may indicate an axis toward Earth and gravitational pull, and an origin point of is applied to the earbud 10 with a directional vector of {0,1,0}, any directional vector including a negative coordinate value for the z-component may qualify as a directional component at least partially pointing toward the direction of gravity. In one or more other examples, the head of a user 10 may be analogized to an aircraft subject to pitch, roll, and yaw. A neutral position with a positive rotation of a roll axis may indicate that a right-side earphone (such as an earbud 100R)

includes a directional component at least partially pointing toward the direction of gravity 1500.

The directional locking engine 260 may further include a conditional input generation routine 266 configured to generate a control input 241 from a control signal 240 based on the directionality of the earbud 10 relative to a direction of gravity 1500. In one or more embodiments, the conditional input generated routine 265 includes computer readable instructions that when executed determine whether to generate the control input 242 from the control signal 240 based on criteria comprising the direction of the touch sensor (e.g., the direction of the axis 1504 extending perpendicular to the touch interface sensor 218) relative to the direction of gravity 1500, to reduce a probability of a false positive of the control signal 240 while the user 10 is engaged in a resting position (e.g., lying down, resting a head against an object such as a wall or car window, reclining while side-sleeping, etc.).

In one or more embodiments, the directional locking engine 260 may also require a more pronounced angle and/or directionality of the earbud 100 in order to precipitate a control input 294 from a control signal 292. In one or more embodiments, the direction determination routine 264 may be configured to determine whether an angle between the direction of gravity 1500 and an axis of the earbud 100 (e.g., the axis 1504, or a different axis) exceeds, is equal to, and/or is less than a certain angle. In one or more embodiments, the direction determination routine 262 includes computer readable instructions that when executed determine that an axis extending perpendicularly from a plane parallel to the exterior (e.g., the plane 1502, which may be parallel and/or coextensive with a plane of the touch interface sensor 218) is less than or equal to a 45-degree angle from the direction of gravity 1500, for example as shown and described in conjunction with the embodiment of FIG. 15.

In one or more embodiments, the directional locking engine 260 may completely lock receipt and/or processing of control signals 240 and/or generation of control input 241 based on directionality. Similarly, processable input signals and/or an active instance of the touch interface sensor 218 may be allocated to a left or a right earphone (e.g., the left earbud 100L or the right earbud 100R) based on directionality of the earphones. Such disabling and/or enabling may assist in sleep use cases for earphones such as the earbuds 100, for example to help prevent a user 10 who is sleeping on their side or resting against a vertical surface from creating noisy audio data 232 and/or generating inadvertent control input 241, according to one or more embodiments. The user 10 may be instructed or intuitively know that the earphone facing "up" may still be utilizable to receive control signals 240 such as touch inputs.

In one or more embodiments, the directional locking engine 260 may include an input location allocation routine 268 comprising computer readable instructions that when executed determine a first earphone (e.g., the earbud 100R) of a pair of earphones is facing downward, disable the microphone 212 of the first earphone (e.g., a microphone 212R) and/or a touch sensor of the first earphone (e.g., a touch interface sensor 218R), determine a second earphone (e.g., an earbud 100L) of the pair of earphones is facing upward, and enabling the microphone 212 of the second earphone (e.g., microphone 212L) and a touch sensor of the second earphone (e.g., a touch interface sensor 218L). For example, this may ensure that at least one headphone of the pair of headphones always has an active microphone 212 and/or touch interface sensor 218, while allocating active control to the earbud 100 least likely to receive a false positive.

Disabling and/or enabling a left or right control interface may further reduce the available controls. This may occur because controls may not be able to be assigned to both earphones and/or controls may not be able to be assigned to simultaneous use of both earphones (e.g., pressing and holding both earbuds 100 at the same time to initiate noise canceling). Desire for an expanded control space may, however, demonstrate an increase advantage in one or more of the control input devices, systems, and methods further shown and described in conjunction with the embodiments of FIG. 17 through FIG. 19, and as further described throughout the present embodiments.

In one or more embodiments, the earphones such as the earbuds 100 may include a vibrational control engine 270. The vibrational control engine 270 may include computer readable instructions that when executed generate a control input based on recognition of a motion pattern such as a vibration. The vibration may be determined through one or more motions sensors 230, but in one or more embodiments may utilize the acceleration data 234. In one or more embodiments, the vibration data 234 may be compared against an acceleration signature 271 to determine a sufficient match. For example, the acceleration signature 271 may include pre-recorded instances of acceleration data stored in the memory 223 as default acceleration signatures 271, and/or custom-recorded instances of the acceleration data when configuring controls. The acceleration signatures 271 may be stored in a signature library, which may be stored on the earbud 100 and/or the device 600.

In one or more embodiments, and as further shown and described in conjunction with the embodiment of FIG. 17, the earbuds 100 and/or the device 600 to which the earbuds 100 may be connected may include a vibrational control engine 270 that may enable vibration-based controls. The vibration control engine 270 may include a vibration comparison routine 272 that may be configured to receive an acceleration data 234. The acceleration data 234 may include a vibration signal (e.g., an oscillation, a recurring signal, a periodic signal, etc.). The vibration control engine 270 may then retrieve one or more acceleration signatures 271 for comparison. The vibration may be an interaction between the earbuds 100 and the finger of the user 10, for example vibration caused by friction of the finger moving over a specific surface of the earbud 100 (e.g., rubber, smooth plastic, surface features such as the those within the charging interface 101, etc.).

In one or more embodiments, the vibration comparison routine 272 may include computer readable instructions that when executed compare the acceleration data 234 to the acceleration signature 271 that describes vibration of the earphone 100. The vibration of the earphone 100 may result when the finger of the user 10 moves across the touch sensor (e.g., the touch interface sensor 218) and/or the outside face of the earphone 100 (e.g., the exterior-facing portion of the exterior plate 205).

In one or more embodiments, the vibrational control engine 270 may include a vibration recognition routine 274 configured to determine whether a match (and/or a substantial match within a statistical probability) has occurred between the acceleration data 234 and the acceleration signature 271. In one or more embodiments, the vibration recognition routine 274 may include computer readable instructions that when executed determine a match between the acceleration data 233 and the acceleration signature 271.

In one or more embodiments, the vibrational control engine 270 may include a vibration control input routine 276 configured to determine whether to generate a control input 231 based on evaluation of the acceleration data 234 that includes the vibration. In one or more embodiments, the vibration control input routine 276 may include computer readable instructions that when executed determine whether to generate the control input 241 from the control signal 240 based on criteria that may include a match (e.g., a sufficient match within a statistical probability) between the acceleration data 234 and the acceleration signature 271, to reduce the probability of the false positive of the control signal 240 while the user 10 is engaging in rest. For example, the resting position may cause various vibrations (the earbud moving over a pillowcase), compressions against anatomical elements of the ear 11, and/or associated recoils when the user 10 moves and/or repositions while resting or sleeping.

In one or more embodiments, and as further shown and described in conjunction with the embodiment of FIG. 17, the earbuds 100 may include an anatomical control engine 280 that may enable controls based on user-initiated interactions between an earphone and the ear 11 of the user 10. In one or more embodiments, the anatomical control engine 280 may control the earbuds 100 based on interactions between anatomical components of the ear 11 and the earbud 100, especially when a force and/or pressure is applied by a finger of the user 10. Similar to the acceleration signature 271, the anatomical control engine 280 may utilize an acceleration signature 281 which may describe a "signature" of acceleration, in the present case for the pressing and/or recoil of the earbud 100 against a portion of the ear 11 of the user 10. For example, and as further shown and described in conjunction with the embodiment of FIG. 17, the user 10 may push the earbud 100 toward the tragus 14 and the let it recoil. Due to the unique springiness and/or asymmetric positioning of the ergonomic fit of the earbuds 100 when seated in the ear 11, the interaction may produce a signature acceleration when pressed, and/or a signature acceleration during recoil when released.

The anatomical control engine 280 may include an anatomical interaction comparison routine 282 configured to receive and compare an acceleration data 234 with an acceleration signature 281. The acceleration signature 281 may include a compression signal and/or a recoil signal. In one or more embodiments, the anatomical control engine 280 may include computer readable instructions that when executed compare an acceleration data 234 to an acceleration signature 281 that describes acceleration of the earphone 100 when pressed by the finger of the user 10 against an anatomical element of the ear 11 and/or when released from the anatomical element. The anatomical element may include, for example, a tragus 14, an anti-tragus 16, an intertragic notch, 18, an anti-helix 22, a cymba conchae 21, a cavum conchae 23, and/or an antihelical fold 24 of a helix 28.

In one or more embodiments, the anatomical control engine 280 may include an anatomical interaction recognition routine 284 configured to recognize an acceleration data 234 as matching (e.g., within a statistical probability) an acceleration signature 281. In one or more embodiments, the anatomical control engine 280 includes computer readable instructions that when executed determine the match between the acceleration data 234 and the acceleration signature 281.

In one or more embodiments, the anatomical control engine 280 may include an anatomical control input routine 286 configured to determine whether to generate a control input 241 based on evaluation of the acceleration data 234 that includes the compression and/or recoil signal. In one or more embodiments, the anatomical control input routine 286 may include computer readable instructions that when executed determine whether to generate the control input 241 from the control signal 240 based on criteria that may include a match between the acceleration data 234 and the acceleration signature 281, to help reduce the probability of the false positive of the control signal while the user 10 is engaged in the resting position. For example, the resting position may cause various vibrations, compressions, and/or recoils when the user 10 moves and/or repositions while resting or sleeping.

Figure 20A:
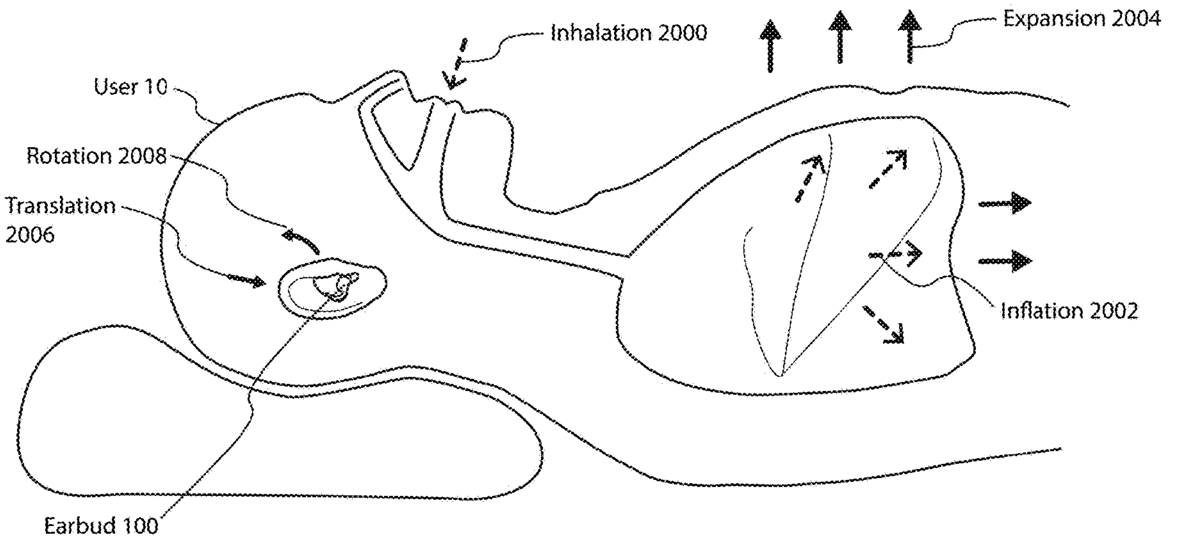
FIG. 20A illustrates an example of possible motion of a user during an inhalation that may be usable for determination of physiological features, such as respiration rate, that can be useful in evaluating cognitive states of the user, such as a sleep state, according to one or more embodiments.
Figure 20B:
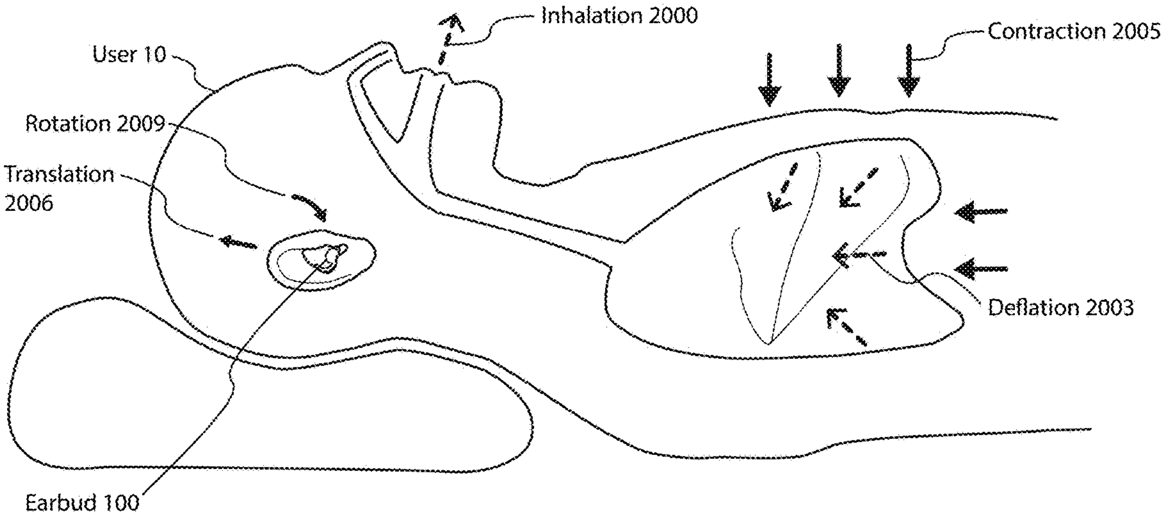
FIG. 20B illustrates an example of possible motion of the user during an exhalation, according to one or more embodiments.
Figure 21:
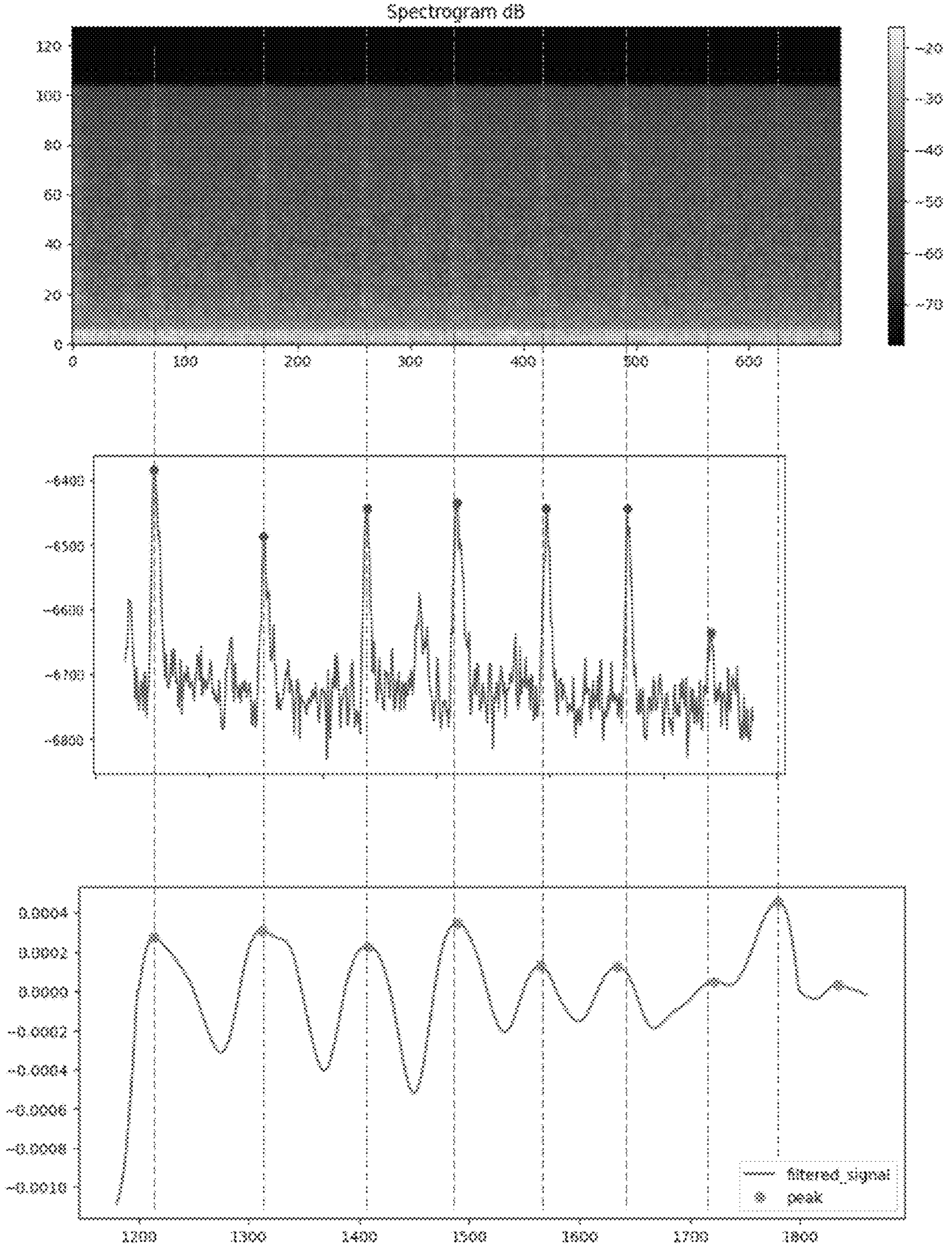
FIG. 21 illustrates physiological data usable to determine a respiration event and/or a respiration rate through correlation with audio data, in part for increased accuracy, according to one or more embodiments.

In one or more embodiments, and as further shown and described in conjunction with the embodiment of FIG. 20 and FIG. 21, the earbuds 100 may include a physiological feature detection engine 250 that may be configured to determine a physiological indicator, and further to determine physiological features therefrom. In one or more embodiments, the physiological feature detection engine 250 may be based on signals and/or data from the microphone 212 (e.g., the audio signal 231) in addition to one or more of the motion sensors 230 (e.g., the accelerometer signal 233, the IMU signal 235, and/or the gyroscope signal 237).

In one or more embodiments, the earbuds 100 may include a physiological feature detection engine 250 configured to detect one or more physiological features of the user 10 (e.g., heartbeat, respiration rate) based on signals from the microphone 212 and one or more of the motion sensors 230.

In one or more embodiments, the physiological feature detection engine 250 may utilize the acceleration agent 244, which may include computer readable instructions that when executed receive from the accelerometer 224 of an earphone (e.g., such as the earbud 100) an accelerometer signal 233 over a time period. The accelerometer signal 233 may comprise one or more acceleration events, for example distinct accelerations of the earphone such as the earbud 100. The acceleration agent 244 may additionally include computer readable instructions that when executed store the accelerometer signal 233 as an acceleration data 234 for the time period in a computer readable memory (e.g., the memory 223). The time period may be depend on the physiological features targeted, but for example could be 2 seconds, 5 seconds, 10 seconds, 30 seconds, one minute, or longer periods of time. Data collected from the microphone 212 and the motion sensors 230 may be synchronized such that data are collected for concurrent and corresponding time periods. The acceleration agent 244 may receive acceleration data 234 that includes a description of the inhaling and exhaling of the user 10.

The physiological feature detection engine 250 may also utilize an audio agent 242, which may include computer readable instructions that when executed: (i) receive an audio signal 231 over the time period from the microphone 212, the audio signal including two or more audio events (e.g., distinct recorded sounds, such as breaths of the user 10 or portions thereof), and (ii) storing the audio signal 231 as an audio data 232 in the computer readable memory (e.g., the memory 223). For example, the audio signal 231 and/or the audio data 232 may include audio of a sound of the user 10 inhaling and exhaling, for example as shown and described in conjunction with FIG. 20A and FIG. 20B. In one or more embodiments, the earbud 100 may include a single microphone 212 that may be sensitive enough to detect sound from both heartbeat and respiration. In one or more embodiments, the earphones may also include a microphone 212 may be an external-facing microphone 212, which may be suitable to collect sound within the sleeping environment of the user 10 and/or externally audible sounds of the user 10 (e.g., speaking, respiration). In one or more embodiments, the earphones may also include a microphone 212 that is internal facing, for example coupled to the auditory canal 12 of the ear 11. The internal-facing microphone 212 may be able to gather audible sounds of the user 10 (e.g., speaking, respiration) and the sound of physiological indicators such as a heartbeat.

In one or more embodiments, the physiological feature detection engine 250 may be configured to overlay one or more sets of collected data, for example the audio data 232 and data from one or more motion sensors 230. In one or more embodiments, the physiological feature detection engine 250 may include audio-motion overlay routine 254 that may include computer readable instructions that when executed overlay the acceleration data 234 and the audio data 232 for the time period.

The physiological feature detection engine 250 may include an overlay correlation routine 254 configured to correlate a motion event with either an audio event or another motion event, as each are recorded in applicable data over the epoch. In one or more embodiments, the overlay correlation routine 254 may include computer readable instructions that when executed determine a correlation between two or more acceleration events (e.g., recorded in the acceleration data 234) and the two or more audio events (e.g., recorded in the audio data 232) over the time period.

In one or more embodiments, a physiological feature determination routine 690 may include computer readable instructions that when executed determine the respiration rate of the user based on the one or more acceleration events over the time period. In one or more embodiments, a cognitive state determination module 692 may include computer readable instructions that when executed determine a cognitive state of the user based on the respiration rate and/or other physiological data such as heart rate. The cognitive state may be at least one of an awake state, a pre-sleep state, a sleep state, a REM state, and a NREM state.

The physiological feature detection engine 250 may include a physiological indicator extraction routine 256 configured to extract one or more correlated events. The physiological indicator extraction routine 256 may include computer readable instructions that designate and/or tag an event based on one or more of its properties within the applicable data. As just one example, periodic correlated event with a longest period of reoccurrence may be a respiration event, whereas an abrupt but small motion may a heartbeat event. In one or more embodiments, the physiological indicator extraction routine 256 may include computer readable instructions that when executed extract two or more physiological indicators matching the correlation of the two or more acceleration events and the two or more audio events over the time period, to reliably determine a physiological indicator. The physiological indicator, as shown and described throughout the present embodiment, may be useful for determining a physiological feature such as heart rate and/or respiration rate.

Following identification and/or extraction of or more physiological indicators, the raw data and/or waveforms may be simplified for data storage and/or transmission economy, for example structured as data specifying each identified physiological indicator. The resulting data may be referred to as a physiological indicator data, and may be stored for each epoch.

The physiological indicator data may be further processed on the earbuds 100, and/or may be communicated to the device 600 over the network 700. The physiological indicator data may be utilized for determination of physiological features. Physiological features then may be utilized for a cognitive state determination (e.g., an awake state, a pre-sleep state, a sleep state, and/or a gradation of sleep state such as REM, non-REM, deep sleep, and/or shallow sleep). The physiological indicator data may be evaluated by the physiological feature determination routine 690 for determination of one or more physiological features. Although the physiological feature determination routine 690 is shown and described in conjunction with the embodiment of FIG. 14, the physiological feature determination routine 690 may also execute partially or completely on the earbuds 100, according to one or more embodiments. Similarly, in one or more embodiments, the cognitive state determination routine 692 may execute partially or completely on the earbuds 100 and/or the device 600.

In one or more embodiments, the gyroscope data 238 and/or the IMU data 236 may also be correlated with the audio data 232, for identification of physiological indicators.

In one or more embodiments, the gyroscope agent 248 may include computer readable instructions that when executed receive from a gyroscope 228 of the earphone 100 a gyroscope signal 231 over the time period, where the gyroscope signal 231 includes one or more axis rotation events. The axis rotations events may be periodic and/or include a rotation counter-rotation periodicity, for example as shown and described in conjunction with the embodiments of FIG. 20A and FIG. 20B. The gyroscope agent 248 may also include computer readable instructions that when executed store the gyroscope signal 237 as a gyroscope data 238 for the time period in the computer readable memory (e.g., the memory 223, the memory 604).

In one or more embodiments, the audio-motion overlay routine 252 may include and/or may further include computer readable instructions that when executed overlay the audio data 232 with the gyroscope data 238 and/or the acceleration data 234 for the time period. In one or more embodiments, the overlay correlation routine 256 may include and/or may further include computer readable instructions that when executed determine over the time period the correlation between two or more axis rotation events and either, or both of: (i) two or more acceleration events (e.g., from the acceleration data 234) and/or (ii) the two or more audio events (e.g., from the audio data 232).

Figure 14:
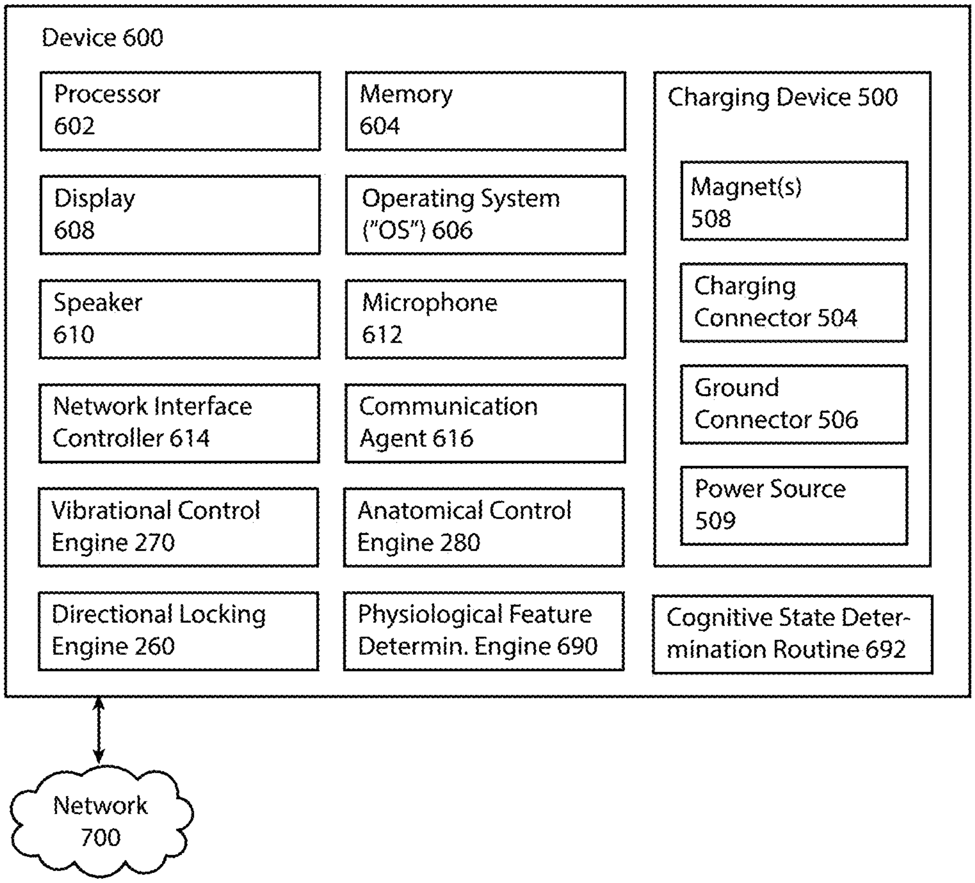
FIG. 14 illustrates the device, such as a smartphone or charging case, and the hardware components, software components, and data, engines, and routines, usable to evaluate control inputs and/or accurately determine physiological features, according to one or more embodiments.

FIG. 14 illustrates a device 600, such as a smartphone or charging case, and the hardware components, software components, and data therein, including engines, routines, and/or modules, according to one or more embodiments. The device 600 may include a processor 602 and a memory 604. In one or more embodiments, the processor 602 may be of greater power than the processor 228, which may be limited by both the size of the earbuds 100 and the battery 209. Similarly, the memory 604 may be of greater size and capacity than the memory 223. Therefore, in one or more embodiments, the device 600 may be utilized to store and process greater amounts of data and/or execute more resource and/or power intensive procedures. For example, the functions and/or computer readable instructions implementing all or part of the physiological feature detection engine 250, the physiological feature determination routine 690, and/or the cognitive state determination routine 692 may be performed partially or completely on the device 600. The device 600 may generate remote procedure calls to additional computers, servers, and/or devices as needed for backup storage, additional processing, and/or calling complex recognition and/or matching models (e.g., a machine learning and/or AI model for determining cognitive state of the user 10 from physiological feature data).

The device 600 may include an operating system 606 (e.g., Windows®, macOSX® Linux®, Android®, iOS®, an embedded real-time operating system (RTOS), e.g., FreeRTOS, QNX, etc.), a display 608 (e.g., an LCD display, and LED display), a speaker 610, and/or a microphone 612. In one or more embodiments, the microphone 612 may be utilized to gather the audio data 232, including sound events related to the user 10 such as respiration events. The device 600 may include a network interface controller 614 for communicating over the network 700, and which may include a wireless capability for wirelessly communicating with the earbuds 100 directly (e.g., via a Bluetooth® or other protocol supporting direct connection). A communication agent 616 may be configured to receive and respond to incoming requests from earphones such as the earbuds 100, for example receiving physiological indicator data, passing the physiological indicator data to the physiological feature determination routine 690 and subsequently to the cognitive state determination routine 692, and/or mediating a response which may include one or more instructions to the earbuds 100 based on a determination of cognitive state.

Although shown and described in conjunction with the embodiment of FIG. 13, the device 600 may include the directional locking engine 260, and/or the vibrational control engine 270, the anatomical control engine 280, or portions thereof. For example, the earphones such as the earbud 100 may communicate motion data (e.g., the acceleration data 234, the IMU data 236, and/or the gyroscope data 238) to the device 600 over the network 700 for analysis or storage. The device 600 may then issue a control input 241 and/or instruct through the network 700 for the earbuds 100 to produce the control input 241. In one or more embodiments, the earphones such as the earbuds 100 may make a remote procedure call (RPC) to the device 600 over the network 700 for these and other functions, or portions thereof.

In one or more embodiments, the device 600 may include a physiological feature determination routine 690. The physiological feature determination routine 690 may be configured to determine one or more physiological features from one or more physiological indicators, for example as recorded in the physiological indicator data. For instance, a count may be made of the physiological indicators tagged and/or identified with a certain physiological indicator type, for example heartbeat events, respiration events, and/or other types of physiological indicators. The physiological feature determination routine 690 may then determine a rate based on the period of time over which collection occurred, for example resulting in calculation of a heartrate, a respiration rate, and/or an occurrence rate of other types of physiological indicators. The physiological feature determination routine 690 may output a physiological feature data specifying each physiological feature for the time period, or over multiple time periods. The physiological feature determination routine 690 may also determine heart rate variability, respiration rate variability, and/or compare against previously generated instances of the physiological feature data over previous time periods to generate more accurate physiological feature determination, including averages over greater time periods. In one or more embodiments, the physiological feature determination routine 690 includes computer readable instructions that when executed determine the respiration rate of the user 10 based on the one or more acceleration events over the time period, for example acceleration events identified as physiological indicators of respiration events.

A cognitive state determination routine 692 may determine a cognitive state of the user 10 based on the physiological indicators and/or physiological features of the user 10. The cognitive state data may be utilized, for example, for statistical purposes (e.g., sleep data of the user), to generate control input (e.g., turning of the audio of the earbud 100 that may be playing to the user 10 when the user 10 once the user 10 falls asleep), and/or for other uses. The cognitive state determination routine 692 may utilize one or more methods as known in the art to identify cognitive state based on heart rate, heart rate variability, respiration rate, respiration rate variability, and/or other physiological features. In one or more embodiments, the cognitive state determination routine 692 may utilize machine learning and/or “artificial intelligence” methods, devices, and/or systems to identify cognitive state of the user 10 based on physiological features. An AI system may be trained on data from multiple instances of the user 10, including utilizing either supervised or unsupervised learning techniques, or both.

In one or more embodiments, the cognitive state determination routine 692 may include computer readable instructions that when executed determine the cognitive state of the user 10 based on the respiration rate and/or the respiration rate variability, for example as determined from the acceleration data 234, the audio data 232, and/or the gyroscope data 238.

In one or more embodiments, the device 600 may be a charging device 500 such as a charging case 550. In such an embodiment, the changing case 600 may have one or more of the components of FIG. 14 (and/or FIG. 13) integrated therein. The device 600 that includes the charging device 500 may include charging connectors 504, ground connectors 506, magnets 508 (including for left or right instances of the earbuds 100), and/or a power source 509. The power source 509 may be a battery and/or a DC power supply from a wall outlet or other power source. An example of the charging case 550 that may include one or more of the components of the device 600 is shown and described in conjunction with the embodiment of FIG. 8 and FIG. 9.

FIG. 15 illustrates an earphone directionality evaluation view 1550 usable to evaluate control signals 240 to lock input and/or prevent false positives in generating control input 241, especially as may be useful to prevent false positives resulting from resting positions, according to one or more embodiments. In the embodiment of FIG. 15, the earbud 100 (specifically, a right-handed earbud 100R) is shown seated in the ear 11 (e.g., a right ear 11R) of the user 10, including with the ear tip 104 acoustically coupled with the auditory canal 12. As previously shown and described throughout the present embodiments, evaluating control signals 240 generated and/or locking the control signal generation capability when the earbud 100 is at certain angles may be useful for instances of the earbuds 100 intended for use in resting and/or sleeping, according to one or more embodiments. Otherwise, inadvertent control signals 240 may result in unintended control input 241, which may arise above mere annoyance to disturbing the rest and/or sleep of the user 10.

In the present embodiment, to demonstrate one of several possible resting positions, the ear 11 is shown in contact with the surface 1501. The surface 1501, for example may be the arm of the user 10, a pillow, a sheet, a bed, a blanket, upholstery, a window of a vehicle, or another surface that the user 10 may rest their head and/or ear 11 against. The earbud 100 is shown having a plane 1502 that extends through the earbud 100 and runs parallel to the exterior surface (e.g., a plane approximating the exterior plate 205). An axis 1504 extends perpendicular to the plane 1502 and illustrates a directionality of the exterior-facing portion of the earbud 100. Another axis illustrates the direction of gravity 1500, where an angle 1506 is the angle between the direction of gravity 1500 and an axis such as the axis 1504 that may demonstrate a direction of the exterior-facing portion of the earbud 100.

In one or more embodiments, the earbud 100 may lock the touch interface sensor 218R when the angle 1506 is within a threshold number, for example equal or less than 90 degrees, equal or less than 55 degrees, equal or less than 30 degrees, etc. The appropriate threshold for the angle 1504 may be selected based on the needs of the user 10 and/or configured based on personal preference or common resting positions. For example, a user 10 who frequently commutes may wish to have a threshold at 80 degrees or less, whereas a user 10 who is a side-sleeper and primarily utilizes the earbuds 100 in bed may wish to have a threshold at 30 degrees or less.

In one or more embodiments, the direction of gravity 1500 may represent a z-axis in a coordinate plane, and locking of the touch interface sensor 218R may occur where the direction of the axis 1504 (e.g., a unit vector matching the axis 1504 and describing its direction) includes a negative z-component.

As shown and described through the present embodiments, the angle 1504 and/or the negative z-component may be determined from the gyroscope 228, and the direction of gravity 1500 may be determined from the accelerometer 224 and/or the gyroscope 228, and/or through other means known in the art utilizing one or more of the motion sensors 230.

Figure 16:
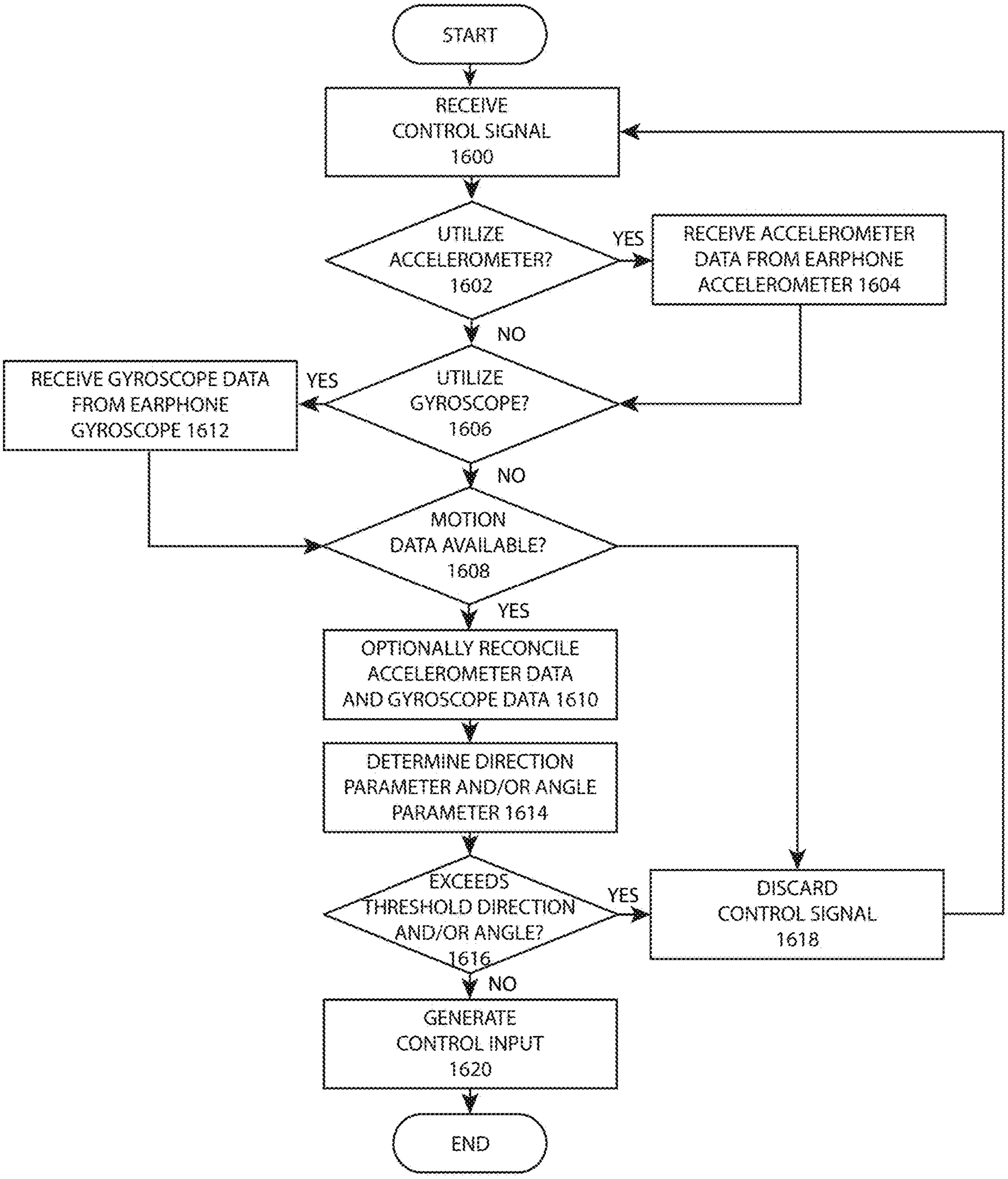
FIG. 16 illustrates a directional locking process flow for locking control inputs and/or reducing control input false positives, according to one or more embodiments.

FIG. 16 illustrates a directional locking process flow 1650, according to one or more embodiments. Operation 1600 may receive a control signal (e.g., the control signal 240) on a sensor intended and/or partly intended for use in generating control input 241. As an example, the control signal 240 may be received on touch interface sensor 218, which may be intended for exclusive use for generating control inputs 241, and/or may be received through the accelerometer 224 (e.g., a vibration signal and/or a recoil signal, as shown and described in the embodiments of FIG. 17 through FIG. 19).

Operation 1602 determines whether to utilize the accelerometer 224 in evaluating whether to lock the controls and/or enable generation of the control input 241 from the control signal 240. If the accelerometer 224 is to be utilized, operation 1602 may proceed to operation 1604 which receives an acceleration data 234 from an accelerometer 234 of the earphone (e.g., the earbuds 100), then proceeds to operation 1606. If operation 1602 will not utilize the acceleration data 234, operation 1602 may proceed directly to operation 1606.

Operation 1606 similarly determines whether to utilize the gyroscope 238 in evaluating whether to lock the controls and/or enable generation of the control input 241 from the control signal 240. If the gyroscope 238 is to be utilized, operation 1606 may proceed to operation 1612 which receives a gyroscope data 238 from a gyroscope 238 of the earphone (e.g., the earbud 100), then proceeds to operation 1608. If operation 1606 will not utilize the gyroscope data 238, operation 1606 may proceed directly to operation 1608.

Operation 1608 determines if any motion data (e.g., the acceleration data 234, the gyroscope data 238) is available (e.g., successfully queried, received, etc.). If no motion data is available, operation 1608 proceeds to operation 1618 which may discard the control signal 240. Alternatively, operation 1608 may proceed to operation 1620 to generate the control input 241, as further described below. However, it also may be advantageous to discard the control signal 240 according to operation 1618 to further reduce false positives, in case the user 10 is in fact resting or sleeping.

Where motion data is available, operation 1608 may proceed to operation 1610 which may optionally reconcile the motion data, for instance reconcile the acceleration data 234 and the gyroscope data 238. For example, it may be determined that the acceleration data 234 and the gyroscope data 238 are incompatible, mutually exclusive, and/or temporally misaligned. In such case, one or the other may be selected, operation 1610 may return to operation 1604, and/or operation 1612 to obtain new motion sensor data.

Operation 1614 determines a direction parameter and/or angle parameter. For example, a configurable parameter stored in memory (e.g., the memory 223) and/or within the directional locking engine 260 may specify a threshold angle (e.g., the angle 1506, as shown and described in conjunction with the embodiment of FIG. 15). In another example, the directional locking engine 260 may specify a direction parameter, for example a direction toward gravity. Operation 1614 may then proceed to operation 1616, which determines if the direction and/or the angle has been exceeded. Where the direction and/or the angle threshold is exceeded, operation 1616 may proceed to operation 1618. This may occur where the head of the user 10 is tilted as to exceed the angle threshold. It should be noted that although the term "exceeded" is utilized, a threshold may be exceeded may being equal to or less than a parameter value, as shown and described in conjunction with the embodiment of FIG. 15. For example, a threshold of less than 45 degrees may be exceeded when the angle is 44 degrees.

If the direction and/or angle is not exceeded, operation 1616 may proceed to operation 1620 which may generate the control input 241 such that an action can be performed by the earphones such as the earbuds 100. For example, the control input 241 may include a play instruction (e.g., to play a soundtrack or other audio data), a pause instruction, a skip track instruction, a volume instruction, a masking mode instruction (e.g., a sound masking mode), and a sleep check instruction (e.g., a query to ask a sleep tracking system how rested and/or how much the user 10 has slept), a transparency mode instruction (e.g., to allow sound through a sound masking and/or noise canceling system), and/or a locking instruction (e.g., to lock user controls until receiving an unlock instructions).

FIG. 17 illustrates an anatomical and vibrational control input 241 view 1750 demonstrating, independently and collectively, control inputs (e.g., control inputs 241) provided through compression against and/or recoil from anatomical elements of the ear 11 (e.g., anatomical elements shown and described in conjunction with the embodiment of FIG. 1), and additionally control inputs 241 provided through skin and/or touch interaction with various surfaces and/or surface textures of the earphone (e.g., causing vibrations detectable through motion sensors 230 such as the accelerometer 224 of the earbud 100), according to one or more embodiments.

In one or more embodiments, a control signal 240 can be generated by a motion of an earphone interacting with parts of the ear 11 of the user 10. Each anatomical element of the ear 11 may have a differing elasticity or "springiness" depending on a direction of a force applied to the anatomical element. Certain anatomical elements may also have certain depression limits and/or shore hardness directions of force against certain anatomical elements may even be modeled as a damped spring. With respect to an earbud such as the earbud 100, and anatomical element of the ear 11 contacting the earbud 100 may be useful in generating a unique detectable interaction when a force is applied against the anatomical element. Either the initial compression, the recoil once released, or both can be utilized in generating the control signal 240.

In the embodiment of FIG. 17, six example instances of a control motion 1700 are illustrated, each resulting in generation of a control signal 240 that may result in a control input 241. To generate the control motion 1700, the user 10 may place their finger on the central portion of the earbud unit 200, e.g., within the touch interface zone 294. Other placements are also possible, for example on the top of the earbud unit 200 (e.g., in the peripheral zone 293) and/or on the retainer 108. The user 10 may then apply force and/or pressure in a direction of an anatomical element of the ear 11.

The control motion 1700A illustrates a force applied against the antitragus 16 labeled as the compression 1702 (shown with a solid-lined arrow) and a subsequent recoil 1704 from the force of the antitragus 16 (shown in a dash-lined arrow). Similarly, the control motion 1700B may occur against the intertragic notch 18. The control motion 1700C and the control motion 1700D may both be made against the same anatomical element, the tragus 14, where each may be distinguished based on how the user 10 applies the force and/or permits the recoil. For example, the control motion 1700C may be a "flick" or quick tap of force with the finger, whereas the control motion 1700D may be a long hold followed by a release. The control motion 1700C and the control motion 1700D may be distinguished, for example, through differing acceleration signatures 281, as shown and described in conjunction with the embodiment of FIG. 13 and FIG. 18.

The control motion 1700E may be made against the uppermost region of the antihelical fold 24. Depending on the shape of the earphones and/or earbuds, the use 10 may have to place a finger on a different portion of the earphones and/or earbuds to effect certain control motions 1700. In the present example, the user 10 may generate the control motion 1700E by place their finger on the retainer 108 of the earbud 100 and/or the region between the retainer 108 and the earbud unit 200. The control motion 1700F is shown applied against the aftmost portion of the antihelix 22.

FIG. 17 distinctly illustrates one or more instances of control contact 1710 that may be used to generate control signals 240 for earphones and/or earbuds such as the earbuds 100, according to one or more embodiments. Three instances of the control contact 1710 are illustrated, each occurring in a different location of the earbud 100 and each on a potentially differing surface texture 1708. Each control contact 1710 may result in friction against the surface and/or a resulting vibration which may be compared against an acceleration signature 271, as shown and described in conjunction with the embodiments of FIG. 13 and FIG. 19.

As an example, a first surface texture 1708A may occur in the charging interface 101 and/or charging interface zone 291 due to slight depressions and/or differencing materials of the changing connector 204, the ground connector 206, and/or the magnets 208. Alternatively, or in addition, cosmetic patterns or surface ornamentation located around the charging interface 101 may be given slight surface texture, such as raised bumps, embossed ink, and/or fiction-inducing ink. In the present example, this surface ornamentation appears as small circular "stars". The user 10 may rub his or her finger over the surface texture 1708A to result in the control contact 1710A.

In contrast to the surface texter 1708A, and referring to FIG. 2, the control contact 1710B may occur on a relatively smooth surface of the surface texture 1708B, which may be present in the upper-left portion of the touch interface zone 294 and/or the upper-left portion of the peripheral zone 292. In yet another example in FIG. 17, the surface texture 1708C along the retainer 108 may enable the control contact 1710C.

In one or more embodiments, the finger may be able to travel in either or both directions along the surface texture 1708, provided that the texture is relatively consistent. In one or more other embodiments, if the surface texture 1708 changes texture, a directionality may be can be inferred. For example, the control contact 1710D may occur where the user 10 begins by placing their finger on the surface texture 1708A and transitioning to the surface texture 1708B. Conversely, the control contact 1710E may occur where the user 10 begins with their finger on the surface texture 1708B and transitions to the surface texture 1708C. Other textural differences in material, for example between the earbud unit 200 and the boot 400, may provide further opportunities for differing surface texture 1708 and therefore distinguishable control contacts 1710.

In one or more embodiments, both control motions 1700 and control contacts 1710 may be enabled in the same instance of the earbud 100. In one or more embodiments, a control contact 1710 may be distinguished from a control motion 1700 by a relative amount of force applied against the earbud 100. Where no substantial compression 1702 and/or recoil 1704 occurs (as may be determined from a non-match to an acceleration signature 281), the control contact 1710 may then be evaluated for a match against the acceleration signature 271. In one or more embodiments, the acceleration signature 281 include an acceleration and/or sensed motion traveling in distinct direction starting from an initial position when the earbud 100 is neutrally and properly seated in the ear 11. Acceleration signatures 281 may be initially collected from the user 10 during configuration of the earbuds 100, and/or datasets from multiple users 10 may be combined to determine a generalized acceleration signatures 281 sufficient for use with most users 10.

As a result of control motions 1700 and/or control contacts 1710, earphones such as the earbuds 100 may have a greatly expanded "control space" that may enable the user 10 to perform many controls without the additional assistance of a display screen or additional interfacing device (e.g., the device 600). Generating control input 241 through the control motions 1700 and/or the control contacts 1710 also may reduce the need for additional components or interior volume of the earbud unit 200, further supporting a smaller, and therefore more comfortable, form factor. As a result, the earbuds 100 may have an overall improved user interface (UI) and user experience (UX).

FIG. 18 illustrates an anatomical interaction control process flow 1850, according to one or more embodiments. The anatomical interaction control process flow 1850 may begin when an acceleration occurs to an earphone such as an earbud 100 seated on and/or in the ear 11 of the user 10. Operation 1800A illustrates an unknown acceleration 1800A, for example from a user 10 walking, running, turning over in their sleep, shaking their head, yawning, or speaking. In contrast, operation 1800B generates an acceleration that is intended by the user 10 as the initiation of a control signal, and specifically a control signal from a compression and/or recoil of an anatomical element of the ear 11. Operation 1800A and operation 1800B proceed to operation 1802. Operation 1802 generates an acceleration signal from the acceleration (e.g., the acceleration signal 233).

Operation 1804 may determine if a threshold compression and/or recoil is reached. For example, the compression and/or recoil may need to occur within a certain time period (e.g., 0.5 seconds, 1 second, 2 seconds), with sufficient amplitude (e.g., demonstrating true intention by the user 10) and/or with a minimal amount of signal noise. Where the compression and/or recoil threshold is not reached, operation 1804 may proceed to operation 1806 which may discard the accelerometer signal 1806. Alternatively, the accelerometer signal 233 and/or the resulting acceleration data 234 may be passed to one or more additional processes for evaluation of vibration controls, for example as shown and described in conjunction with the embodiment of FIG. 19.

Where the compression and/or recoil threshold is reached, operation 1804 may proceed to operation 1808 which may store the acceleration data 234 (e.g., in the memory 223). Operation 1808 may also transmit an acceleration data 234 to a device for processing (e.g., the device 600). Operation 1808 may then proceed to operation 1810. Although operation 1804 is illustrated in FIG. 18 as operating on the acceleration signal 233, for example as an analog signal filter, it should be noted that operation 1804 may also operate on data. In that case, the accelerometer signal 231 may be structured as a database and stored as the acceleration data 233 prior to operation 1804, and operation 1804 would then proceed to operation 1810.

Operation 1810 may query an acceleration signature library for an acceleration signature 281 that may match the acceleration data 234. One or more techniques known in the art of computer programming and/or computer science may be utilized to search the acceleration signature library, for example by selecting prominent features of the data (e.g., strong waveforms, prominent peaks, etc.), and/or querying against a feature index.

Operation 1812 compares the acceleration data 234 to the acceleration signature 281. Operation 1814 then determines whether the acceleration data 234 matches the acceleration signature 281, for example within tolerance of error, a sufficient percentile match, and/or a statistical probability. If the match is insufficient, operation 1814 may proceed to operation 1806. However, if the match is sufficient, operation 1814 may proceed to operation 1816 which may generate a control input (e.g., the control input 241) associated with the acceleration signature 281. For example, the control input 241 may be associated with the unique identifier (UID) of an acceleration signature 281 within a database and/or the acceleration signature library.

In one or more embodiments, certain control sensors signals may be combined to further decrease the chance of false positives. For example, when the user 100 places a finger on the earbud unit 200 to apply a control motion 1700, detection of the finger by the touch interface sensor 218 may be further required prior to assessment of the acceleration signature 281.

FIG. 19 illustrates a vibration control recognition process flow 1950, according to one or more embodiments. Similarly to the anatomical interaction control process flow 1850, the vibration control recognition process flow 1950 may begin when an acceleration occurs to an earphone such as an earbud 100 seated on and/or in the ear 11 of the user 10. Operation 1900A illustrates an unknown acceleration 1900A. Operation 1900B generates an acceleration that is intended by the user 10 as the initiation of a control signal 240, and specifically a control signal 240 from touching a surface texture (e.g., a surface texture 1708). Operation 1900A and operation 1900B proceed to operation 1902. Operation 1902 generates an acceleration signal from the acceleration (e.g., the acceleration signal 233). In the present example, the control signal 240 would include the acceleration signal 233.

Operation 1904 may determine if a threshold vibration is reached. For example, the vibration may require a sufficient amount of collection time (e.g., 0.1 seconds, 0.25 seconds, 1 second), threshold amount of wavelength consistency, and/or a minimal signal noise. Where the vibration threshold is not reached, operation 1904 may proceed to operation 1906 which may discard the accelerometer signal 1906. As a result, no control input 241 would be generated. Alternatively, the accelerometer signal 233 and/or the resulting acceleration data 234 may be passed to one or more additional processes for evaluation of compression and/or recoil, for example as previously shown and described in conjunction with the embodiment of FIG. 18.

Where the vibration threshold is reached, operation 1904 may proceed to operation 1908 which may store the acceleration data 234 (e.g., in the memory 223). Operation 1908 may also transmit an acceleration data 234 to one or more devices for processing (e.g., the device 600). Operation 1908 may then proceed to operation 1910. Although operation 1904 is illustrated in FIG. 19 as operating on the acceleration signal 233, for example as an analog signal filter, it should be noted that operation 1904 may also operate on data. In that case, similar to the situation as described in FIG. 18, the accelerometer signal 231 may be stored as the acceleration data 233 prior to operation 1904, and operation 1904 would then proceed to operation 1910.

Operation 1910 may query an acceleration signature library for an acceleration signature 271 that may match the acceleration data 234. One or more techniques known in the art of computer programming and/or computer science may be utilized to search the acceleration signature library, for example by selecting prominent features of the data (e.g., strong waveforms, strongly appearing frequencies, prominent peaks, etc.). The acceleration signatures 271 and the acceleration signatures 281 may be stored in the same instance of the acceleration signature library, according to one or more embodiments.

Operation 1912 compares the acceleration data 234 to the acceleration signature 271. Operation 1914 then determines whether the acceleration data 234 matches the acceleration signature 271, for example within tolerance of error, a sufficient percentile match, and/or a statistical probability. If the match is insufficient, operation 1914 may proceed to operation 1906. However, if the match is sufficient, operation 1914 may proceed to operation 1916 which may generate a control input (e.g., the control input 241) associated with the acceleration signature 271.

In one or more embodiments, certain control sensors signals may be combined to further decrease the chance of false positives. For example, when the user 100 places a finger on the earbud unit 200 to apply a control motion 1700, detection of the finger by the touch interface sensor 218 may be further required prior to assessment of the acceleration signature 271.

As shown and described in conjunction with the embodiment of FIG. 18, it is possible for the process of FIG. 18 and FIG. 19 to run concurrently and/or sequentially, that is, assess an acceleration for matches against an acceleration signature 271 and an acceleration signature 281.

FIG. 20A and FIG. 20B illustrate an example of possible motions of a user 10 during an inhalation and exhalation, respectively, that may be utilized for determination of physiological features, such as respiration rate, that can be useful in evaluating cognitive states of the user 10, according to one or more embodiments. FIG. 20A illustrates an inhalation 2000 of a user 10. The inhalation 2000 may occur with an inflation 2002 of the lungs and an expansion 2004 of the chest. As a result of these and other motions associated with the inhalation 2000, there may be motion imparted to head of the user 10. For example, there may be a translation 2006 from an initial origin point centered on the earbud 100 prior to the inhalation 2000. Similarly, as the rising chest of the user 10 during the inhalation 2000 may cause a rotation 2008 around a y-axis likely to intersect the head. The y-axis may be roughly parallel to an axis running through each ear of the user 10. The translation 2006 and the rotation 2008 may be detectable with one or more motion sensors 230 of the earbuds 100, for example the inertial measurement unit 226 and/or the gyroscope 228.

Other aspects of motion also may be detectable, for example vibration from snoring and/or other respiratory idiosyncrasies of the user 10. In addition to the translation 2006 and any rotation 2008 (examples of the user motion 50 of FIG. 12), there may be a generation of sound of the user 10 from inhaling and exhaling (e.g., the user sound 40 of FIG. 12).

FIG. 20B illustrates an example of possible motion of a user 10 during an exhalation 2001, or the reverse process of FIG. 20A, according to one or more embodiments. Associated with the exhalation 2001, the lungs may undergo the deflation 2003 and the chest may undergo the contraction 2005. The translation 2007 may occur, possibly as the reverse of the translation 2006, and the rotation 2009 may occur, possibly as the reverse in y-axis rotation of the rotation 2008. Similar to the example of FIG. 20A, the translation 2007 and the rotation 2009 may be detectable with one or more motion sensors 230 of the earbuds 100, for example the inertial measurement unit 226 and/or the gyroscope 228.

Through tracking the translation 2006, the translation 2007, the rotation 2008, and/or the rotation 2009 over a period of time (e.g., an epoch), periodic translation and rotational data for the earbud 100 may be recorded and assessed. Each inhalation 2000 and corresponding exhalation 2001 may be treated as a respiration event that may be assessed as a physiological indicator. The physiological indicator may be usable to generate physiological features (e.g., respiration rate, respiration rate variability), which are in turn potentially useful for determining cognitive state of the user 10 (e.g., an awake state, a pre-sleep or drowsy state, a sleep state, a REM sleep state, a NREM sleep state, a deep sleep state, etc.). Periods of time over which cognitive state of the user 10 occurs may then be used to infer the amount of sleep and/or rest the user 10 has accrued in a sleep session, which may also be of great value in assisting the user 10 to know when they have achieved sufficient sleep.

FIG. 21 illustrates physiological data comprising usable to determine a respiration event and/or a respiration rate through correlation with audio data for increased accuracy, according to one or more embodiments. The respiration rate may also be referred to as a "breath per minute" rate, or "BPM" rate.

In one or more embodiments, an audio signal 231 may be collected over a time period, processed, and then stored as the audio data 232. The processing of the audio signal 231 and/or digital data stored therefrom may include sorting and/or determining the amplitude of various frequencies. Frequencies may be determined accord to various frequency "bins", which may be arbitrarily defined. For example, the audio data 232 may describe an amplitude (including in a log scale such as decibels) for each of one or more frequency bins (e.g., in Hz) over the time period. The processed audio data 232 may be plotted in a Mel spectrogram to easily visualize the collected and processed data, as known in the art of audio engineering.

In FIG. 21, a Mel spectrogram is shown illustrating an audio data 232 collected on a microphone 212 of an earbud 100 worn by a user 10. The audio data 232 visualized in the Mel spectrogram of FIG. 21 was collected over a period of about 25.65 seconds, with x-axis units of set to approximately 0.038 seconds. The y-axis represents sound frequency in Hz. "Heatmap" coloration at each x-y point represents decibel level, e.g., the heatmap implements a 'z-axis' allowing for visualization of a third dimension. The heatmap of the Mel spectrogram has been converted to greyscale for case of presentation in this specification, where a lighter color at a given x-y coordinate represents a higher amplitude (e.g., louder sound at such a frequency bin and time value), and a darker coordinate at a different x-y coordinate represents a lower amplitude (e.g., softer sound at the different frequency bin and different time value).

In one or more embodiments, prominent sounds collected by the microphone may be determined by summing the amplitudes in all, or a subset, of frequency bins and plotting the summed values over time, e.g., "collapsing" the 'z-axis' into the y-axis. In the middle graph of FIG. 21, summed amplitudes of the audio data 232 visualized in the Mel spectrogram are illustrated over the same time period.

A peak detection algorithm may then be applied to determine points of 'maximum sound' over the time period. In FIG. 21, peaks identified by the peak detection algorithm are illustrated by dots at local maxima. The resulting peaks may be used to determine respiration events of the user 10. For example, periodic peaks within the 2 to 5 second range, and relatively similar peak height (e.g., relatively consistent breath loudness), may be used to identify respiration events. However, in one or more embodiments, and to improve recognition capability, the audio data 232 may also be coordinated with and/or analyzed in conjunction with motion data, as next described.

In one or more embodiments, motion data may be collected and stored over a time period for comparison to the processed instance of the audio data 232. In the bottom graph of the embodiment of FIG. 21, the motion data, for example, is shown (following processing) as plotted against time in a motion-over-time graph. The motion data illustrated in FIG. 21 was collected on an inertial measurement unit 236 of the earbuds 100.

In one or more embodiments, the motion data may be processed to result in one or more usable measures of motion or depravities thereof. For example, in one or more embodiments and the embodiment of FIG. 21, an attitude l2-norm signal may be calculated and utilized, which may be an orientation measure derived from the acceleration data 234 and/or the IMU data 236. The l2-norm signal may utilize the degree unit, once transformed, from the processed acceleration signal 233 and/or acceleration data 234. The y-axis may therefore represent a fraction of the angle (e.g., in degrees) associated with head movement (e.g., the head of the user 10) in a coordinate system where gravity (e.g., the direction of gravity 1500) is used as an orientation direction. In one or more embodiments, a resulting head position vector at a given time (e.g., at a time 't') and/or within a given timeframe may be obtained by filtering out any stable component. As a result, the minute changing components of the position and/or orientation that change with each breath may be determined. Such minute changes may result, for example, in whole or in part from the chest movement of the user 10 (e.g., the inflation 2002 and/or the expansion 2004 of FIG. 20A).

In one or more embodiments, the motion data collected may include acceleration data 234, as may be received from accelerometer 224 and/or determined from the IMU data 226. The acceleration data 234 and/or IMU data 236 may be utilized to calculate a pitch angle, a roll angle, and/or a yaw angle. The pitch angle, the yaw angle, and/or the roll angle may be processed to result in an attitude l2 norm. A high and/or low pass filter may be applied. A detection algorithm may then be applied to determine peaks in the attitude l2 norm data over time.

Following processing of the motion data and the audio data 232, each may be compared to determine close-in-time correspondence in peaks over the compared time periods. Where two corresponding peaks occur, a respiration event may be designated. Otherwise, where a peak occurs in one dataset but not the other (e.g., a spike in sound but not in motion, or vice-versa), such data may be discarded as unlikely to describe a respiration event. The motion data and the audio data 232 may be aligned utilizing timestamps, identical sample periods, peak alignment analysis within a probability limit, and/or other techniques known in the art of computer science or data analysis.

Although one example has been provided in FIG. 21, it will be recognized that other methods of sound and/or motion processing are possible. For example, Mel spectrogram analysis is utilized for ease of illustration and need not be utilized to implement one or more of the present embodiments.

In one or more embodiments, a method for determining respiration events receives an audio signal 231 that includes frequency ranges and associated amplitudes over a time period, and records the audio signal 231 as an audio data 232. The method sets one or more frequency bins over the time period, and then sums the amplitude within each frequency bin. Optionally, minimum amplitude, maximum amplitude, width (e.g., to separate from rolling sounds), and/or spread may be filtered to constrain peaks shape to those likely to be produced by breathing or another physiological indicator to be collected. Local maxima in the data may then be utilized to identify the "loudest" moment of a respiration event.

In one or more other embodiments, other methods, systems, and/or devices may be utilized to determine respiration events. For example, a method may utilize a machine learning algorithm to determine breaths from audio data. A machine learning model may be provided with audio data 232 that includes bin amplitude values, with supervised and/or unsupervised learning to classify the respiration events. The machine learning model, for example, could be provided with the frequencies over a given timeframe and their presence and/or amplitude signature may be able to be used for respiration event classification. Alternatively, or in addition, the machine learning model may be provided with the corresponding motion data or processed motion data over the same time period to further assist in event recognition.

Figure 22:
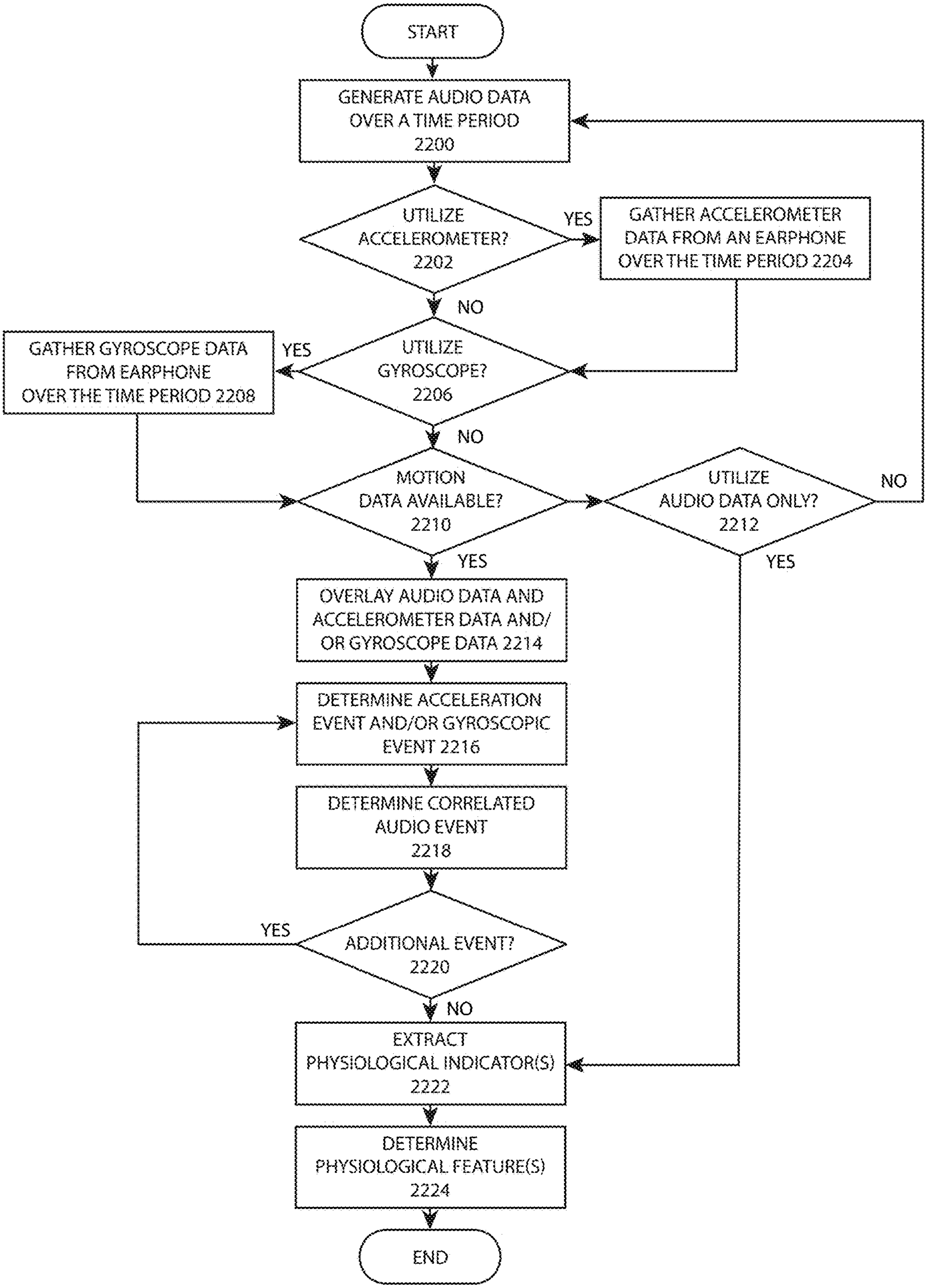
FIG. 22 illustrates a physiological feature identification process flow for determining a physiological feature of a user, such as heart rate and/or respiration rate, according to one or more embodiments.

FIG. 22 illustrates a physiological feature identification process flow 2250 for determining a physiological feature of a user 10, such as heart rate and/or respiration rate, according to one or more embodiments. Operation 2200 generates an audio data (e.g., the audio data 232) over a time period (e.g., 5 seconds, 10 seconds, 1 minute, 10 minutes). The audio data 232 may be generated from an audio signal 231 received on a microphone 212 and/or a microphone 612 if sufficiently close to the user 10 (e.g., a charging case 550 resting on a bedside collecting audio while the user 10 is sleeping). Operation 2202 determines whether an accelerometer 224 is to be utilized in the determination of physiological indicators, in which case operation 2204 gathers acceleration data 234 over the time period from an accelerometer 224 physically coupled to the user 10, for example an accelerometer 224 of the earphone (such as the earbud 100). Operation 2204 then proceeds to operation 2206. Operation 2206 may determine whether a gyroscope 228 is to be utilized in the determination of physiological indicators, in which case operation 2206 proceeds to operation 2208. Operation 2208 may then gather the gyroscope data 238 from a gyroscope 228 of a device physically associated with the user 10, such as an earphone like the earbud 100. Operation 2208 may then proceed to operation 2210.

Although not shown, a similar determination to operation 2202 and operation 2206 may be made for the IMU data 236, and where IMU data 236 is to be included the IMU data 236 may be gathered from the inertial measurement unit 226 over the time period.

Operation 2210 determines if sufficient motion data is available. If no motion data is available, or the data is otherwise insufficient, operation 2210 may proceed to operation 1212. Operation 1212 may determine whether audio data 232 may be solely used for the present determination of physiological indicators, in which case operation 1212 proceeds to operation 1222. Otherwise, if utilizing only audio is insufficient, operation 2212 may return to operation 2200. In one or more embodiments, utilizing only audio may be sufficient where the audio data 232 shows consistency with previously collected audio data 232 for a previous and/or immediately preceding time period, and/or meet other data quality measures.

Operation 2210 proceeds to operation 2214 where both audio data 232 and motion data are available. Operation 2214 may then overlay the audio data 232 and the motion data such as the acceleration data 234, the gyroscope data 238, and/or any IMU data 236. The overlay occurs for the same time period and/or epoch in which the data was collected. Operation 2216 may determine an acceleration event (e.g., indicating a translation, such as the translation 2006 and/or the translation 2007) and/or a gyroscopic event (e.g., indicating a rotation, such as the rotation 2008 and/or the rotation 2009). Operation 2216 may then proceed to operation 2218, which may determine a correlated audio event. For a respiration event, the majority of sensed translation and/or rotation (e.g., the user motion 50) may occur substantially synchronously with the sound of the user 10 (e.g., the user sound 40). For example, the sound of the inhalation 2000 and the exhalation 2001 may correspond with the most motion, where the beginning and end of a breath may correspond with the lease sensed motion. For audio that records a different physiological indicator, such as a heartbeat, an audio signal and/or peak may be offset from an accelerometer signal 233 generated by the beating heart, especially if the audio signal 231 is generated as a result of secondary effects of the heartbeat such as blood rushing through veins and/or arteries of the ear 11.

Once an audio event is correlated, a timestamp, elapse time, or other location designator within the time period may be specified and temporarily stored in computing memory.

Operation 2220 determines whether an additional event is present, in which case operation 2220 returns to operation 2216.

Once evaluation of correlated events is complete, operation 2220 may proceed to operation 2222 which may extract one or more physiological indicators from the overlayed audio data 232 and motion data. In one or more embodiments, operation 2222 may extract and store each physiological indicator in a physiological indicator data. The physiological indicator data may store data describing an occurrence of each event (e.g., an elapse time and other important features), and/or tagging or identifying each physiological indicator. For example, physiological indicators occurring in a long frequency of occurrence (e.g., several seconds apart) and sufficient motion (e.g., more than 1 centimeters, more than 5 degrees of rotation) may indicate respiration events, while short frequency of occurrence (e.g., one second or less) and reduced motion (e.g., less than 2 millimeters of motion, and with no perceptible rotation) may indicate heartbeats. Where operation 2222 may be arrived at from operation 2212, operation 2222 may extract physiological features based solely on audio, for example respiration events determined through sound. Operation 2222 may then proceed to operation 2224.

Operation 2224 may determine one or more physiological features. For example, each of the physiological indicators identified in operation 2222 may be counted, averaged against other epochs, and/or have additional calculations or analysis performed thereon. In a straightforward example, operation 2224 may determine a respiration rate and/or a heart rate through counts of respiration events and heartbeat events, respectively. Operation 2224 may also calculate, based on the epoch or in combination with one or more previous epochs, respiration rate variability and heart rate variability. Physiological features may be stored in a physiological feature data, which may be stored for statistical purposes for the user 10 and/or further evaluated for determination of the cognitive state of the user 10.

Although the present embodiments have been described with reference to specific example embodiments, it will be evident that various modifications and changes may be made to these embodiments without departing from the broader spirit and scope of the various embodiments. For example, the various devices, engines, agent, routines, and modules described herein may be enabled and operated using hardware circuitry (e.g., CMOS based logic circuitry), firmware, software, or any combination of hardware, firmware, and software (e.g., embodied in a non-transitory machine-readable medium). For example, the various electrical structure and methods may be embodied using transistors, logic gates, and electrical circuits (e.g., application specific integrated circuitry (ASIC) and/or Digital Signal Processor (DSP) circuitry).

In addition, it will be appreciated that the various operations, processes, and methods disclosed herein may be embodied in a non-transitory machine-readable medium and/or a machine-accessible medium compatible with a data processing system (e.g., the earbud 100, the charging case 550, the device 600). Accordingly, the specification and drawings are to be regarded in an illustrative rather than a restrictive sense.

The structures in the figures such as the engines, routines, and modules may be shown as distinct and communicating with only a few specific structures and not others. The structures may be merged with each other, may perform overlapping functions, and may communicate with other structures not shown to be connected in the figures. Accordingly, the specification and/or drawings may be regarded in an illustrative rather than a restrictive sense.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the preceding disclosure.

Embodiments of the invention are discussed above with reference to the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures.

From reading the present disclosure, other variations and modifications will be apparent to persons skilled in the art. Such variations and modifications may involve equivalent and other features which are already known in the art, and which may be used instead of or in addition to features already described herein.

Although claims have been formulated in this application to particular combinations of features, it should be understood that the scope of the disclosure of the present invention also includes any novel feature or any novel combination of features disclosed herein either explicitly or implicitly or any generalization thereof, whether or not it relates to the same invention as presently claimed in any claim and whether or not it mitigates any or all of the same technical problems.

Features which are described in the context of separate embodiments may also be provided in combination in a single embodiment. Conversely, various features which are, for brevity, described in the context of a single embodiment, may also be provided separately or in any suitable sub-combination. The applicants hereby give notice that new claims may be formulated to such features and/or combinations of such features during the prosecution of the present application or of any further application derived therefrom.

References to "one embodiment," "an embodiment," "example embodiment," "various embodiments," "one or more embodiments," etc., may indicate that the embodiment(s) of the invention so described may include a particular feature, structure, or characteristic, but not every possible embodiment of the invention necessarily includes the particular feature, structure, or characteristic. Further, repeated use of the phrase "in one embodiment," or "in an exemplary embodiment," "an embodiment," do not necessarily refer to the same embodiment, although they may. Moreover, any use of phrases like "embodiments" in connection with "the invention" are never meant to characterize that all embodiments of the invention must include the particular feature, structure, or characteristic, and should instead be understood to mean "at least one or more embodiments of the invention" includes the stated particular feature, structure, or characteristic.

The enumerated listing of items does not imply that any or all of the items are mutually exclusive, unless expressly specified otherwise.

It is understood that the use of a specific component, device and/or parameter names are for example only and not meant to imply any limitations on the invention. The invention may thus be implemented with different nomenclature and/or terminology utilized to describe the mechanisms, units, structures, components, devices, parameters and/or elements herein, without limitation. Each term utilized herein is to be given its broadest interpretation given the context in which that term is utilized.

Devices or system modules that are in at least general communication with each other need not be in continuous communication with each other, unless expressly specified otherwise. In addition, devices or system modules that are in at least general communication with each other may communicate directly or indirectly through one or more intermediaries.

A description of an embodiment with several components in communication with each other does not imply that all such components are required. On the contrary a variety of optional components are described to illustrate the wide variety of possible embodiments of the present invention.

A "computer" may refer to one or more apparatus and/or one or more systems that are capable of accepting a structured input, processing the structured input according to prescribed rules, and producing results of the processing as output. Examples of a computer may include: a computer; a stationary and/or portable computer; a computer having a single processor, multiple processors, or multi-core processors, which may operate in parallel and/or not in parallel; a general purpose computer; a supercomputer; a mainframe; a super mini-computer; a mini-computer; a workstation; a micro-computer; a server; a client; an interactive television; a web appliance; a telecommunications device with internet access; a hybrid combination of a computer and an interactive television; a portable computer; a tablet personal computer (PC); a personal digital assistant (PDA); a portable telephone; a smartphone, application-specific hardware to emulate a computer and/or software, such as, for example, a digital signal processor (DSP), a field-programmable gate array (FPGA), an application specific integrated circuit (ASIC), an application specific instruction-set processor (ASIP), a chip, chips, a system on a chip, or a chip set; a data acquisition device; an optical computer; a quantum computer; a biological computer; and generally, an apparatus that may accept data, process data according to one or more stored software programs, generate results, and typically include input, output, storage, arithmetic, logic, and control units.

Those of skill in the art will appreciate that where appropriate, one or more embodiments of the disclosure may be practiced in network computing environments with many types of computer system configurations, including personal computers, hand-held devices, multi-processor systems, microprocessor-based or programmable consumer electronics, network PCs, minicomputers, mainframe computers, and the like. Where appropriate, embodiments may also be practiced in distributed computing environments where tasks are performed by local and remote processing devices that are linked (either by hardwired links, wireless links, or by a combination thereof) through a communications network. In a distributed computing environment, program modules may be located in both local and remote memory storage devices.

The example embodiments described herein can be implemented in an operating environment comprising computer-executable instructions (e.g., software) installed on a computer, in hardware, or in a combination of software and hardware. The computer-executable instructions can be written in a computer programming language or can be embodied in firmware logic. If written in a programming language conforming to a recognized standard, such instructions can be executed on a variety of hardware platforms and for interfaces to a variety of operating systems. Although not limited thereto, computer software program code for carrying out operations for aspects of the present invention can be written in any combination of one or more suitable programming languages, including an object oriented programming languages and/or conventional procedural programming languages, and/or programming languages such as, for example, Hypertext Markup Language (HTML), Dynamic HTML, Extensible Markup Language (XML), Extensible Stylesheet Language (XSL), Document Style Semantics and Specification Language (DSSSL), Cascading Style Sheets (CSS), Synchronized Multimedia Integration Language (SMIL), Wireless Markup Language (WML), Java™, Jini™, C, C++, Smalltalk, Perl, UNIX Shell, Visual Basic or Visual Basic Script, Virtual Reality Markup Language (VRML), ColdFusion™ or other compilers, assemblers, interpreters or other computer languages or platforms.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

A network is a collection of links and nodes (e.g., multiple computers and/or other devices connected together) arranged so that information may be passed from one part of the network to another over multiple links and through various nodes. Examples of networks include the Internet, the public switched telephone network, the global Telex network, computer networks (e.g., an intranet, an extranet, a local-area network, or a wide-area network), wired networks, and wireless networks.

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

The flowchart and block diagrams in the figures illustrate the architecture, functionality, and operation of possible implementations of systems, methods and computer program products according to various embodiments. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

Further, although process steps, method steps, algorithms or the like may be described in a sequential order, such processes, methods and algorithms may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

It will be readily apparent that the various methods and algorithms described herein may be implemented by, e.g., appropriately programmed general purpose computers and computing devices. Typically a processor (e.g., a microprocessor) will receive instructions from a memory or like device, and execute those instructions, thereby performing a process defined by those instructions. Further, programs that implement such methods and algorithms may be stored and transmitted using a variety of known media.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article.

The functionality and/or the features of a device may be alternatively embodied by one or more other devices which are not explicitly described as having such functionality/features. Thus, other embodiments of the present invention need not include the device itself.

The term "computer-readable medium" as used herein refers to any medium that participates in providing data (e.g., instructions) which may be read by a computer, a processor or a like device. Such a medium may take many forms, including but not limited to, non-volatile media, volatile media, and transmission media. Non-volatile media include, for example, optical or magnetic disks and other persistent memory. Volatile media include dynamic random access memory (DRAM), which typically constitutes the main memory. Transmission media include coaxial cables, copper wire and fiber optics, including the wires that comprise a system bus coupled to the processor. Transmission media may include or convey acoustic waves, light waves and electromagnetic emissions, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, removable media, flash memory, a "memory stick", any other memory chip or cartridge, a carrier wave as described hereinafter, or any other medium from which a computer can read.

Where databases are described, it will be understood by one of ordinary skill in the art that (i) alternative database structures to those described may be readily employed, (ii) other memory structures besides databases may be readily employed. Any schematic illustrations and accompanying descriptions of any sample databases presented herein are exemplary arrangements for stored representations of information. Any number of other arrangements may be employed besides those suggested by the tables shown. Similarly, any illustrated entries of the databases represent exemplary information only; those skilled in the art will understand that the number and content of the entries can be different from those illustrated herein. Further, despite any depiction of the databases as tables, an object-based model could be used to store and manipulate the data types of the present invention and likewise, object methods or behaviors can be used to implement the processes of the present invention.

Embodiments of the invention may also be implemented in one or a combination of hardware, firmware, and software. They may be implemented as instructions stored on a machine-readable medium, which may be read and executed by a computing platform to perform the operations described herein.

More specifically, as will be appreciated by one skilled in the art, aspects of the present invention may be embodied as a system, method or computer program product. Accordingly, aspects of the present invention may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Unless specifically stated otherwise, and as may be apparent from the following description and claims, it should be appreciated that throughout the specification descriptions utilizing terms such as “processing,” “computing,” “calculating,” “determining,” or the like, refer to the action and/or processes of a computer or computing system, or similar electronic computing device, that manipulate and/or transform data represented as physical, such as electronic, quantities within the computing system’s registers and/or memories into other data similarly represented as physical quantities within the computing system’s memories, registers or other such information storage, transmission or display devices.

The term “processor” may refer to any device or portion of a device that processes electronic data from registers and/or memory to transform that electronic data into other electronic data that may be stored in registers and/or memory. A “computing platform” may comprise one or more processors.

Those skilled in the art will readily recognize, in light of and in accordance with the teachings of the present invention, that any of the foregoing steps and/or system modules may be suitably replaced, reordered, removed and additional steps and/or system modules may be inserted depending upon the needs of the particular application, and that the systems of the foregoing embodiments may be implemented using any of a wide variety of suitable processes and system modules, and is not limited to any particular computer hardware, software, middleware, firmware, microcode and the like. For any method steps described in the present application that can be carried out on a computing machine, a typical computer system can, when appropriately configured or designed, serve as a computer system in which those aspects of the invention may be embodied.

It will be further apparent to those skilled in the art that at least a portion of the novel method steps and/or system components of the present invention may be practiced and/or located in location(s) possibly outside the jurisdiction of the United States of America (USA), whereby it will be accordingly readily recognized that at least a subset of the novel method steps and/or system components in the foregoing embodiments must be practiced within the jurisdiction of the USA for the benefit of an entity therein or to achieve an object of the present invention.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

Having fully described at least one embodiment of the present invention, other equivalent or alternative methods of implementing the earphone, such as the earbud 100, according to the present invention will be apparent to those skilled in the art. Various aspects of the invention have been described above by way of illustration, and the specific embodiments disclosed are not intended to limit the invention to the particular forms disclosed. The particular implementation of the earphone may vary depending upon the particular context or application. The earbud 100 is just one example of an earphone having one or more of the present embodiments. It is to be further understood that not all of the disclosed embodiments in the foregoing specification will necessarily satisfy or achieve each of the objects, advantages, or improvements described in the foregoing specification.

Claim elements and steps herein may have been numbered and/or lettered solely as an aid in readability and understanding. Any such numbering and lettering in itself is not intended to and should not be taken to indicate the ordering of elements and/or steps in the claims.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The Abstract is provided to comply with 37 C.F.R. Section 1.72(b) requiring an abstract that will allow the reader to ascertain the nature and gist of the technical disclosure. It is submitted with the understanding that it will not be used to limit or interpret the scope or meaning of the claims. The following claims are hereby incorporated into the detailed description, with each claim standing on its own as a separate embodiment.

We claim:

1. An earphone comprising:

a housing, an inside face of the housing that faces toward a concha of an ear of a user when the earphone is seated in the ear, a speaker configured to audibly couple to an ear canal of the ear, a battery, a wireless network interface controller, a wireless antenna, an outside face of the housing that faces outward when the earphone is seated in the ear such that at least an exposed region unobstructed to a finger of the user, a charging connector of the earphone electrically coupled to the battery positioned on the outside face of the housing to prevent contact with the ear of the user when the earphone is seated in the ear of the user to at least one of reduce corrosion of the charging connector of the earphone, reduce dirt buildup, and improve comfort, and a boot surrounding the housing and comprising a first opening for a nozzle of the earphone directing sound into the ear canal of the ear and a second opening exposing the outside face of the earphone, wherein the boot further comprising an inside surface of the boot that faces inward toward the concha and contacts at least a portion of the concha to at least one of reduce dirt buildup and improve comfort.

2. The earphone of claim 1, further comprising:

a controller comprising a processor, a memory, and a surface area of the controller, a touch sensor set in the outside face of the housing configured to detect the finger of the user and produce a control signal for generation of a control input, wherein the touch sensor is positioned in an exposed region of the outside face such that the touch sensor is accessible to the finger of the user without being blocked by a tragus and an anti-tragus, and a first magnet of the earphone positioned on the outside face and configured to magnetically couple the outside face of the housing to a first magnet of a charging interface of a charging device to align the charging connector of the earphone with a charging connector of the charging interface of the charging device.

3. The earphone of claim 2, further comprising:

an antenna electrically coupled to a network interface controller for at least one of transmitting and receiving at least one of an audio signal and data, wherein the antenna comprises a portion of the antenna following a portion of a periphery of the outside face, wherein at least one of the first magnet of the earphone and the charging interface of the earphone are located on the outside face opposed to the portion of the periphery to reduce an RF interference with at least one of the first magnet of the earphone and the charging connector of the earphone, and wherein the portion of the periphery is located within the exposed region and opposite, across the outside face, an intertragic notch when the earphone is seated in the ear to reduce the RF interference with at least one of the ear and the finger.

4. The earphone of claim 3, further comprising:

a plate of the housing comprising an exterior surface of the plate and an interior surface of the plate, the exterior surface of the plate comprising the outside face of the housing, wherein the antenna conductively traced on the interior surface of the plate along the portion of the periphery to at least one of conserve the surface area of the controller and improve RF signal of the antenna, wherein the plate is injection molded and a conductive trace is engraved on the interior surface of the plate through laser direct structuring (LDS), and wherein the portion of the antenna is a majority of at least one of a linear distance of the antenna and a collection area of the antenna, and a microphone that is audibly coupled to a microphone port set in a central zone of the outside face of the earphone usable to at least one of detect and record an environmental sound.

5. The earphone of claim 2, further comprising:

a directional locking engine stored on the memory comprising computer readable instructions that when executed:

receive the control signal from a touch sensor of a first earphone generated by activation of the touch sensor, receive from an accelerometer of the earphone physically fixed relative to the outside face a first acceleration data comprising a positive acceleration indicating a direction of gravity;

determine a direction of the touch sensor relative to the direction of gravity; and determine whether to generate the control input from the control signal based on criteria comprising the direction of the touch sensor relative to the direction of gravity, to reduce a probability of a false positive of the control signal while the user is engaged in a resting position.

6. The earphone of claim 2, further comprising:

a physiological feature detection engine stored on the memory comprising computer readable instructions that when executed:

receive from an accelerometer of the earphone an accelerometer signal over a time period comprising one or more acceleration events;

store the accelerometer signal as an acceleration data for the time period in a computer readable memory;

receive an audio signal over the time period from a microphone comprising two or more audio events;

store the audio signal as an audio data in the computer readable memory;

overlay the acceleration data and the audio data for the time period;

determine a correlation between two or more acceleration events and the two or more audio events over the time period; and extract two or more physiological indicators matching the correlation of the two or more acceleration events and the two or more audio events over the time period, to reliably determine a physiological indicator for determining physiological features.

7. The earphone of claim 3, further comprising:

a retainer configured to assist in retention of the earphone in the ear of the user, wherein the retainer comprising a member extending outward from the housing and forming an arc fitting within an anti-helix of the ear when the earphone is seated in the ear, and wherein a touchable surface of the touch sensor is at least partially bounded by the anti-helix of the ear, the tragus of the ear, and the anti-tragus of the ear, a second magnet of the earphone configured to magnetically couple the outside face of the housing to a second magnet of the charging interface of the charging device, the first magnet of the earphone and the second magnet of the earphone rotationally constraining the earphone to align a charging pin of the earphone with a charging pin of the charging interface of the charging device, wherein the charging connector of the earphone is the charging pin of the earphone and the charging connector of the charging interface of the charging device is the charging pin of the charging interface of the charging device, vibrational control engine stored in the memory comprising computer readable instructions that when executed:

receive a first acceleration data comprising a vibration signal of the earphone;

compare the first acceleration data to a first acceleration signature that describes vibration of the earphone when the finger of the user moves across the at least one of the touch sensor and the outside face of the earphone; and determine whether to generate the control input based on criteria comprising a match between the first acceleration data and the first acceleration signature to reduce a probability of the false positive of the control signal while the user is engaging in rest, anatomical control engine stored in the memory comprising computer readable instructions that when executed:

receive a second acceleration data comprising a recoil signal of the earphone, compare the second acceleration data to a second acceleration signature that describes acceleration of the earphone when pressed by the finger of the user against an anatomical element of the ear and then released, wherein the anatomical element of the ear comprises at least one of the tragus, an intertragic notch, the anti-tragus, the anti-helix, an scapha, an cymba conchae, an cavum conchae, and an anterior crus of a helix; and determine whether to generate the control input from the control signal based on criteria further comprising a match between the second acceleration data and the second acceleration signature to reduce a probability of the false positive of the control signal while the user is engaged in a resting position, wherein the touch sensor and at least one of the charging connector of the earphone, the first magnet of the earphone, and a microphone port are coextensive on the outside face of the earphone to assist the user in positioning the finger to provide the control input through tactile feedback, wherein the concha of the user is solely contacted by a material of the boot when the earphone is seated in the ear, and wherein the ear of the user is solely contacted by at least one of the material of the boot and a material of the retainer when the earphone is seated in the ear.

8. A method for identifying a control input of a user, the method comprising:

receiving a control signal from a touch sensor of a first earphone generated by activation of the touch sensor, wherein the first earphone comprising a housing having an outside face of that faces outward when the first earphone is seated in an ear such that at least an exposed region is unobstructed to a finger of the user;

receiving from an accelerometer of the earphone physically fixed relative to the outside face a first acceleration data comprising a positive acceleration indicating a direction of gravity;

determining a direction of the touch sensor relative to the direction of gravity; and determining whether to generate the control input from the control signal based on criteria comprising the direction of the touch sensor relative to the direction of gravity, to reduce a probability of a false positive of the control signal while the user is engaged in a resting position.

9. The method of claim 8, further comprising:

determining that an axis extending perpendicularly through a surface of the touch sensor includes a directional component at least partially pointing toward the direction of gravity.

10. The method of claim 8, further comprising:

determining that an axis extending perpendicularly from a plane parallel to the exterior surface is less than or equal to a 45-degree angle from the direction of gravity; and determining that the axis extending perpendicularly from a plane parallel to the exterior surface is less than or equal to a 45-degree angle from the direction of gravity.

11. The method of claim 8, further comprising:

receiving a second acceleration data comprising a recoil signal of the first earphone, comparing the second acceleration data to a first acceleration signature that describes acceleration of the earphone when pressed by the finger of the user against an anatomical element of the ear and then released, wherein the anatomical element of the ear comprises at least one of a tragus, an intertragic notch, an antitragus, an anti-helix, an cymba conchae, an cavum conchae, and antihelical fold of a helix; and determining whether to generate the control input from the control signal based on criteria further comprising a match between the second acceleration data and the first acceleration signature to reduce the probability of the false positive of the control signal while the user is engaged in the resting position.

12. The method of claim 11, further comprising:

receiving a third acceleration data comprising a vibration signal of the first earphone;

comparing the third acceleration data to a second acceleration signature that describes vibration of the earphone when the finger of the user moves across the at least one of the touch sensor and the outside face of the earphone; and determining whether to generate the control input from the control signal based on criteria further comprising a match between the third acceleration data and the second acceleration signature to reduce the probability of the false positive of the control signal while the user is engaging in rest.

13. The method of claim 12, further comprising:

determining the match between the second acceleration data and the first acceleration signature;

determining the match between the third acceleration data and the second acceleration signature; and generating the control input from the control signal, wherein the control input comprising at least one of a play instruction, a pause instruction, a skip track instruction, a volume instruction, a masking mode instruction, a sleep check instruction, a transparency mode instruction, and a locking instruction, and wherein the touch sensor comprising at least one of a resistive sensor, a capacitive sensor, a pressure sensor, a surface acoustical wave sensor, and an infrared sensor.

14. The method of claim 8, further comprising:

determining a first earphone of a pair of earphones is facing downward, disabling at least one of a microphone of the first earphone and a touch sensor of the first earphone, determining a second earphone of the pair of earphones is facing upward, and enabling at least one of a microphone of the second earphone and a touch sensor of the second earphone.

15. A device for detecting physiological features of a user, the device comprising:

a processor, a memory, an acceleration agent comprising computer readable instructions that when executed:

receive from at least one of an accelerometer of an earphone and an inertial measurement unit of an earphone an accelerometer signal over a time period comprising one or more acceleration events, and store the accelerometer signal as an acceleration data for the time period in a computer readable memory;

an audio agent comprising computer readable instructions that when executed:

receive an audio signal over the time period from a microphone comprising two or more audio events, and store the audio signal as an audio data in the computer readable memory;

an audio-motion overlay routine comprising computer readable instructions that when executed overlay the acceleration data and the audio data for the time period;

an overlay correlation routine comprising computer readable instructions that when executed determine a correlation between two or more acceleration events and the two or more audio events over the time period; and a physiological indicator extraction routine comprising computer readable instructions that when executed extract two or more physiological indicators matching the correlation of the two or more acceleration events and the two or more audio events over the time period, to reliably determine a physiological indicator for determining a physiological feature.

16. The device of claim 15, wherein the acceleration data comprises a description of the inhaling and exhaling of the user, wherein the audio signal comprises audio of a sound of the user inhaling and exhaling, wherein the physiological indicator comprises a respiration event, wherein the physiological feature comprises a respiration rate, and wherein the earphone comprises the microphone and the microphone is an external-facing microphone.

17. The device of claim 15, wherein the acceleration data comprises a description of the beating of a heart of the user, wherein the physiological indicator comprises a heartbeat, wherein the physiological feature comprises a heart rate, and wherein the earphone comprises the microphone and the microphone is an internal-facing microphone.

18. The device of claim 15, wherein the device further comprising computer readable instructions that when executed:

determine an amplitude of one or more frequency bins within the audio data over the time period, sum the amplitudes of each of the one or more frequency bins, apply a peak detection algorithm to determine one or more peaks over the time period, and match one or more peaks to two or more acceleration events.

19. The device of claim 16, further comprising:

a physiological feature determination routine comprising computer readable instructions that when executed determine the respiration rate of the user based on the one or more acceleration events over the time period; and a cognitive state determination module comprising computer readable instructions that when executed determine a cognitive state of the user based on the respiration rate, wherein the cognitive state comprises at least one of an awake state, a pre-sleep state, a sleep state, a REM state, and a NREM state.

20. The device of claim 15, further comprising:

a gyroscope agent comprising computer readable instructions that when executed:

receive from a gyroscope of the earphone a gyroscope signal over the time period comprising one or more axis rotation events, and store the gyroscope signal as a gyroscope data for the time period in the computer readable memory;

an audio-motion overlay routine comprising computer readable instructions that when executed overlay the gyroscope data with at least one of the acceleration data and the audio data for the time period; and an overlay correlation routine comprising computer readable instructions that when executed determine over the time period the correlation between two or more axis rotation events and any one of (i) the two or more acceleration events and (ii) the two or more audio events.

* * * * *